US011925662B2

(12) United States Patent
Eruslanov et al.

(10) Patent No.: US 11,925,662 B2
(45) Date of Patent: Mar. 12, 2024

(54) COMPOSITIONS AND METHODS OF ENHANCING ANTI-TUMOR RESPONSE USING HYBRID NEUTROPHILS

(71) Applicant: THE TRUSTEES OF THE UNIVERSITY OF PENNSYLVANIA, Philadelphia, PA (US)

(72) Inventors: Evgeniy Eruslanov, Havertown, PA (US); Steven Albelda, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 377 days.

(21) Appl. No.: 17/122,521

(22) Filed: Dec. 15, 2020

(65) Prior Publication Data

US 2021/0268020 A1 Sep. 2, 2021

Related U.S. Application Data

(63) Continuation of application No. 15/756,473, filed as application No. PCT/US2016/049205 on Aug. 29, 2016, now abandoned.

(60) Provisional application No. 62/212,279, filed on Aug. 31, 2015.

(51) Int. Cl.

| | |
|---|---|
| ***A61K 35/15*** | (2015.01) |
| ***A61K 31/454*** | (2006.01) |
| ***A61K 38/19*** | (2006.01) |
| ***A61K 38/21*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***C12N 5/0787*** | (2010.01) |

(52) U.S. Cl.

CPC ............ *A61K 35/15* (2013.01); *A61K 31/454* (2013.01); *A61K 38/193* (2013.01); *A61K 38/217* (2013.01); *A61K 39/0011* (2013.01); *A61K 39/39541* (2013.01); *A61K 45/06* (2013.01); *A61P 35/00* (2018.01); *C12N 5/0642* (2013.01); *A61K 2039/5158* (2013.01); *A61K 2039/572* (2013.01); *A61K 2039/585* (2013.01); *A61K 2300/00* (2013.01); *C12N 2501/22* (2013.01); *C12N 2501/24* (2013.01); *C12N 2501/599* (2013.01); *C12N 2502/30* (2013.01)

(58) Field of Classification Search

None

See application file for complete search history.

(56) References Cited

U.S. PATENT DOCUMENTS

| | | | |
|---|---|---|---|
| 8,778,677 | B2 | 7/2014 | Kaseko et al. |
| 9,005,619 | B2 | 4/2015 | Kohrt et al. |
| 2005/0201992 | A1 | 9/2005 | Moviglia |
| 2006/0084167 | A1 | 4/2006 | Cohenford et al. |
| 2012/0225038 | A1 | 9/2012 | Bronte |

OTHER PUBLICATIONS

Van Egmond, M. 2013. Neutrophils as effector cells for antibody-based immunotherapy of cancer. Seminars in Cancer Biology 23: 190-199; specif. pp. 190, 191, 192, 193, 194, 195.*

Matsushima, H. et al. 2013. Neutrophil differentiation into a unique hybrid population exhibiting dual phenotype and functionality of neutrophils and dendritic cells. Blood 121(10): 1677-1689; specif. pp. 1677, 1681, 1684.*

Albanesi, M. et al. 2013. Neutrophils mediate antibody-induced antitumor effects in mice. Blood 122(18): 3160-3164 and Supplementary data pp. 1-13; specif. pp. 3160, 3161 & Suppl. data, p. 2.*

Eruslanov, E.B. et al. 2014. Tumor-associated neutrophils stimulate T cell responses in early-stage human lung cancer. Journal of Clinical Investigation 124(12): 5466-5480; specif. pp. 5466, 5467, 5468, 5477.*

Fridlender, Z.G. et al. 2012. Transcriptomic analysis comparing tumor-associated neutrophils with granulocytic myeloid-derived suppressor cells and normal neutrophils. PLoS ONE 7(2): 1-13; specif. pp. 1, 9.*

International Search Report and Written Opinion for PCT International Application No. PCT/US2016/049205 dated Nov. 23, 2016.

Albanesi , et al., "Neutrophils mediate antibody-induced antitumor effects in mice", Blood. 122(18), Oct. 2013, 3160-3164.

Cartron , et al., "Granulocyte-macrophage colony-stimulating factor potentiates rituximab in patients with relapsed follicular lymphoma: results of a phase II study", J Clin Oncol. 26(16), Jun. 2008, 2725-2731.

Dumortier, A., et al., "Ikaros regulates neutrophil differentiation", Blood, 101(6), 2219-2226, 2003, specifically pp. 2219-2222 and 2224.

(Continued)

*Primary Examiner* — Adam Weidner

*Assistant Examiner* — Sharon M. Papciak

(74) *Attorney, Agent, or Firm* — Saul Ewing LLP; Kathryn Doyle

(57) ABSTRACT

The present invention relates to compositions and methods that provide novel anti-tumor therapies in cancer. In one aspect, the present invention features a hybrid neutrophil in a non-naturally occurring container, wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89. In another aspect, the present invention features methods of generating a hybrid neutrophil. In still another aspect, the present invention features methods of inhibiting tumor growth in a subject, treating a tumor in a subject, and increasing efficacy of an antibody against a tumor in a subject. The methods comprise (a) administering to the subject an effective amount of an anti-tumor antibody and (b) administering to or generating in the subject an effective amount of a hybrid neutrophil.

16 Claims, 55 Drawing Sheets

(56) References Cited

OTHER PUBLICATIONS

Eruslanov , et al., "Tumor-associated neutrophils stimulate T cell responses in early-stage human lung cancer", The Journal of Clinical Investigation, vol. 124, No. 12, Nov. 2014, 5466-5480.

Fury , et al., "A phase-I trial of the epidermal growth factor receptor directed bispecific antibody MDX-447 without and with recombinant human granulocyte-colony stimulating factor in patients with advanced solid tumors", Cancer Immunol Immunother. 57(2), Feb. 2008, 155-163 (abstract only).

García-García , et al., "FcgammaRIIA and FcgammaRIIIB mediate nuclear factor activation through separate signaling pathways in human neutrophils", J Immunol. 182(8), Apr. 2009, 4547-4556.

Gul , et al., "Macrophages eliminate circulating tumor cells after monoclonal antibody therapy", J Clin Invest. 24(2), Feb. 2014, 812-823.

Hatjiharissi , et al., "Increased natural killer cell expression of CD16, augmented binding and ADCC activity to rituximab among individuals expressing the Fc{gamma}RIIIa-158 V/V and V/F polymorphism", Blood. 110(7), Oct. 2007, 2561-2564.

Hernandez-Ilizaliturri , et al., "Neutrophils contribute to the biological antitumor activity of rituximab in a non-Hodgkin's lymphoma severe combined immunodeficiency mouse model", Clin Cancer Res. 9(16 Pt 1), Dec. 2003, 5866-5873.

Jiang , et al., "Pivotal role of phosphoinositide-3 kinase in regulation of cytotoxicity in natural killer cells", Nat Immunol. 1(5), Nov. 2000, 419-425 (abstract only).

Joshi , et al., "The PtdIns 3-kinase/Akt pathway regulates macrophage-mediated ADCC against B cell lymphoma", PLoS One. 4(1), 2009, e4208.

Liu , et al., "Cetuximab-based therapy versus non-cetuximab therapy for advanced cancer: a meta-analysis of 17 randomized controlled trials.", Cancer Chemother Pharmacol. 65(5), Apr. 2010, 849-861 (abstract only).

Matsushima, H., et al., "Neutrophil differentiation into a unique hybrid population exhibiting dual phenotype and functionality of neutrophils and dendritic cells", Blood, 121(10), 1677-1689, 2013.

Musolino , et al., "Immunoglobulin G fragment C receptor polymorphisms and clinical efficacy of trastuzumab-based therapy in patients with HER-2/neu-positive metastatic breast cancer", J Clin Oncol. 26(11), Apr. 2008, 1789-1796.

Niitsu , et al., "Phase I study of Rituximab—CHOP regimen in combination with granulocyte colony-stimulating factor in patients with follicular lymphoma", Clin Cancer Res. 10(12 Pt 1), Jun. 2004, 4077-4082.

Pullarkat , et al., "A phase I study of a HER2/neu bispecific antibody with granulocyte-colony-stimulating factor in patients with metastatic breast cancer that overexpresses HER2/neu", Cancer Immunol Immunother. 48(1), Apr. 1999, 9-21 (abstract only).

Repp , et al., "Phase I clinical trial of the bispecific antibody MDX-H210 (anti-FcgammaRI x anti-HER-2/neu) in combination with Filgrastim (G-CSF) for treatment of advanced breast cancer", Br J Cancer. 89(12), Dec. 2003, 2234-2243.

Van Der Kolk , et al., "Treatment of relapsed B-cell non-Hodgkin's lymphoma with a combination of chimeric anti-CD20 monoclonal antibodies (rituximab) and G-CSF: final report on safety and efficacy", Leukemia. 17(8), Aug. 2003, 1658-1664.

Wei , et al., "Control of lytic function by mitogen-activated protein kinase/extracellular regulatory kinase 2 (ERK2) in a human natural killer cell line: identification of perforin and granzyme B mobilization by functional ERK2", J Exp Med. 187(11), Jun. 1998, 1753-1765.

Wolschke, C., et al., "Postallograft lenalidomide induces strong NK cell-mediated antimyelomaactivity and risk for T cell-mediated GvHD: Results from a phase I/IIdose-finding study", Experimental Hematology, 41:134-142, 2013.

* cited by examiner

FIG. 12

| | |
|---|---|
| Cancer Type: | |
| Adenocarcinoma | 73 |
| Squamous Cell Carcinoma | 36 |
| Age: | |
| Median | 67 |
| Average | 67.9 |
| Range | 52-88 |
| Sex: | |
| Male | 66 |
| Female | 43 |
| Race: | |
| White | 74 |
| Black | 26 |
| Hispanic | 1 |
| Other | 8 |
| Tumor Stage: | |
| Stage IA | 49 |
| Stage IB | 31 |
| Stage IIA | 20 |
| Stage IIB | 9 |
| Tumor Grade: | |
| T1a | 39 |
| T1b | 18 |
| T2a | 34 |
| T2b | 10 |
| T3 | 8 |
| Nodal Stage: | |
| N0 | 96 |
| N1 | 13 |
| N2 | 0 |
| Smoking History: | |
| Current | 29 |
| Former | 69 |
| Never | 10 |
| Unknown | 1 |

COMPOSITIONS AND METHODS OF ENHANCING ANTI-TUMOR RESPONSE USING HYBRID NEUTROPHILS

CROSS-REFERENCE TO RELATED APPLICATIONS

This present application is a continuation of, and claims priority to, U.S. patent application Ser. No. 15/756,473 filed Feb. 28, 2018, which is a 35 U.S.C. § 371 national phase application from, and claims priority to, International Application No. PCT/US2016/049205, filed Aug. 29, 2016 and published under PCT Article 21(2) in English, which claims priority to U.S. Provisional Patent Application No. 62/212,279, filed Aug. 31, 2015, all of which applications are incorporated herein by reference in their entireties.

STATEMENT REGARDING FEDERALLY SPONSORED RESEARCH OR DEVELOPMENT

This invention was made with government support under grant numbers CA163256 and CA187392 awarded by the National Institutes of Health and grant W81XWH-15-1-0717 awarded by the Army Medical Research and Material Command. The government has certain rights in the invention.

BACKGROUND OF THE INVENTION

Neutrophils are antimicrobial effector cells equipped with powerful killing machinery to respond to pathogens, especially to opsonized bacteria. It is thought that therapeutic antibodies against tumor antigens can direct and activate this cytotoxic machinery against opsonized tumor cells through Fc receptors, a process that is referred to as antibody-dependent cellular cytotoxicity (ADCC) (Musolino et al., *J Clin Oncol.* 2008; 26(11): 1789-1796; Albanesi et al., *Blood.* 2013 Aug. 26 PMID23980063; Hernandez-Ilizaliturri et al., *Clin Cancer Res.* 2003 Dec. 1; 9(16 Pt 1): 5866-5873). Unfortunately, the clinical efficacy of many therapeutic antibodies is poor and needs to be enhanced (Liu et al., *Cancer Chemother Pharmacol.* 2010 April; 65(5): 849-861; Fury et al., *Cancer Immunol Immunother.* 2008 February; 57(2): 155-163; Repp et al., *Br J Cancer.* 2003 Dec. 15; 89(12): 2234-2243). The identification and administration of efficient effector subsets responsible for mediating sufficient ADCC in humans could lead to the development of more synergistic and combination therapies that would enhance the effect of therapeutic antibodies.

Treatment of tumors with anti-tumoral antibodies such as anti-Her2/neu, rituximab, necitumumab, panitumumab, or cetuximab in combination with G-CSF/GM-CSF to induce the recruitment of effector neutrophils from bone marrow was used in several clinical trials (Repp et al., *Br J Cancer.* 2003 Dec. 15; 89(12): 2234-2243; Pullarkat et al., *Cancer Immunol Immunother.* 1999 April; 48(1): 9-21; Cartron et al., *J Chn Oncol.* 2008 Jun. 1; 26(16): 2725-2731; van der Kolk et al., *Leukemia.* 2003 August; 17(8): 1658-1664; Niitsu et al., *Clin Cancer Res.* 2004 Jun. 15; 10(12 Pt 1): 4077-4082). However, these trials only showed limited therapeutic effects, indicating that improvement of neutrophil-mediated Ab therapy is required. Several FcγR-bearing myeloid cell populations have been proposed as a potential effector cells for monoclonal antibody-mediated tumor regression, including natural killer (NK) cells, monocytes, macrophages and neutrophils (Hernandez-Ilizaliturri et al., *Clin Cancer Res.* 2003 Dec. 1; 9(16 Pt 1): 5866-5873; Repp et al., *Br J Cancer.* 2003 Dec. 15; 89(12): 2234-2243; Gul et al., *J Chn Invest.* 2014 Feb. 3; 124(2): 812-823; Hatjiharissi et al., *Blood.* 2007 Oct. 1; 110(7): 2561-2564; Pullarkat et al., *Cancer Immunol Immunother.* 1999 April; 48(1): 9-21). The expansion and/or activation of these cells in a human represents an attractive strategy to enhance the efficacy of therapeutic antibodies through the induction of ADCC.

A need exists in the art for novel anti-tumor therapies, especially for enhancing the efficacy of therapeutic anti-tumor antibodies. The present invention satisfies this need.

SUMMARY OF THE INVENTION

As described herein, the present invention relates to compositions, methods, and uses for hybrid neutrophils. In one aspect, the invention includes a method of generating a hybrid neutrophil. The method comprises contacting a composition comprising a bone marrow (BM) immature CD15-positive ($CD15^+$) cell with an amount of tumor conditioned medium. The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In another aspect, the invention includes a method of generating a hybrid neutrophil comprising contacting a composition comprising a bone marrow (BM) immature CD15-positive ($CD15^+$) cell with an amount of interferon γ (IFN-γ) and an amount of granulocyte macrophage colony stimulating factor (GM-CSF). The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In yet another aspect, the invention includes a method of generating a hybrid neutrophil comprising contacting a composition comprising a bone marrow (BM) immature CD15-positive ($CD15^+$) cell with an amount of an agent that reduces the level of Ikaros polypeptide in the cell and an amount of granulocyte macrophage colony stimulating factor (GM-CSF). The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In still another aspect, the invention includes a method of generating a hybrid neutrophil comprising contacting a composition comprising peripheral blood immature neutrophils with an amount of tumor conditioned medium. The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In another aspect, the invention includes a method of generating a hybrid neutrophil comprising contacting a composition comprising peripheral blood immature neutrophils with an amount of interferon γ (IFN-γ) and an amount of granulocyte macrophage colony stimulating factor (GM-CSF). The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

Another aspect of the invention includes a method of inhibiting tumor growth in a subject. The method comprises (a) administering to the subject an effective amount of an anti-tumor antibody or an antigen-binding fragment thereof; and (b) administering to or generating in the subject an effective amount of a hybrid neutrophil. The hybrid neutrophil expresses at least one neutrophil associated marker selected from the group consisting of: Arg1, MPO, CD66b, and CD15, and at least one antigen-presenting cell (APC) associated marker selected from the group consisting of: CD14, HLA-DR, CD32, CD64, and CD89. The method thereby inhibits tumor growth in the subject.

Yet another aspect of the invention includes a method of increasing efficacy of an antibody against a tumor in a subject. The method comprises (a) administering to the subject an effective amount of an anti-tumor antibody or an antigen-binding fragment thereof; and (b) administering to or generating in the subject an effective amount of a hybrid neutrophil. The hybrid neutrophil expresses at least one neutrophil associated molecule selected from the group consisting of: Arg1, MPO, CD66b, and CD15, and at least one antigen-presenting cell (APC) associated molecule selected from the consisting of: CD14, HLA-DR, CD32, CD64, and CD89. The method thereby increases efficacy of the antibody against the tumor in the subject.

Still another aspect includes a method of treating a tumor in a subject comprising (a) administering to the subject an effective amount of an anti-tumor antibody or an antigen-binding fragment thereof; and (b) administering to or generating in the subject an effective amount of a hybrid neutrophil. The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89. The method thereby treats the tumor in the subject.

Another aspect of the invention includes a hybrid neutrophil in a non-naturally occurring container. The hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In various embodiments of the above aspects or any other aspect of the invention delineated herein, the peripheral blood immature neutrophils are mobilized in peripheral blood by contacting peripheral blood with an amount of granulocyte macrophage colony stimulating factor (GM-CSF) or an amount of granulocyte colony stimulating factor (G-CSF). In another embodiment, the amount of granulocyte macrophage colony stimulating factor (GM-CSF) or the amount of interferon γ (IFN-γ) is at least about 50 pg/ml, at least about 60 pg/ml, at least about 70 pg/ml, at least about 80 pg/ml, at least about 90 pg/ml, or at least about 100 pg/ml.

In another embodiment, the agent that reduces the level of Ikaros polypeptide in the cell is lenalidomide. In yet another embodiment, the amount of tumor conditioned medium is about 50% v/v.

In still another embodiment, the hybrid neutrophil further expresses at least one molecule selected from the group consisting of: MHC class I, MEW class II, OX40L, 4-1BBL, CD86, CD40, and CCR7. In another embodiment, the expression level of any one of the molecules is low, intermediate, or high. In yet another embodiment, the expression of any one of the molecules is increased relative to expression of the molecule on a canonical tumor-associated neutrophil (TAN).

In another embodiment, the hybrid neutrophil expresses CD14, HLA-DR, CD32, CD64, and CD89. In yet another embodiment, the hybrid neutrophil expresses Arg1, MPO, CD66b, CD15, CD14, HLA-DR, MEW class I, OX40L, 4-1BBL, CD86, CD40, CCR7, CD32, CD64, and CD89. In still another embodiment, the expression of CD32 and/or CD64 and/or CD89 is high.

In certain embodiments, the anti-tumor antibody is selected from the group consisting of: anti-Her2/neu antibody, rituximab, necitumumab, panitumumab, and cetuximab. In another embodiment, the step of administering to the subject an effective amount of a hybrid neutrophil increases antibody-dependent cellular cytotoxicity (ADCC), antibody-dependent phagocytosis (ADP), or effector T cell response in the subject. In another embodiment, the step of administering to or generating in the subject an effective amount of a hybrid neutrophil is followed by the step of administering to the subject an effective amount of an anti-tumor antibody or an antigen-binding fragment thereof. In yet another embodiment, the step of administering to or generating in the subject an effective amount of a hybrid neutrophil is concurrent with the step of administering to the subject an effective amount of an anti-tumor antibody or an antigen-binding fragment thereof. In one embodiment, the subject is human. In another embodiment, the tumor comprises non-small cell lung cancer (NSCLC).

In another embodiment, the hybrid neutrophil is generated ex vivo in a biological sample obtained from the subject. In yet another embodiment, the biological sample is blood or bone marrow. In still another embodiment, the hybrid neutrophil is generated in situ in the subject. In another embodiment, the hybrid neutrophil is generated in situ by administering to the subject an amount of granulocyte macrophage colony stimulating factor (GM-CSF) and at least one agent selected from the group comprised of: IFN-γ and lenalidomide.

In yet another embodiment, the hybrid neutrophil population is generated by a method according to any one of the claims of the present invention.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1C shows the frequency of $HLA\text{-}DR^{+}$ hybrid TANs among all TANs in cancer patients (n=45) analyzed by flow cytometry of tumor digests.

As shown in FIG. 2A, the purified BM $CD15^+$ cells were MPO-positive "band-like" neutrophils. FIG. 2B shows bone marrow neutrophils (BMN) that were purified and cultured in the presence or absence of IFN-γ and GM-CSF for 6 days at the concentrations of 100 pg/ml. Fixable Viability dye FVD660 was used to discriminate viable neutrophils in cell culture. In FIG. 2C, purified BM CD15 neutrophils were cultured with hybrid-inducing TCM for 5-7 days (top panel). Hybrid cells are highlighted in boxes. To obtain canonical neutrophils, BM CD15 neutrophils were cultured with TCM collected from patients where hybrid TANs were not found (bottom panel). The indicated cell surface markers were analyzed by flow cytometry on the gated $CD11b^+CD15^+CD66b^+$ live cells. Hybrid neutrophils were purified with HLA-$DR^+$ beads, spun on glass slides and stained with the Hema3 Stat Pack Kit.

FIG. 3A shows the differentiation of $CD15^+$ bone marrow neutrophils (BMNs) into HLA-$DR^+CD14^+$ hybrid neutrophils in the presence of tumor conditioned media (TCMs) collected from cancer patients or with IFN-γ and GM-CSF at a concentration of 100 pg/ml. The expression of CD14 and HLA-DR was analyzed on gated live $CD11b^+$ $CD15^{hi}CD66b^+$ cells by flow cytometry on day 7 of treatment. FIG. 3B shows the development of HLA-$DR^+$ $CD14^+$ hybrid neutrophils in the presence of lenalidomide (10 μM) and/or GM-CSF (100 pg/ml). Expression of HLA-DR and CD14 molecules was analyzed on gated live $CD11b^+CD15^+$ BMNs at day 6 of differentiation. In FIG. 3C, low density neutrophils were isolated from G-CSF treated cancer patients by gradient separation and cultured in the presence of IFN-γ and GM-CSF at concentration 100 pg/ml for 7 days. The expression of HLA-$DR^+$ and $CD14^+$ was measured on gated live $CD11b^+CD66b^+CD15^+$ cells. In FIGS. 3D-3E, neutrophils were isolated from peripheral blood (PB) and bone marrow (BM) using anti-CD15 beads and stained for CD16 and CD10 markers. FIG. 3F shows BM CD15 cells treated with TCMs collected from different patients (top panel) or with IFN-γ and GM-CSF at concentration 20 pg/ml (low panel). Five days later, expression of CD14 and HLA-DR was analyzed on gated $CD11b^+CD15^+$ live cells by flow cytometry.

FIG. 5A shows bone marrow (BM) derived hybrid (black line) and canonical (grey line) neutrophils incubated with pHrodo™ Red *E. coli* BioParticles® for 45 minutes to allow phagocytosis (internalized particles become fluorescent red). In FIG. 5B, BM derived canonical and hybrid neutrophils were incubated with Cetuximab opsonized A431 tumor cell line labeled with DIO dye for 4 hrs. Cell cultures were collected and stained for CD66b to visualize neutrophils. Antibody dependent phagocytosis (ADP) was evaluated by flow cytometry as a percentage of double positive cells. To confirm ADP, stained cells were spun on glass slides and examined for double positive cells. In FIG. 5C, non-activated or phorbol myristate acetate (PMA) (40 ng/ml) activated peripheral blood neutrophil (PBN), tumor-associated neutrophil (TAN), hybrid and canonical bone marrow neutrophils (BMNs) were incubated with adherent GFP-A549 tumor cells for 24 hours in 96 Well Black Flat Bottom Microplate (Corning®) that has low fluorescent background. To induce ADCC by neutrophils, A549 tumor cells were opsonized with anti-EGFR monoclonal antibodies (Cetuximab), 1 μg/ml for 30 min at 4 C. These opsonized cells were incubated with neutrophils for 24 hours. Tumor cell cytotoxicity was calculated by comparing the remaining cell-associated GFP fluorescence of adherent tumor cells cultured with neutrophils to control wells (tumor cells without neutrophils). FIG. 5D shows canonical and hybrid neutrophils differentiated from immature BM CD15 cells. The expression of Fcγ receptors (FcγRs) was analyzed on gated live canonical and hybrid neutrophils by flow cytometry.

FIG. 6A shows the effect of BM-derived canonical HLA-$DR^-$ and hybrid HLA-$DR^+$ neutrophils on T cell proliferation (top panel) and IFN-γ by activated T cells (bottom panel). CFSE-labeled autologous peripheral blood mononuclear cells (PBMCs) were stimulated with plate-bound anti-CD3 antibodies and mixed with canonical and hybrid neutrophils at a 1:1 ratio for 4 days. To measure intracellular IFN-γ in CD3 cells, the autologous PBMCs were stimulated with plate-bound anti-CD3 and CD28 antibodies and mixed with canonical and hybrid neutrophils at a 1:1 ratio for 48 hrs. In FIG. 6B, the effect of BM-derived HLA-$DR^+$ hybrid neutrophils on NY-ESO-specific effector T cell responses is shown. Human TCR-transfected CD8 effector T cells (Ly95 cells) that recognize a HLA-A*02-restricted peptide of NY-ESO-1 were stimulated with genetically modified A549 tumor cell line expressing NY-ESO-1 and HLA-A*02. The percentage of IFN-γ (top panel) and Granzyme B (low panel) positive TCR Vβ 13.1-transfected CD8 cells (Ly95 cells) cultured in the presence of BM-derived HLA-$DR^-$ or HLA-$DR^+$ neutrophils was measured by intracellular staining at 24 hours after stimulation. FIG. 6C shows autologous T cells isolated from PBMC and co-cultured with BM-derived canonical HLA-$DR^-$ and hybrid HLA-$DR^+$ neutrophils that had been pulsed with a mixture of viral T cell epitopes for 2 hours. The number of IFN-γ-producing T cells was determined in three independent ELISpot assays. Error bars represent mean±SEM from 3 independent experiments (*$p \leq 0.01$, Mann-Whitney test). FIG. 6D shows the ability of BM-derived canonical HLA-$DR^-$ or hybrid HLA-$DR^+$ neutrophils to trigger NYESO-specific effector T cell responses. HLA-$A2^+$ canonical or hybrid neutrophils were pulsed with NY-ESO-1 peptide for 1 hour, washed and cultured with Ly95 cells at a 1:1 ratio for 24 hrs. Antigen-specific activation of the Ly95 cells was assessed by measuring intracellular IFN-γ. In FIGS. 6E-6H, TAN subsets were isolated by flow cytometry sorting based on the phenotype of canonical ($CD11b^+CD66b^+CD15^+$) and hybrid ($CD11b^+CD66b^+CD15^+$HLA-$DR^+CD14^+$) TANs. BM-derived hybrid neutrophils were differentiated with hybrid-inducing TCM. CFSE-labeled PBMC isolated from a healthy donor were stimulated with plate-bound anti-CD3 antibodies and mixed with canonical, hybrid TAN and BM hybrid cells at ratio 1:1 for 4 days. Numbers on histograms represent the percentage of proliferating T cells (FIGS. 6E-6H). The percentage of IFN-γ (FIGS. 6I-6J) and Granzyme B (FIGS. 6K-6L) positive TCR Vβ 13.1-transfected CD8 cells cultured in the presence or absence BM hybrid neutrophils was measured by intracellular staining at 24 hours after stimulation with A2/ESO A549 cells. FIG. 6M shows antigen-presenting activity of canonical and hybrid neutrophils and cross-presentation of viral epitopes. Tumor or BM-derived hybrid and canonical neutrophils were pulsed with peptide pool of viral antigens (CD8 epitopes from human CMV, Epstein-Barr, flu viruses, and tetanus toxoid from all the common HLA types) and co-cultured with autologous T cells for 24 hrs. IFN-γ production was assessed by ELISpot. Hybrid, canonical BMNs and monocyte-derived DC (Mo-DC) were incubated with DQ-OVA for 30 min at 37° C. (black) or at 4° C. (grey-tinted) (lower panel). DQ-OVA exhibits bright green fluorescence upon proteolytic degradation.

In FIG. 7A, the expression of FcγRs was analyzed on gated live canonical $CD11b^+CD15^{hi}CD66b^+HLA\text{-}DR^-$ cells and hybrid neutrophils $CD11b^+$ $CD15^{hi}CD66b^+HLA\text{-}DR^+$ by flow cytometry. Tumor derived (TAN, top panel) and BM-derived neutrophils (BMN, bottom panel). In FIG. 7B, non-activated or PMA (40 ng/ml) activated PBN, TAN, hybrid and canonical BMNs were incubated with adherent GFP-A549 tumor cells for 24 hours in 96 Well Black Flat Bottom Microplate (Corning®) that has the low fluorescent background. To induce ADCC by neutrophils, A549 tumor cells were opsonized with anti-EGFR monoclonal antibodies (mAbs) (Cetuximab), 1 μg/ml for 30 min at 4° C. These opsonized cells were incubated with neutrophils for 24 hours. Tumor cell cytotoxicity was calculated by comparing the remaining cell-associated GFP fluorescence of adherent tumor cells cultured with neutrophils to control wells (tumor cells without neutrophils).

In FIGS. 8A and 8B, five million human BM neutrophils (BMN) were intratumorally injected into established human lung cancer cell line-derived tumors (A549 lung cancer xenografts) in NSG mice. One and four days later, tumors were harvested, enzymatically digested and the presence of neutrophils in xenografts was detected by flow cytometry (boxes in upper right of plots in FIG. 8B).

FIGS. 11A-11O are a series of graphs and images showing a subset of TANs with hybrid characteristics of neutrophils and APCs. FIG. 11A is a photograph of an excised lung showing the location of tumor and distant adjacent tissues used for experiments, as well as dot plots representing the frequency of live $CD11b^+CD15^{hi}$ $CD66b^+$ TANs (inset boxes) in digested tumor tissue. FIGS. 11B-11F show the expression of HLA-DR (FIG. 11B), CD14 (FIG. 11C), CD86 (FIG. 11D), CCR7 (FIG. 11E), and CD206 (FIG. 11F) on gated $CD11b^+CD15^{hi}CD66b^+$TANs (tumor), distant lung neutrophils (distant), and PBNs (PB). Top panels show summary of all patient data. Data are presented as the percentage of cells among all TANs. Error bars represent mean±SEM, 1-way ANOVA with Tukey's multiple comparison test. Bottom panels show representative dot plots. TANs were defined in (FIG. 11A) as live $D11b^+$ $CD15^{hi}CD66b^+$ cells.

FIG. 11G shows the presence of APC-like hybrid neutrophils in the regional lymph nodes (LNs) of lung cancer patients. LNs were mashed through the cell strainer and single cell suspension was stained for indicated markers. Cells were gated on live $CD11b^+CD15^{hi}$ (black box) and further analyzed for the expression of CD66b, CD14, and HLA-DR. Representative dot plots are shown. The error bars represent the mean±SEM, n=10. FIG. 11H shows the frequency of live APC-like hybrid TANs among all nucleated cells in (tumor), distant lung (distant) and peripheral blood (PB). Cumulative results from 50 independent experiments are shown in the scatter plots. The error bars represent the mean±SEM. Statistical analyses were performed with repeated measures one-way ANOVA with Tukey's multiple comparison test. FIGS. 11I-11L show the frequency of APC-like hybrid TANs in patients with NSCLC with different tumor type (FIG. 11I) (AD-adenocarcinoma, SCC-squamous cell carcinoma), stage (FIG. 11J), smoking history (FIG. 11K) and size (FIG. 11L). The error bars represent the mean±SEM, unpaired t test for FIG. 11I and FIG. 11J, Kruskal-Wallis multiple comparison test for FIG. 11K, non-parametric Spearman correlation for FIG. 11L. FIG. 11M shows phagocytic activity of hybrid and canonical TANs. TANs were isolated from tumor and incubated with pHrodo™ Red *E. coli* BioParticles® for 45 min to allow phagocytosis (internalized particles become fluorescent [red]). The level of phagocytosis was measured in gated $HLA\text{-}DR^-$ canonical (grey line) and $HLA\text{-}DR^+$ hybrid TANs (black line). Representative results of 1 of 4 experiments are shown. FIGS. 11N-11O show the gating strategy for sorting of canonical $HLA\text{-}DR^-$ and hybrid $HLA\text{-}DR^+$TANs by flow cytometry. A single cell suspension was obtained from freshly harvested tumor, stained for indicated markers and sorted based on the phenotype of canonical ($CD11b^+$ $CD66b^+CD15^{hi}\text{-}HLA\text{-}DR^-$) and hybrid ($CD11b^+CD66b^+$ $CD15^{hi}HLA\text{-}DR^+$) TANs.

FIG. 12 is a table showing characteristics of the patients taking part in the study (n=109).

FIG. 13A shows a single-cell suspension was obtained from fresh tumor and the expression of the indicated granulocytic markers was analyzed by flow cytometry on gated live CD11b cells. Total TANs are shown in inset boxes. FIG. 13B shows flow cytometric analysis of the expression of APC markers on gated $CD11b^+$ $CD15^{hi}CD66b^+$ TANs. The representative cytomorphology of canonical (lower left inset boxes) and APC-like hybrid TANs (upper right inset boxes) in NSCLC. Scale bar, 10 μm. FIG. 13C shows the presence of APC-like hybrid TANs in tumor detected by immunohistochemistry and immunofluorescence double staining. Scale bar, 50 μm (left image) and 10 μm (other images). FIG. 13D shows the frequency of APC-like hybrid neutrophils in tumors, distant lung tissue, and peripheral blood (PB) (right graph) and in tumors of different sizes (left graph) (line represents mean±SEM, n=50, one-way ANOVA test and unpaired t test). APC-like hybrid TANs were defined as live HLA-$DR^+CD11b^+$ $CD15^{hi}CD66b^+$ cells. FIG. 13E shows intracellular TNF-α and IL-12 production by HLA-$DR^+$ hybrid or HLA-$DR^-$ canonical TANs after stimulation with LPS. TANs were gated on $CD11b^+CD15^{hi}CD66b^+$ cells. Representative results from one of five experiments are shown. FIG. 13F shows the proliferation of autologous CFSE-labeled PBMC stimulated with plate-bound anti-CD3 Abs in the presence of hybrid HLA-$DR^+$ or canonical HLA-$DR^-$ TANs. T cell stimulatory activity was defined as the ratio $CFSE^{lo}$ (T cells+TANs)/$CFSE^{lo}$ (T cells) (n=6, Wilcoxon matched-pairs rank test). FIG. 13G shows autologous virus-specific memory T cell responses in the presence of APC-like hybrid HLA-$DR^+$ or canonical HLA-$DR^-$ TANs. IFN-γ-ELISPOT assay (mean±SEM, n=3, *p≤0.01 canonical versus hybrid, Mann-Whitney test).

FIG. 14A shows fixable viability dye eFluor 660 (FVD660) was used to discriminate viable neutrophils in cell culture. Representative dot plots from one of six experiments are shown. FIG. 14B shows flow cytometric analysis of the expression of MPO, CD66b, and CD15 markers on freshly isolated BMNs (day 0) and BMNs cultured with (HLA-$DR^+$ BMNs) or without hybrid-inducing TCM (HLA-$DR^-$ BMNs) for 7 days. Cytospins show the cytomorphology of these BMNs. Scale bar, 10 μm. FIG. 14C shows survival of BMNs in cell culture in the presence or absence of TCM. Viability dye FVD 660 was used to discriminate viable BMNs in cell culture (mean±SEM, n=6, *p≤0.01, Wilcoxon matched-pairs rank test). FIGS. 14D-14F show flow cytometric analysis of the expression of indicated APC markers on BM-derived hybrid neutrophils (FIG. 14D) (inset boxes), dendritic cells (FIG. 14E), and macrophages (FIG. 14F). Expression of APC markers was analyzed by flow cytometry on gated $CD11b^+$ $CD15^{hi}CD66b^+$ BMNs.

FIG. 15A shows flow cytometric analysis of the expression of CD15, CD66b, CD11b, intracellular MPO, NE and Arg1 on freshly isolated BMNs. Representative dot plots of 1 of 8 experiments are shown. FIG. 15B shows BMN survival in vitro. BMNs were incubated with or without hybrid-inducing TCM. Seven days later, BMNs were stained with viability dye FVD 660 followed by staining for AnnexinV and analyzed by flow cytometry. The error bars represent the mean±SEM, Wilcoxon matched-pairs rank test, n=4. FIG. 15C shows BMNs were isolated from three different cancer patients and treated with the same hybrid-inducing TCM collected from patient #78. The expression of HLA-$DR^+$ and $CD14^+$ was measured on gated live $CD11b^+CD66b^+CD15^{hi}$ BMNs by flow cytometry. FIG. 15D shows kinetics of indicated APC marker expression in BMNs treated with hybrid-inducing TCM. The expressions of indicated markers were assessed by flow cytometry on live $CD11b^+CD66b^+CD15^{hi}$ BMNs for different time points. Results represent 1 of 7 similar experiments. FIG. 15E shows comparative analysis of IRF8 expression (presented as Mean Fluorescence Intensity (MFI) histograms) in non-treated BMNs (BMNs none) and BM-derived hybrid neutrophils differentiated with IFN-γ and GM-CSF (BMNs IFN-γ+GM-CSF) or TCM (BMNs TCM). BMNs neutrophils treated with M-CSF and GMCSF/IL-4 were used as negative control whereas BM-derived macrophages (Mph) and dendritic cells (DC) were used as positive control. Representative dot plots from 1 of 6 experiments are shown. FIG. 15F shows proliferation of HLA-$DR^-$ and HLA-$DR^+$ BMNs in vitro in the presence of hybrid-inducing TCM. BMNs were exposed to hybrid inducing TCM for 8 days. One, five and eight days later, the proliferation of neutrophils was assessed by intracellular staining of incorporated BrdU into DNA of HLA-$DR^-$ and HLA-$DR^+$ BMNs. The expression of HLA-DR was measured on gated live $CD11b^+$ $CD66b^+CD15^{hi}$ BMNs. Representative results from 1 of 3 experiments are shown.

FIG. 16A shows flow cytometric analysis of CD14 and HLA-DR expression on gated live $CD11b^+$ $CD15^{hi}CD66b^+$ BMNs cultured in the presence of hybrid-inducing TCM under normoxic and hypoxic cell culture conditions. FIG. 16B shows flow cytometric analysis of CD14 and HLA-DR expression on gated live $CD11b^+$ $CD15^{hi}CD66b^+$ BMNs cultured in the presence of different TCMs (upper panel) or with IFN-γ and/or GM-CSF (lower panel). FIG. 16C shows the effect of IFN-γ and GM-CSF blocking Abs (5 μg/ml) in blunting the formation of HLA-$DR^+CD14^+$ hybrid neutrophils in vitro (onset box). FIG. 16D shows the expression of CD14 and HLA-DR markers on live $CD11b^+CD15^{hi}CD66b^+$ BMNs (upper panel) and PD-L1 on gated HLA-$DR^+CD14^+$ hybrid neutrophils (lower panel) differentiated with GM-CSF (50 pg/ml) and increasing doses of IFN-γ in vitro. FIGS. 16E-16F show levels of IFN-γ (FIG. 16E) and GM-CSF (FIG. 16F) in supernatants collected from the cell culture of small-sized tumor digests where APC-like hybrid TANs were or were not previously detected (set-off was >10% among all TANs) (line represents mean±SEM, n=10, Mann-Whitney test for unpaired data). Lower panels represent the correlation between the absolute levels of IFN-γ and GM-CSF in the TCM, with the frequency of hybrid neutrophils in each tumor shown in the upper graphs. Non-parametric Spearman test was used to determine the degree of correlation. Representative dot plots from one of five experiments are shown in (FIG. 16A-16D).

FIG. 17A shows flow cytometric analysis of the expression of CD14 and HLA-DR markers on gated live $CD11b^+CD66b^+CD15^{hi}$ BMNs differentiated in the presence of IFN-γ (50 pg/ml) and GM-CSF (50 pg/ml) for 5 days. BMNs isolated from five different lung cancer patients are shown. FIG. 17B shows the effect of TCMs with different concentration of GM-CSF and IFN-γ on the formation of hybrid HLA-$DR^+CD14^+$BMNs. BMNs were isolated from one cancer patient and treated with hybrid-inducing TCM collected from different patients (#58, #78, #41, #101). The expression of HLA-DR and CD14 was measured on gated live $CD11b^+CD66b^+CD15^{hi}$ BMNs. Concentration of GM-CSF and IFN-γ in TCMs was quantified by ELISA.

FIG. 18A shows flow cytometric analysis of the expression of CD10 and CD16 on gated live $CD11b^+CD15^{hi}CD66b^+$ neutrophils isolated from peripheral blood (PBNs) and bone marrow (BMNs) of cancer patients. FIG. 18B shows cytospins were made from sorted BMNs at different stages of maturation and stained with the Hema3 Stat Pack Kit (Wright-Giemsa-like stain). FIG. 18C shows sorted BMNs at different stages of maturation were differentiated in the presence of IFN-γ (50 pg/ml) and GM-CSF (50 pg/ml) in vitro. Expression of HLA-DR and CD14 markers was analyzed by flow cytometry on $CD11b^+CD15^{hi}CD66b^+$BMNs. FIG. 18D shows cytomorphology of APC-like $HLA-DR^+$ hybrid neutrophils differentiated from the sorted populations of BMNs at different stages of maturation. Representative results from one of four experiments are shown in (FIG. 18A-18D). Scale bar, 10 μm.

FIG. 19A shows the co-expression of CD15, CD66b, CD11b, CD16 and CD10 analyzed by flow cytometry on freshly isolated BMNs. Representative dot plots from 1 of 5 experiments are shown. FIG. 19B is a schematic representation of the phenotype and nuclear morphology of $CD11b^+CD15^{hi}$ BMNs at different stages of development. BMNs at different stages of maturation were isolated by flow cytometry sorting and analyzed for the indicated surface markers by flow cytometry. Cytospins were made from sorted BMNs and stained with the Hema3 Stat Pack Kit (Wright-Giemsa-like stain). FIG. 19C shows the formation of hybrid $HLA-DR^+$ $CD14^+$ neutrophils from G-CSF mobilized low density immature PBNs. The expression of HLA-DR and CD14 was measured on gated live $CD11b^+CD66b^+CD15^{hi}$ PBNs after the treatment with hybrid-inducing TCM or IFN-γ (50 pg/ml) and GM-CSF (50 pg/ml). Representative dot plots from 1 of 4 similar experiments are shown.

FIG. 20A shows flow cytometric analysis of the level of Ikaros and HLA-DR expression in PBNs and BMNs at different stages of maturation. Results are shown as mean fluorescence intensity (MFI). FIG. 20B shows flow cytometric analysis of the level of Ikaros expression in the $HLA-DR^+$ hybrid and $HLA-DR^-$ canonical $CD11b^+CD15^{hi}CD66b^+$ BMNs. FIG. 20C shows flow cytometric analysis of CD14 and HLA-DR expression on gated live $CD11b^+CD15^{hi}CD66b^+$ BMNs cultured in the presence of lenalidomide (10 mM) and hybrid-inducing TCM (30% v/v) for 6 days. FIG. 20D shows the effect of IFN-γ (50 pg/ml) and GM-CSF (50 pg/ml) on the formation of $HLA-DR^+CD14^+$ hybrid neutrophils in the absence (upper panel) or presence (lower panel) of lenalidomide (10 mM) in vitro. The level of Ikaros expression (MFI) in BMNs treated with IFN-g (50 pg/ml) and GM-CSF (50 pg/ml) for 5 days is shown (mean±SEM, n=3, *p≤0.01, Wilcoxon matched-pairs rank test). Representative dot plots from one of six experiments are shown in (FIGS. 20A-20D).

FIG. 21A shows development of hybrid and canonical neutrophils. To obtain hybrid $HLA-DR^+CD14^+$ neutrophils (top panel), BMNs were treated with hybrid-inducing TCM collected from tumor digests where the frequency of hybrid TANs was markedly elevated. To obtain canonical $HLA-DR-CD14^-$ neutrophils (bottom panel), BMNs were treated with TCM collected from tumor digests where hybrid TANs were not detected. The expression of CD62L, CD54, HLA-DR and CD14 was measured by flow cytometry on gated live $CD11b^+CD66b^+CD15^{hi}$ cells. Representative dot plots from 1 of 12 experiments are shown. FIG. 21B shows expression of the CD25, and CD69 markers on activated autologous T cells co-incubated with BM-derived canonical and hybrid neutrophils. T cells were isolated from PBMC, stimulated with plate-bound anti-CD3 Abs and incubated with BM-derived neutrophils at a 1:1 ratio for 24 hours. Error bars represent mean±SEM from 6 independent experiments (Wilcoxon matched-pairs rank test). FIG. 21C shows the ability of hybrid $HLA-DR^+$ or canonical $HLA-DR^-$ BMNs to stimulate autologous virus-specific memory T cell response in an IFN-γ ELISPOT assay. Autologous T cells were isolated from PBMC and co-cultured with BM-derived canonical HLA-DR− and hybrid $HLA-DR^+$ neutrophils that had been pulsed with a mixture of viral T cell epitopes for 2 hours. The number of IFN-γ-producing T cells was determined in three independent ELISpot assays. Error bars represent mean±SEM from 3 independent experiments (*p≤0.01, Mann-Whitney test). FIG. 21D shows flow cytometric analysis of IFN-γ production by Ly95 T cells stimulated with A2/NY-ESO A549 tumor cells in the presence of hybrid $HLA-DR^+$ BMNs using a transwell system. Activated Ly95 T cells were mixed with $HLA-DR^+$ BMNs at a 1:1 ratio (mix). To separate T cells and BMNs, activated T cells were cultured in the bottom chamber and $HLA-DR^+$ BMNs were placed in the top chamber of the 24-well flat-bottom transwell culture plate (TW). Representative results from 1 of 3 experiments are shown.

FIG. 22A shows the proliferation and IFN-γ production of anti-CD3 Ab stimulated autologous T cells in the presence of BM-derived canonical and hybrid neutrophils differentiated with hybrid-inducing TCM or IFN-γ (50 pg/ml) and GM-CSF (50 pg/ml). FIG. 22B shows summary results of autologous T cell proliferation (upper graph) and IFN-γ production (lower graph) in the presence of canonical and hybrid neutrophils. Data are presented as a ratio (CD3 $cells+CD15^{hi}$)/(CD3) (n=8, Wilcoxon matched-pairs rank test). FIG. 22C shows the proliferation of CFSE-labeled autologous PBMCs cultured with hybrid BMNs with different level of PD-L1 expression in the presence (lower panel) or absence PD-L1 blocking Abs (5 mg/ml) (upper panel). $PD-L1^{-/lo/hi}$ $HLA-DR^+$ hybrid neutrophils were differentiated with GM-CSF (50 pg/ml) and increasing doses of IFN-γ. FIG. 22D shows the proliferation of allogeneic T cells from healthy donors in the presence of APC-like hybrid neutrophils in a mixed-lymphocyte reaction. Representative results from one of six experiments are shown in FIGS. 22C-22D.

FIG. 23A shows NY-ESO-specific Ly95 cells (TCR $Vp13.1^+CD8^+$) were stimulated with A549 tumor cell line expressing NY-ESO-1 in the context of HLA-A*02 (A2/NY-ESO-1 A549) in the presence of BM-derived canonical and hybrid neutrophils. Intracellular IFN-γ and Granzyme B production was measured by flow cytometry. FIG. 23B shows cumulative results of the Ly95 cell stimulatory activity of canonical and hybrid neutrophils. Stimulatory activity was defined as a ratio (Ly95 cells+A549-N-ESO+BMN)/(Ly95 cells+A549-NY-ESO) (n=6, Wilcoxon matched-pairs rank test). FIG. 23C shows $HLA-A02^+$ canonical or hybrid neutrophils were pulsed with synthetic NY-ESO-1 peptide and co-cultured with Ly95 cells for 24 hr. Intracellular IFN-γ was assessed by flow cytometry (mean±SEM, n=6, *p≤0.01, Wilcoxon matched-pairs rank test). FIG. 23D shows DQ-OVA uptake and processing by BM-derived canonical or hybrid neutrophils (open histograms). Cells incubated at 4° C. served as controls (shaded histograms). FIG. 23E shwos cross-presentation of NY-ESO-1 epitopes to Ly95 cells by HLA-A02$^+$ canonical or hybrid neutrophils preloaded with NY-ESO-1 protein, NY-ESO-1 peptide, or NY-ESO-immune complex (IC). IFN-γ ELISpot (mean±SEM, n=6, *p % 0.01 canonical versus hybrid, Wilcoxon matched-pairs rank test).

DETAILED DESCRIPTION OF THE INVENTION

Definitions

Figures 1A, 1B, 1C:
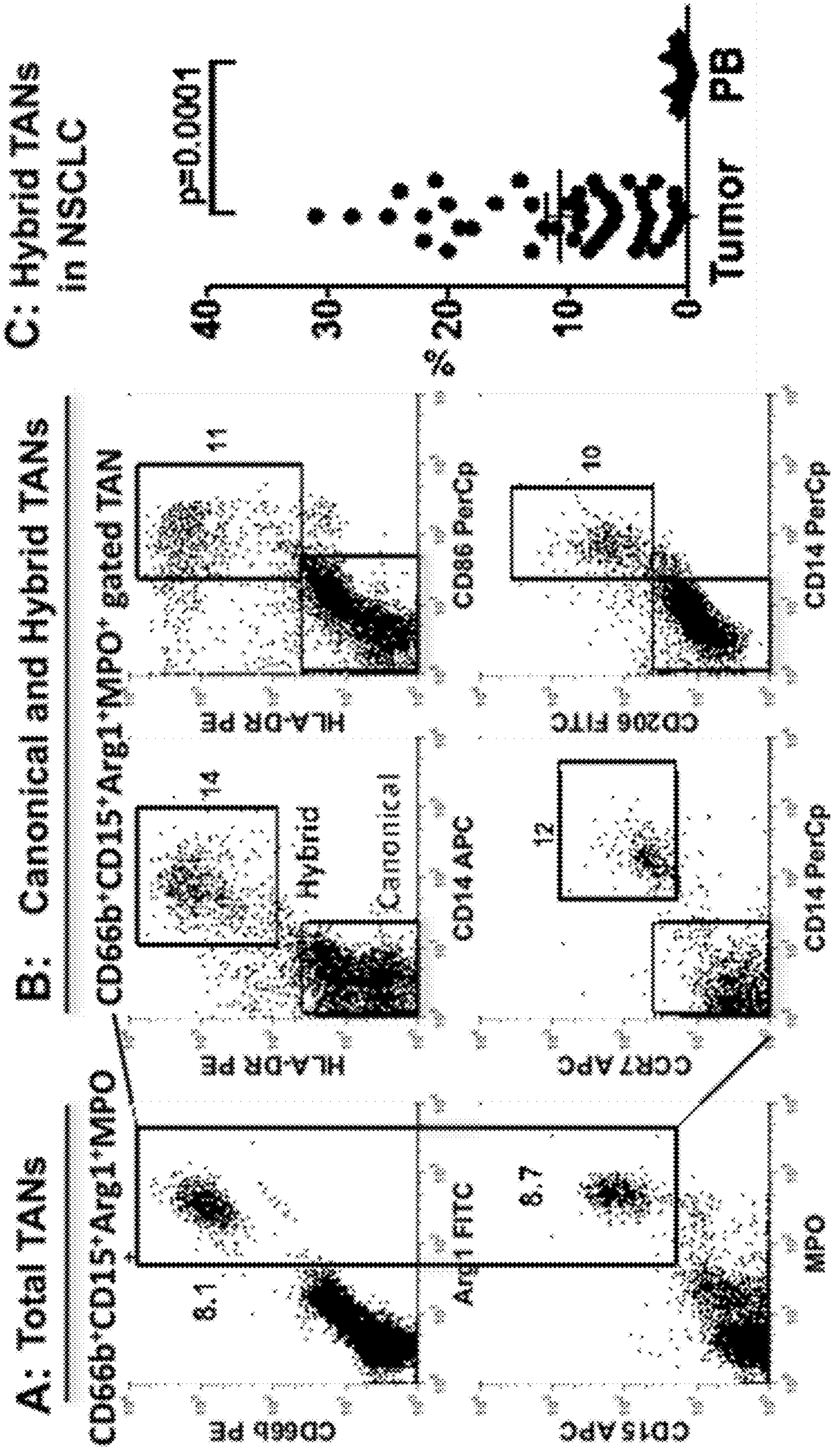
FIGS. 1A-1C are a series of plots showing tumor-associated neutrophil (TAN) subsets in lung cancer. A single cell suspension was obtained from freshly harvested tumor tissues and stained for indicated markers. TANs were gated on live single $CD11b^{+}CD15^{hi}CD66b^{+}Arg1^{+}$ cells (FIG. 1A, long box) and further analyzed for the expression of HLA-DR, CD14, CD86, CCR7, and CD206 by flow cytometry (FIG. 1B, boxes in upper right of each plot).

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or within 10%, 9%, 8%, 7%, 6%, 5%, 4%, 3%, 2%, 1%, 0.5%, 0.1%, 0.05%, or 0.01% of the specified value, as such variations are appropriate to perform the disclosed methods. Unless otherwise clear from context, all numerical values provided herein are modified by the term about.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By "agent" is meant any small molecule chemical compound, antibody, nucleic acid molecule, or polypeptide, or fragments thereof. In some embodiments, contacting immature neutrophils or immature CD15-positive cells with an agent stimulate generation of hybrid neutrophils from these cells. The stimulating agent, for example, may be INF-γ, GM-CSF, lenalidomide, or an analog thereof.

As used herein, to "alleviate" a disease, disorder or condition means reducing the severity of one or more symptoms of the disease, disorder or condition.

By "analog" is meant a molecule that is not identical, but has analogous functional or structural features.

The terms "binding," "bind," "bound" refer to an interaction between two molecules. The interaction may include a covalent or non-covalent bond. The interaction may also be reversible or irreversible depending on the type of interaction, such as covalent bond formation.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. Tetramers may be naturally occurring or reconstructed from single chain antibodies or antibody fragments. Antibodies also include dimers that may be naturally occurring or constructed from single chain antibodies or antibody fragments. The antibodies in the present invention may exist in a variety of forms including, for example, polyclonal antibodies, monoclonal antibodies, Fv, Fab and F(ab') 2, as well as single chain antibodies (scFv), humanized antibodies, and human antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab') 2, and Fv fragments, linear antibodies, scFv antibodies, single-domain antibodies, such as camelid antibodies (Riechmann, 1999, Journal of Immunological Methods 231:25-38), composed of either a VL or a VH domain which exhibit sufficient affinity for the target, and multispecific antibodies formed from antibody fragments. The antibody fragment also includes a human antibody or a humanized antibody or a portion of a human antibody or a humanized antibody.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. k and l light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a “gene” at all. It is readily apparent that an antigen can be generated synthesized or can be derived from a biological sample. Such a biological sample can include, but is not limited to a tissue sample, a tumor sample, a cell or a biological fluid.

By “anti-tumor antibody” or “therapeutic anti-tumor antibody” is meant an antibody specifically binding to a tumor antigen. Binding of the antibody to the tumor may effect an immune response against the tumor. In some embodiments, hybrid neutrophils of the invention increase efficacy of anti-tumor antibodies by increasing antibody-dependent cellular cytoxicity (ADCC), antibody-dependent phagocytosis (ADP), and/or effector T cell response. Examples of anti-tumor antibodies include, without limitation, anti-Her2/neu antibody, rituximab, necitumumab, panitumumab, and cetuximab.

The term “anti-tumor effect” as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An “anti-tumor effect” can also be manifested by the ability of the peptides, polynucleotides, cells and antibodies of the invention in prevention of the occurrence of tumor in the first place.

As used herein, the term “autologous” is meant to refer to any material derived from the same individual to which it is later to be re-introduced into the individual.

“Allogeneic” refers to a graft derived from a different animal of the same species.

“Xenogeneic” refers to a graft derived from an animal of a different species.

By “antibody dependent cellular cytotoxicity” or “ADCC” is meant a process whereby an effector cell lyses a target cell, wherein the target cell is bound by antibodies recognizing antigens on the surface of the target cell. By “antibody dependent phagocytosis” or ADP is meant a process whereby a phagocytic cell (e.g., a neutrophil) engulfs or phagocytoses a target cell, wherein the target cell is bound by antibodies recognizing antigens on the surface of the target cell. In some embodiments, hybrid neutrophils of the invention increase effectiveness of ADCC and/or ADP in a subject, particularly a subject having a tumor treated with anti-tumor therapeutic antibodies (e.g., cetuximab). Without being bound by theory, it is believed the hybrid neutrophils may increase ADCC and/or ADP through Fc receptors (e.g., CD16, CD32, CD64 and CD89) expressed by the hybrid neutrophils, enabling them to recognize and bind to Fc portions of the antibodies bound to tumor cells and thereby phagocytose and/or lyse the tumor cells. By an “increase” or “enhancement” in ADCC and/or ADP is meant an increase in the amount or frequency of these processes in a subject under one condition relative to the amount or frequency of ADCC and/or ADP processes in the subject in another condition (e.g. a control condition such as an untreated subject or the subject treated only with anti-tumor antibodies and not treated with hybrid neutrophils). An “increase” or “enhancement” in ADCC and/or ADP is expected to result in an increase in anti-tumor effect of anti-tumor antibodies, increased inhibition of tumor cell growth, and/or increased reduction in survival of tumor cells.

The term “cancer” as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In certain embodiments, the cancer is non-small cell lung cancer (NSCLC).

By “effective amount” is meant the amount required to reduce or improve at least one symptom related to the tumor or cancer in a subject The effective amount of an anti-tumor antibody and/or the effective amount of a composition comprising a hybrid neutrophil of the present invention used for therapeutic treatment of a tumor varies depending upon the manner of administration, the age, body weight, and general health of the subject.

By “effector T cell response” is meant the process by which effector T cells (e.g., effector CD8-positive T cells) recognize peptide antigens presented by cell surface molecules (e.g., as MHC class I molecules) expressed by antigen-presenting cells (APCs). When effector T cells are presented with antigen, they become activated and may begin to divide and/or secrete molecules (e.g., cytokines) that regulate or assist in the immune response.

Without being bound by theory, it is believed the hybrid neutrophils may increase effector T cell response through their APC-like characteristics (e.g., expression of MHC class I molecules). This enables hybrid neutrophils to present antigens to effector T cells such as CD8-positive T cells, thereby stimulating an effector T cell response. By an “increase” or “enhancement” in effector T cell response is meant an increase in the amount or frequency of these effector T cell response processes in a subject under one condition relative to the amount or frequency of these processes in the subject in another condition (e.g. a control condition such as an untreated subject or the subject treated only with anti-tumor antibodies and not treated with hybrid neutrophils). An “increase” or “enhancement” in effector T cell response is expected to result in an increase in anti-tumor effect of anti-tumor antibodies, increased inhibition of tumor cell growth, and/or increased reduction in survival of tumor cells.

As used herein “endogenous” refers to any material from or produced inside an organism, cell, tissue or system.

As used herein, the term “exogenous” refers to any material introduced from or produced outside an organism, cell, tissue or system.

The term “expression” as used herein is defined as the transcription and/or translation of a particular nucleotide sequence driven by its promoter. In some embodiments, “expression” may refer to display of a polypeptide product of the transcription and/or translation of the nucleotide on the surface of a cell. Such polypeptides may be referred to as “cell surface markers” or “cell surface molecules.”

Different cell types (e.g., T cells, antigen-presenting cells, or neutrophils) express molecules unique to the cell type. Thus, these “cell molecules” typically serve as markers of specific cell types. For example, a “neutrophil associated molecule” or “neutrophil associated cell molecule” includes, without limitation, Arg1, MPO, CD66b, and CD15. An “antigen-presenting cell (APC) associated molecule” or “antigen-presenting cell (APC) associated cell molecule” includes, without limitation, CD14, HLA-DR, CD32, and CD64.

Cells of the invention may be characterized by expression of cell molecules. A cell type expressing a cell molecule may be classified as “positive” for the cell molecule. For example, a neutrophil is Arg1-positive ($Arg1^+$). Conversely, a cell type that does not express a cell molecule may be classified as "negative" for the cell molecule. Levels of expression of a cell molecule may low, intermediate ("int"), or high ("hi"). For example, neutrophils are $CD15^{hi}$ (i.e., express high levels of CD15). Expression of cell molecules may be detected by any method known to one of skill in the art (e.g., immunoassays using antibodies against cell molecules).

As used herein, the term "fragment," as applied to a nucleic acid, refers to a subsequence of a larger nucleic acid. A "fragment" of a nucleic acid can be at least about 15 nucleotides in length; for example, at least about 50 nucleotides to about 100 nucleotides; at least about 100 to about 500 nucleotides, at least about 500 to about 1000 nucleotides; at least about 1000 nucleotides to about 1500 nucleotides; about 1500 nucleotides to about 2500 nucleotides; or about 2500 nucleotides (and any integer value in between).

As used herein, the term "fragment," as applied to a protein or peptide, refers to a subsequence of a larger protein or peptide. A "fragment" of a protein or peptide can be at least about 20 amino acids in length; for example, at least about 50 amino acids in length; at least about 100 amino acids in length; at least about 200 amino acids in length; at least about 300 amino acids in length; or at least about 400 amino acids in length (and any integer value in between).

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence that differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions.

By "granulocyte colony stimulating factor" or "G-CSF" is meant a glycoprotein having growth factor activity and immunomodulatory activities. G-CSF may stimulate bone marrow to produce to produce granulocytes such as neutrophils, and may promote proliferation and differentiation of neutrophil precursors. In some embodiments, peripheral blood immature neutrophils are mobilized in peripheral blood by contacting peripheral blood with G-CSF and/or other agents.

By "granulocyte macrophage colony stimulating factor" or "GM-CSF" is meant a glycoprotein having growth factor activity and immunomodulatory activities. In particular, GM-CSF may stimulate stem cells to produce granulocytes such as neutrophils. In some embodiments, compositions comprising immature bone marrow CD15-positive cells or peripheral blood immature neutrophils are contacted with GM-CSF and/or other agents to stimulate generation of hybrid neutrophils.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

As applied to a protein sequence, "homology" as used herein refers to a protein sequence that has about 50% sequence similarity. More preferably, the sequence has about 75% sequence similarity, even more preferably, has at least about 80%, 85%, 90%, 91%, 92%, 93%, 94%, 95%, 96%, 97%, 98%, 99% sequence similarity.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent that two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical. As applied to nucleic acid sequences, "identity" as used herein refers to a sequence that has about 50% sequence identity. More preferably, the homologous sequence has about 75% sequence identity, even more preferably, has at least about 80%, 85%, 90%, 91%, 92%, 93%, 94%, 95%, 96%, 97%, 98%, 99% sequence identity.

As used herein, an "instructional material" includes a publication, a recording, a diagram, or any other medium of expression that can be used to communicate the usefulness of the compositions and methods of the invention. The instructional material of the kit of the invention may, for example, be affixed to a container that contains the nucleic acid, peptide, and/or composition of the invention or be shipped together with a container that contains the nucleic acid, peptide, and/or composition. Alternatively, the instructional material may be shipped separately from the container with the intention that the instructional material and the compound be used cooperatively by the recipient.

By "interferon gamma," "interferon-γ," or "IFN-γ" is meant a cytokine belonging to the type II class of interferons. IFN-γ has antiviral activity and immunoregulatory functions, such as activation of macrophages. In some embodiments, compositions comprising immature bone marrow CD15-positive cells or peripheral blood immature neutrophils are contacted with IFN-γ and/or other agents to stimulate generation of hybrid neutrophils.

The terms "isolated," "purified," or "biologically pure" refer to material that is free to varying degrees from components which normally accompany it as found in its native state. "Isolate" denotes a degree of separation from original source or surroundings. For example, in some embodiments, a hybrid neutrophil is isolated from tumor tissues in a cancer patient. In some other embodiments, immature CD15-positive cells are isolated from bone marrow. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. "Purified" can also refer to a molecule separated after a bioconjugation technique from those molecules which were not efficiently conjugated.

An "isolated nucleic acid" refers to a nucleic acid segment or fragment that has been separated from sequences that flank it in a naturally occurring state, e.g., a DNA fragment that has been removed from the sequences that are normally adjacent to the fragment, e.g., the sequences adjacent to the fragment in a is genome that it naturally occurs. The term also applies to nucleic acids that have been substantially purified from other components that naturally accompany the nucleic acid, e.g., RNA or DNA or proteins, that naturally accompany it in the cell. The term therefore includes, for example, a recombinant DNA that is incorporated into a vector, into an autonomously replicating plasmid or virus, or into the genomic DNA of a prokaryote or eukaryote, or that exists as a separate molecule (e.g., as a cDNA or a genomic or cDNA fragment produced by PCR or restriction enzyme digestion) independent of other sequences. It also includes a recombinant DNA that is part of a hybrid gene encoding additional polypeptide sequence.

A "neutrophil" is a type of leukocyte which constitutes about 50% to 80% of all leukocytes in the human body. Neutrophils are generated from precursor cells in the bone marrow and have phagocytic activity. Neutrophils display the cell surface markers Arg1, MPO, CD66b, and CD15. Neutrophils may also infiltrate a tumor microenvironment and mediate processes associated with tumor progression. Such neutrophils are "tumor-associated neutrophils" or "TANs." Tumor-recruited myeloid cells represent a significant portion of inflammatory cells in the tumor microenvironment and influence nearly all steps of tumor progression. Among these myeloid cells, tumor-associated neutrophils (TANs) are present in large numbers. The majority of TANs expressed classic neutrophil markers ("canonical TANs").

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron (s).

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) that "U" replaces "T."

"Pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutical composition" or "pharmaceutically acceptable composition" refers to a mixture of at least one compound or molecule or cell useful within the invention with a pharmaceutically acceptable carrier. The pharmaceutical composition facilitates administration of the compound or molecule or cell to a patient. Multiple techniques of administering a compound or molecule exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound, molecule, or cell useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound or molecule useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences that are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, that there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

As used herein, "sample" or "biological sample" refers to anything, which may contain the cells of interest (e.g., immature granulocytes). The sample may be a biological sample, such as a biological fluid or a biological tissue. In one embodiment, a biological sample is a tissue sample including pulmonary arterial endothelial cells. Such a sample may include diverse cells, proteins, and genetic material. Examples of biological tissues also include organs, tumors, lymph nodes, arteries and individual cell(s). Examples of biological fluids include urine, blood, plasma, serum, saliva, semen, stool, sputum, cerebral spinal fluid, tears, mucus, amniotic fluid or the like. In some embodiments, the biological sample is blood. In some other embodiments, the biological sample is bone marrow.

By the term "specifically binds," as used herein, is meant a compound, e.g., a protein, a nucleic acid, an antibody, and the like, which recognizes and binds a specific molecule, but does not substantially recognize or bind other molecules in a sample.

The term "subject" is intended to include living organisms that an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell that has been separated from other cell types that it is normally associated in its naturally occurring state. In some instances, a population of substantially purified cells refers to a homogenous population of cells. In other instances, this term refers simply to cell that have been separated from the cells that they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

As used herein, a "therapeutic agent" is a molecule or atom that is useful for therapy. Examples of therapeutic agents include drugs, toxins, enzymes, hormones, cytokines, immunomodulators, anti-tumor agents, chemotherapeutic agents, anti-cell proliferation agents, boron compounds, and therapeutic radioisotopes.

The term "transfected" or "transformed" or "transduced" as used herein refers to a process that exogenous nucleic acid is transferred or introduced into the host cell. A "transfected" or "transformed" or "transduced" cell is one that has been transfected, transformed or transduced with exogenous nucleic acid. The cell includes the primary subject cell and its progeny.

As used herein, the terms "treat," treating," "treatment," and the like refer to reducing or improving a disorder and/or symptom associated therewith. It will be appreciated that, although not precluded, treating a disorder or condition does not require that the disorder, condition or symptoms associated therewith be completely ameliorated or eliminated.

By "tumor conditioned medium" or "TCM" is meant a medium obtained by collecting medium from a digested tumor, wherein the tumor that was digested contained populations of tumor-associated neutrophils exhibiting the hybrid neutrophil phenotype (i.e., positive for Arg1, MPO, CD66b, and CD15 and positive for CD14, HLA-DR, CD32, CD64, and CD89).

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The recitation of an embodiment for a variable or aspect herein includes that embodiment as any single embodiment or in combination with any other embodiments or portions thereof. Any compositions or methods provided herein can be combined with one or more of any of the other compositions and methods provided herein.

Composition and Methods of the Invention

The present invention relates to compositions and methods that include novel anti-tumor therapies for cancer. The invention is based, at least in part, on the discovery of a novel subset of tumor-associated neutrophils exhibiting composite characteristics of neutrophils and antigen-presenting cells. Described herein are studies demonstrating that hybrid $CD14^+HLA\text{-}DR^+CD32^{hi}CD64^{hi}$ neutrophils can be generated from bone marrow or peripheral blood immature granulocytes. These differentiated cells efficiently phagocytose bacteria, mediate a high level of antibody dependent phagocytosis and stimulate the effector T cell responses in vitro. These abilities of hybrid neutrophils provide new opportunities to boost anti-tumor and anti-infectious immunity.

Hybrid Neutrophils

Neutrophils are a type of leukocyte and constitute about 50% to 80% of all leukocytes in the human body. Neutrophils are generated from precursor cells in the bone marrow. Within the body, neutrophils migrate to areas of infection or tissue injury. Neutrophils are antimicrobial effector cells equipped with powerful killing machinery to respond to pathogens. For example, neutrophils are phagocytic and may engulf bacteria or other microorganisms by phagocytosis.

Neutrophils especially target opsonized bacteria or other microorganisms (i.e., bacteria or microorganisms "marked" for destruction by phagocytic cells). Neutrophils may target a microorganism through a process referred to as antibody-dependent cellular cytotoxicity (ADCC). In this process, antibodies bind to antigens on the microorganism's cell membrane. The Fc portion of the antibody is recognized by Fc receptors on neutrophils, thus directing neutrophils to the microorganism.

Without intending to be bound by theory, it is hypothesized that therapeutic antibodies against tumor antigens can direct and activate neutrophils' cytotoxic machinery against opsonized tumors through ADCC. Unfortunately, the clinical efficacy of many therapeutic antibodies is poor and needs to be enhanced (Liu et al., *Cancer Chemother Pharmacol.* 2010 April; 65(5): 849-861; Fury et al., *Cancer Immunol Immunother.* 2008 February; 57(2): 155-163; Repp et al., *Br J Cancer.* 2003 Dec. 15; 89(12): 2234-2243). The identification and administration of efficient effector subsets responsible for mediating sufficient ADCC in humans could lead to the development of more synergistic and combination therapies that would enhance the effect of therapeutic antibodies (which may also include antibodies directed at bacteria or other microorganisms).

In some aspects, the invention described herein features a novel approach to boost anti-tumor and anti-infectious immunity by engaging a newly identified subpopulation of activated neutrophils with the composite characteristics of neutrophils ($Arg1^+MPO^+CD66b^+CD15^{hi}$) and antigen-presenting cells ($CD14^+HLA\text{-}DR^+CD32^{hi}CD64^{hi}$). Heretofore these cells are referred to as "hybrid neutrophils." The unique phenotype of hybrid neutrophils described herein enables them to more efficiently mediate antibody-dependent phagocytosis and stimulate effector T cell responses. In some aspects, the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, and CD64. In certain embodiments, the hybrid neutrophil further expresses at least one molecule selected from the group consisting of: MHC class I, MHC class II, OX40L, 4-1BBL, CD86, CD40, CCR7, and CD89. In certain embodiments, the expression of any one of the molecules is low, intermediate, or high. In other embodiments, the expression of any one of the molecules is increased relative to expression of the molecule on a canonical tumor-associated neutrophil (TAN). In particular embodiments, the hybrid neutrophil expresses CD14, HLA-DR, CD32, CD64, CD89. In still other embodiments, wherein the hybrid neutrophil expresses Arg1, MPO, CD66b, CD15, CD14, HLA-DR, MHC class I, OX40L, 4-1BBL, CD86, CD40, CCR7, CD32, CD64, and CD89. In particular embodiments, the expression of CD32 and/or CD64 and/or CD89 is high.

The development of neutrophils exhibiting dual phenotype and functionality of neutrophils and dendritic cells (DC) has recently been described in mice (Matsushima et al., *Blood.* 2013 Mar. 7; 121(10): 1677-1689; Geng et al., *Blood.* 2013 Mar. 7; 121(10): 1690-1700), where the differentiation of bone marrow cells into DC-neutrophil hybrids has been performed in the presence of GM-CSF. However, the phenotype of hybrid neutrophils differentiated from human bone marrow neutrophils with low concentrations of IFN-γ and GM-CSF is quite different from the phenotype of those described previously. Human BM derived hybrid neutrophils exhibit only partial phenotype of DC (MHC class II, CD86, CCR7); however, they also acquire the partial phenotype of monocyte/macrophages (CD14, CD206, $CD64^{hi}$, $CD32^{hi}$, $CD89^{hi}$). Importantly, it is believed that there is no report of clinical use of human hybrid neutrophils.

In some aspects of the invention, the hybrid neutrophil is in a container comprising at least one non-naturally occurring component. The non-naturally occurring container may be any vessel holding or capable of holding a hybrid neutrophil or composition comprising a hybrid neutrophil. The non-naturally occurring component may be, without limitation, glass, plastic, metal, or a composite material. The non-naturally occurring container may be, without limitation, a tube, capsule, dish, plate, flask, packet, vial, pouch, jar, or bottle.

In certain aspects, the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89. In another aspect, the hybrid neutrophil further expresses at least one molecule selected from the group consisting of: MHC class I, MHC class II, OX40L, 4-1BBL, CD86, CD40, and CCR7. The expression level of any one of the aforementioned molecules can be low, intermediate, or high. In some embodiments, the expression of any one of the molecules is increased relative to the expression of the molecule on a canonical tumor-associated neutrophil (TAN).

In some embodiments, the hybrid neutrophil expresses CD14, HLA-DR, CD32, CD64, and CD89. In some embodiments, the hybrid neutrophil expresses Arg1, MPO, CD66b, CD15, CD14, HLA-DR, MHC class I, OX40L, 4-1BBL, CD86, CD40, CCR7, CD32, CD64, and CD89. In some embodiments, the expression of CD32 and/or CD64 and/or CD89 is high.

Methods of Generating Hybrid Neutrophils

Hybrid neutrophils of the invention have been shown to efficiently phagocytose bacteria, mediate a high level of antibody dependent phagocytosis and stimulate the effector T cell responses in vitro. These properties of hybrid neutrophils provide new opportunities to boost anti-tumor and anti-infectious immunity.

In some aspects of the present invention, the hybrid neutrophils are isolated from a tumor tissue of a cancer patient. Hybrid neutrophils were found in tumor tissues of cancer patients, although the frequency of these newly identified "hybrid" subset of tumor associated neutrophils (TANs) varied widely in the tumor tissues. It was found that these hybrid TANs comprised 0.5-25% of all TANs.

Large numbers of hybrid neutrophils may be difficult to obtain by isolation from tumor tissues. For therapeutic use of hybrid neutrophils, it is desirable to generate large numbers of these cells. Accordingly, provided herein are methods of generating a hybrid neutrophil, particularly in large numbers. The studies described herein demonstrated that hybrid $CD14^{+}HLA\text{-}DR^{+}CD32^{hi}CD64^{hi}CD89^{hi}$ neutrophils could be generated from bone marrow or peripheral blood immature granulocytes. The methods herein feature identified conditions in which bone marrow or peripheral blood immature granulocytes can be differentiated into hybrid neutrophils in large numbers.

In one aspect, the present invention provides a method of generating a hybrid neutrophil, the method comprising contacting a composition comprising a bone marrow (BM) immature CD15-positive (CD15+) cell with an amount of tumor conditioned medium (TMC). In another aspect, the method comprises contacting a composition comprising a bone marrow (BM) immature CD15-positive (CD15+) cell with an amount of interferon g (IFN-γ) and an amount of granulocyte macrophage colony stimulating factor (GM-CSF). In yet another aspect, the method comprises contacting a composition comprising a bone marrow (BM) immature CD15-positive (CD15+) cell with an amount of an agent that reduces the level of Ikaros polypeptide in the cell and an amount of granulocyte macrophage colony stimulating factor (GM-CSF). The agent reducing the level of Ikaros may be lenalidomide, or an analog thereof (e.g., pomalidomide or thalidomide).

In still another aspect, the method comprises contacting a composition comprising peripheral blood immature neutrophils with an amount of tumor conditioned medium (TCM). In yet another aspect, the method comprises contacting a composition comprising peripheral blood immature neutrophils with an amount of interferon γ (IFN-γ) and an amount of granulocyte macrophage colony stimulating factor (GM-CSF). The tumor conditioned medium may be obtained by collecting the medium from a digested tumor where hybrid tumor-associated neutrophils (TANs) were previously detected. The TCM may be added to the composition at about 50% v/v. In various embodiments of any of the above aspects, the peripheral blood immature neutrophils may be mobilized in peripheral blood by contacting peripheral blood with an amount of GM-CSF or G-CSF.

In one aspect, the present invention provides a method of generating a hybrid neutrophil comprising contacting a composition comprising a bone marrow (BM) immature CD15-positive ($CD15^{+}$) cell with an amount of tumor conditioned medium, wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In another aspect, the present invention provides a method of generating a hybrid neutrophil comprising contacting a composition comprising a bone marrow (BM) immature CD15-positive ($CD15^{+}$) cell with an amount of interferon γ (IFN-γ) and an amount of granulocyte macrophage colony stimulating factor (GM-CSF), wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In yet another aspect, the invention provides a method of generating a hybrid neutrophil, comprising contacting a composition comprising a bone marrow (BM) immature CD15-positive ($CD15^{+}$) cell with an amount of an agent that reduces the level of Ikaros polypeptide in the cell and an amount of granulocyte macrophage colony stimulating factor (GM-CSF), wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89. In one embodiment, the agent reduces the level of Ikaros polypeptide in the cell is lenalidomide.

Another aspect of the invention includes a method of generating a hybrid neutrophil comprising contacting a composition comprising peripheral blood immature neutrophils with an amount of tumor conditioned medium, wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89. In certain embodiments, the tumor conditioned medium is about 50% v/v.

Yet another aspect of the invention provides a method of generating a hybrid neutrophil comprising contacting a composition comprising peripheral blood immature neutrophils with an amount of interferon γ (IFN-γ) and an amount of granulocyte macrophage colony stimulating factor (GM-CSF), wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89.

In some embodiments, the INF-γ and/or GM-CSF is added at concentrations of at least about 50 pg/ml, at least about 60 pg/ml, at least about 70 pg/ml, at least about 80 pg/ml, at least about 90 pg/ml, or at least about 100 pg/ml. In particular embodiments, GM-CSF is added at about 100 pg/ml. In particular embodiments, IFN-γ is added at about 100 pg/ml. Lenalidomide may be added at a concentration of about 10 μM.

Bone marrow (BM) immature CD15-positive cells may be obtained from human bone marrow. The bone marrow may be obtained from rib fragments removed from subjects during a surgery. An enriched population of bone marrow neutrophils may be obtained by using an anti-CD15 to isolate the CD15-positive cells. For example, in one embodiment, bone marrow (BM) immature CD15 cells were isolated using anti-CD15 magnetic beads.

Immature granulocytes may also be obtained from peripheral blood after G-CSF or GM-CSF induced mobilization. In addition to bone marrow origin, hybrid neutrophils may be differentiated from peripheral blood immature neutrophils mobilized in peripheral blood by an administration with G-SCF or GM-CSF. Immature neutrophils or immature cells may then be collected and separated by any methods known in the art, such as leukapheresis and/or Fluorescence-Activated Cell Sorting (FACS). In a particular embodiment, low-density immature neutrophils are isolated by gradient separation.

In certain embodiments, peripheral blood immature neutrophils are mobilized in peripheral blood by contacting peripheral blood with an amount of granulocyte macrophage colony stimulating factor (GM-CSF) or an amount of granulocyte colony stimulating factor (G-CSF). In some embodiments, a subject is treated with G-SCF or GM-CSF and peripheral blood low-density immature neutrophils are isolated by gradient separation. In some other embodiments, the peripheral blood immature neutrophils are cultured in the presence of hybrid-inducing TCM (about 50% v/v) or IFN-γ and GM-CSF at concentrations of about 50-100 pg/ml. In particular embodiments, at day 5, similar to BMNs, a significant portion of G-CSF mobilized low-density PBNs acquire HLA-$DR^+CD14^+$ phenotype.

Figures 2A, 2B:
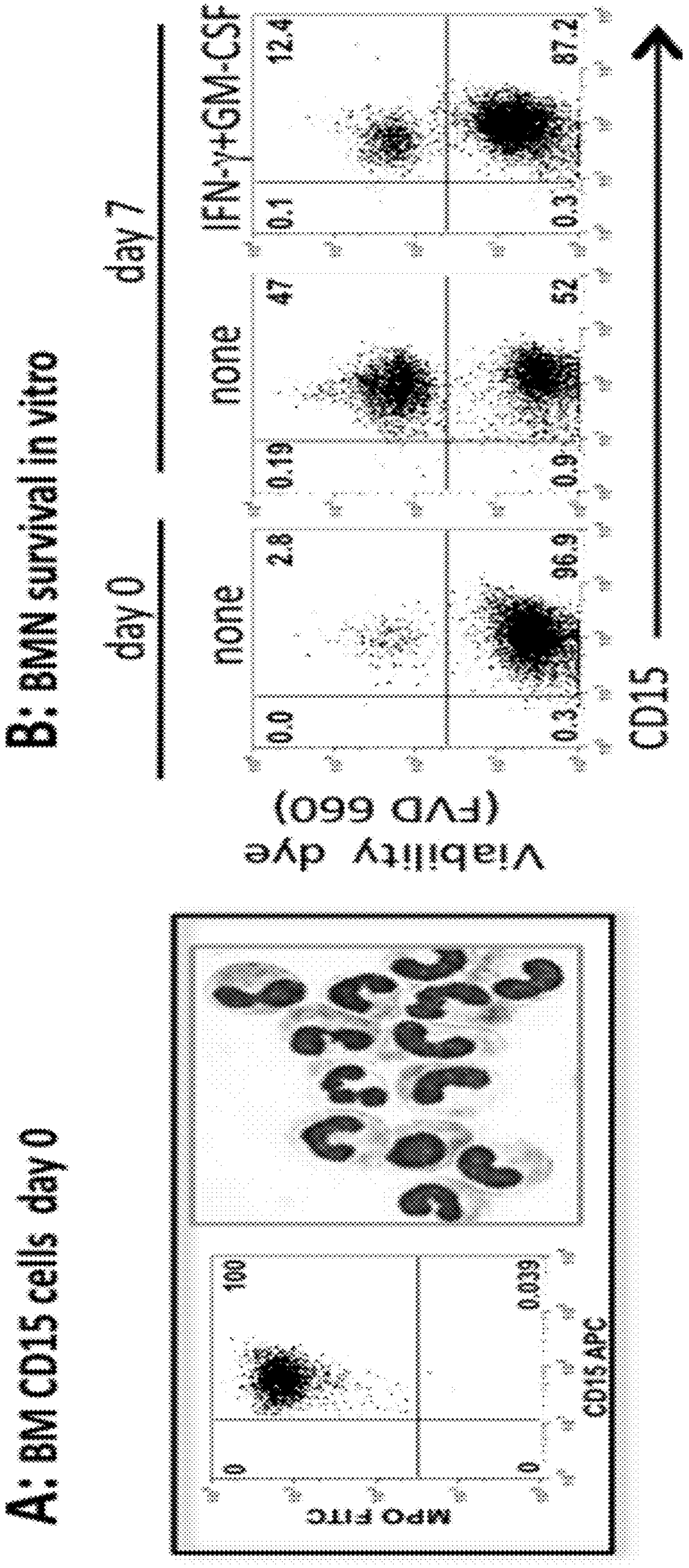
FIGS. 2A-2C are a series of plots and images showing long-lived bone marrow (BM) immature neutrophils in vitro. Neutrophils were purified from BM cell suspension using anti-CD15 magnetic beads.

In certain embodiments for the generation of hybrid neutrophils, the isolated or purified immature CD15-positive cells or immature granulocytes may be incubated or cultured with tumor conditioned medium (TCM), IFN-γ, GM-CSF, and/or lenalidomide as described herein for at least about 5 days, at least about 6 days, or at least about 7 days. In some embodiments, about 40% of bone marrow neutrophils (BMNs) could survive in cell culture for up to one week (FIG. 2B). Thus, human BMNs have a prolonged lifespan in vitro, providing large quantities of cells (>50 million cells) that can be used to generate hybrid neutrophils.

In certain embodiments, the hybrid neutrophil further expresses at least one molecule selected from the group consisting of: MHC class I, MHC class II, OX40L, 4-1BBL, CD86, CD40, and CCR7. In certain embodiments the expression level of any one of the aforementioned molecules is low, intermediate, or high. In certain embodiments the expression of any one of the molecules is increased relative to expression of the molecule on a canonical tumor-associated neutrophil (TAN).

In certain embodiments, the hybrid neutrophil expresses CD14, HLA-DR, CD32, CD64, and CD89. In other embodiments, the hybrid neutrophil expresses Arg1, MPO, CD66b, CD15, CD14, HLA-DR, MHC class I, OX40L, 4-1BBL, CD86, CD40, CCR7, CD32, CD64, and CD89. In certain embodiments, the expression of CD32 and/or CD64 and/or CD89 is high.

Methods of Treatment

The present invention features methods for increasing efficacy of an antibody against a tumor in a subject using hybrid neutrophils. Hybrid neutrophils are ideal effector cells for augmenting antibody-mediated immunotherapy of cancer or infectious diseases. Hybrid neutrophils are ideal for augmenting antibody-mediated immunotherapy for at least the following reasons: (1) hybrid neutrophils can be generated from BM of cancer patients in large numbers, (2) the most potent Fc receptors for triggering ADCC (CD32, CD64, and CD89) are highly up-regulated on hybrid neutrophils, and (3) hybrid neutrophils exhibit prolonged survival times, and (4) hybrid neutrophils are able to phagocyte bacteria at higher level than canonical neutrophils. In addition, the hybrid neutrophils have characteristics of antigen-presenting cells (APC) and thus may be able to more efficiently stimulate effector T cells. The ability of hybrid neutrophils to mediate efficient ADCC and augment effector T cell responses provides new opportunities to boost anti-tumor and anti-infectious immunity In some embodiments, the step of administering to the subject an effective amount of a hybrid neutrophil increases antibody-dependent cellular cytotoxicity (ADCC), antibody dependent phagocytosis (ADP), or effector T cell response in the subject. As described herein, the hybrid neutrophils provided by the present invention have been demonstrated to efficiently phagocytose bacteria, mediate a high level of antibody-dependent phagocytosis (ADP), mediate antibody-dependent cellular cytotoxicity (ADCC), and stimulate the effector T cell responses in vitro.

In patients with cancer or infectious diseases, enhancement of ADCC or ADP may be achieved by collecting bone marrow, expanding hybrid neutrophils ex vivo, and then reinfusing these cells in combination with therapeutic antibodies. The present invention thus features methods wherein the hybrid neutrophil is obtained by expanding a hybrid neutrophil population ex vivo in a biological sample obtained from the subject. In particular embodiments, the biological sample is bone marrow. In other embodiments, the biological sample is blood, particularly a blood sample comprising peripheral blood immature neutrophils. Generation of hybrid neutrophils from bone marrow (BM) immature CD15 cells in a bone marrow sample or from immature neutrophils in a blood sample may be accomplished by contacting the sample with tumor conditioned medium, interferon γ (IFN-γ), lenalidomide and/or an amount of granulocyte macrophage colony stimulating factor (GM-CSF). Methods for generating hybrid neutrophils from bone marrow or blood are further described elsewhere herein.

The present invention also features methods wherein the hybrid neutrophil is generated in situ in the subject. Without being bound by theory, it is also possible to generate a large numbers of hybrid neutrophils "in situ" by currently approved drugs (i.e., administration of lenalidomide or IFN-γ followed by GM-CSF). This could then be followed by therapeutic antibody treatment. Also this technology would be amenable for use in combination with conventional T cell immunotherapy to enhance and support the effect of cytotoxic T cell response against malignant or infected cells. Therapeutic antibodies used may be any antibody specifically binding to a tumor antigen. In some embodiments, the antibody is anti-Her2/neu antibody, rituximab, necitumumab, panitumumab or cetuximab. In particular embodiments, the antibody is cetuximab. In certain embodiments, the administration of the hybrid neutrophil may be concurrent with or followed by administration of the therapeutic antibody, anti-tumor antibody or antigen-binding fragment thereof.

Without being bound by theory, it is expected that the expansion of hybrid neutrophils ex vivo or in situ followed by the administration of therapeutic antibodies will be a more effective strategy to inhibit tumor growth for the following reasons: (1) hybrid neutrophils can be generated from BM or G-CSF/GMCSF mobilized peripheral blood neutrophils in large numbers; 2) the most potent Fc receptors for triggering ADCC (CD32, CD64, and CD89) are highly up-regulated on hybrid neutrophils; (3) hybrid neutrophils exhibit a high phagocytic activity; (4) hybrid neutrophils exhibit a prolonged survival time; and (5) ability of hybrid neutrophils to phagocyte tumor cells and present tumor antigens enables them to induce and support the cytotoxic T cell response against malignant cells, pathogen infected cells, or tumor cells. Example of tumors include, but are not limited to lung cancer, liver cancer, breast cancer, kidney cancer, gastric cancer, and pancreatic cancer. In some embodiments, the tumor comprises a non-small cell lung cancer (NSCLC).

The hybrid neutrophils generated as described herein can be administered to an animal, preferably a mammal, even more preferably a human, to treat a tumor, suppress tumor formation, and the like. In addition, the hybrid neutrophils of the present invention can be used for the treatment of any condition in which a tumor response, especially a cell-mediated immune tumor response, is desirable to treat or alleviate the disease. In particular, the administration of antibodies against tumor or pathogen-specific antigens in combination with hybrid neutrophils represents an effective strategy to inhibit tumor growth or infectious process. Accordingly, the present invention features methods of inhibiting tumor growth in a subject and treating a tumor in a subject, the methods comprising (a) administering to the subject an effective amount of an anti-tumor antibody or an antigen-binding fragment thereof; and (b) administering to or generating in the subject an effective amount of a hybrid neutrophil. In one aspect, the invention includes treating a condition, such as a tumor, in a subject, comprising administering to the subject a therapeutically effective amount of a pharmaceutical composition comprising a population of hybrid neutrophils.

Hybrid neutrophils of the invention and compositions comprising the hybrid neutrophils can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art. The cells of the invention to be administered may be autologous, allogeneic or xenogeneic with respect to the mammal undergoing therapy. In particular embodiments, the cells are autologous.

The administration of the cells of the invention may be carried out in any convenient manner known to those of skill in the art. The cells of the present invention may be administered to a mammal by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the mammal, a local disease site in the mammal, a lymph node, an organ, a tumor, and the like.

In one aspect the invention includes a method of inhibiting tumor growth in a subject. The method comprises (a) administering to the subject an effective amount of an anti-tumor antibody or an antigen-binding fragment thereof; and (b) administering to or generating in the subject an effective amount of a hybrid neutrophil, wherein the hybrid neutrophil expresses at least one neutrophil associated marker selected from the group consisting of: Arg1, MPO, CD66b, and CD15, and at least one antigen-presenting cell (APC) associated marker selected from the group consisting of: CD14, HLA-DR, CD32, CD64, and CD89, thereby inhibiting tumor growth in the subject.

In another aspect, the invention includes a method of increasing efficacy of an antibody against a tumor in a subject comprising (a) administering to the subject an effective amount of an anti-tumor antibody or an antigen-binding fragment thereof; and (b) administering to or generating in the subject an effective amount of a hybrid neutrophil, wherein the hybrid neutrophil expresses at least one neutrophil associated molecule selected from the group consisting of: Arg1, MPO, CD66b, and CD15, and at least one antigen-presenting cell (APC) associated molecule selected from the consisting of: CD14, HLA-DR, CD32, CD64, and CD89, thereby increasing efficacy of the antibody against the tumor in the subject.

In yet another aspect, the invention includes a method of treating a tumor in a subject comprising (a) administering to the subject an effective amount of an anti-tumor antibody or an antigen-binding fragment thereof; and (b) administering to or generating in the subject an effective amount of a hybrid neutrophil, wherein the hybrid neutrophil expresses at least one neutrophil associated molecule selected from the group consisting of: Arg1, MPO, CD66b, and CD15, and at least one antigen-presenting cell (APC) associated molecule selected from the group consisting of: CD14, HLA-DR, CD32, CD64, and CD89, thereby treating the tumor in the subject.

In one embodiment, the hybrid neutrophil further expresses at least one molecule selected from the group consisting of: MHC class I, MHC class II, OX40L, 4-1BBL, CD86, CD40, and CCR7. In another embodiment, the expression of at least one of any one of the molecules is low, intermediate, or high. In yet another embodiment, the expression of at least one of any one of the molecules is increased relative to expression of the molecule on a canonical tumor-associated neutrophil (TAN).

In another embodiment, the hybrid neutrophil expresses CD14, HLA-DR, CD32, CD64, and CD89. In yet another embodiment, the hybrid neutrophil expresses Arg1, MPO, CD66b, CD15, CD14, HLA-DR, MHC class I, OX40L, 4-1BBL, CD86, CD40, CCR7, CD32, CD64, and CD89. In still another aspect the expression of CD32 and/or CD64 and/or CD89 is high.

In certain embodiments, the step of administering to the subject an effective amount of a hybrid neutrophil increases antibody-dependent cellular cytotoxicity (ADCC), antibody-dependent phagocytosis (ADP), or effector T cell response in the subject. In other embodiments, the step of administering to or generating in the subject an effective amount of a hybrid neutrophil is followed by the step of administering to the subject an effective amount of an anti-tumor antibody or an antigen-binding fragment thereof. In other embodiments, the step of administering to or generating in the subject an effective amount of a hybrid neutrophil is concurrent with the step of administering to the subject an effective amount of an anti-tumor antibody or an antigen-binding fragment thereof.

Pharmaceutical Compositions

Pharmaceutical compositions of the present invention may comprise hybrid neutrophils as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an effective amount," "an immunologically effective amount", "an anti-immune response effective amount", "an immune response-inhibiting effective amount", or "therapeutic amount" is indicated, the precise amount of the compositions of the present invention to be administered can be determined by a physician with consideration of individual differences in age, weight, immune response, and condition of the patient (subject/mammal). It can generally be stated that a pharmaceutical composition comprising the hybrid neutrophils described herein may be administered at a dosage of $10^4$ to $10^9$ cells/kg body weight, preferably $10^5$ to $10^6$ cells/kg body weight, including all integer values within those ranges. Cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to draw a blood or bone marrow sample from a subject, generate hybrid neutrophils therefrom according to the present invention, and reinfuse the patient with these cells. This process can be carried out multiple times every few weeks. In certain embodiments, cells can be obtained from blood draws of from 10 ml to 400 ml. In certain embodiments, cells are obtained from blood draws of 20 ml, 30 ml, 40 ml, 50 ml, 60 ml, 70 ml, 80 ml, 90 ml, or 100 ml. Without being bound by theory, using this multiple blood draw/multiple reinfusion protocol, may select out certain populations of cells. In particular embodiments, the cells of the invention are administered in conjunction with (e.g., before, simultaneously or following) therapeutic anti-tumor antibodies. Examples of anti-tumor antibodies include, without limitation, anti-Her2/neu antibody, rituximab, necitumumab, panitumumab and cetuximab.

In certain embodiments of the present invention, cells are generated using the methods described herein, or other methods known in the art where cells are obtained at therapeutic levels, administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or other treatments for PML patients. In further embodiments, the cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded hybrid neutrophils of the present invention. In an additional embodiment, expanded cells are administered before or following surgery.

In certain embodiments, the cells described herein may be used for the manufacture of a medicament for the treatment of an immune response in a subject in need thereof. In yet other embodiments, the cells described herein may be used for the manufacture of a medicament for the treatment of a cancer, particularly a tumor, in a subject in need thereof.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook et al., (2012) Molecular Cloning, Cold Spring Harbor Laboratory); "Oligonucleotide Synthesis" (Gait, M. J. (1984). Oligonucleotide synthesis. IRL press); "Culture of Animal Cells" (Freshney, R. (2010). Culture of animal cells. Cell Proliferation, 15(2.3), 1); "Methods in Enzymology" "Weir's Handbook of Experimental Immunology" (Wiley-Blackwell; 5 edition (Jan. 15, 1996); "Gene Transfer Vectors for Mammalian Cells" (Miller and Carlos, (1987) Cold Spring Harbor Laboratory, New York); "Short Protocols in Molecular Biology" (Ausubel et al., Current Protocols; 5 edition (Nov. 5, 2002)); "Polymerase Chain Reaction: Principles, Applications and Troubleshooting", (Babar, M., VDM Verlag Dr. Müller (Aug. 17, 2011)); "Current Protocols in Immunology" (Coligan, John Wiley & Sons, Inc. Nov. 1, 2002).

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Study Design. A total of 109 patients with stage I-II lung cancer, who were scheduled for surgical resection, consented to tissue collection of a portion of their tumor and/or blood for research purposes. All patients selected for entry into the study met the following criteria: (i) histologically confirmed pulmonary squamous cell carcinoma (SCC) or adenocarcinoma (AC), (ii) no prior chemotherapy or radiation therapy within two years, and (iii) no other active malignancy. Detailed characteristics of the patients can be found in FIG. 12.

Reagents. The enzymatic cocktail for tumor digestion consisted of serum-free Hyclone™ Leibovitz L-15 media supplemented with 1% Penicillin-Streptomycin, Collagenase type I and IV (170 mg/L=45-60 U/mL), Collagenase type II (56 mg/L=15-20 U/mL), DNase-I (25 mg/L), and Elastase (25 mg/L) (all from Worthington Biochemical, NJ). Complete cell culture media DME/F-12 1:1 media (HyClone, Thermo Scientific) was supplemented with 2.5 mM L-glutamine, 15 mM HEPES Buffer, 10% of Embryonic Stem (ES) Cell Screened FBS (U.S.) (Thermo Scientific™ HyClone™), Penicillin (100 U/ml) and Streptomycin (100 μg/mL). HLA-A*0201-restricted NY-ESO-1 peptide was synthesized by AnaSpec, Inc (Fremont, Calif.). Pierce™ NY-ESO-1 full-length recombinant protein and anti-NY-ESO-1 monoclonal Abs (clone E978 IgG1) were purchased from Thermo Scientific™. The PepMixCEF-MHC class I peptide pool (23 viral peptides) and The PepMixCEFT-MHC class II peptide pool (14 viral peptides) were purchased from JPT Peptide Technologies (Acton, Mass.). These peptide pools contain MHC class I and class II-restricted T-cell epitopes from CMV, EBV and Influenza virus, designed to stimulate T cells from donors with a variety of HLA types. Human recombinant IFN-γ, GM-CSF, IL-4 and M-CSF were purchased from PeproTech, Inc.

Preparation of a Single-Cell Suspension from Tumor and Adjacent Lung Tissue. Surgically-removed fresh lung tumors and adjacent lung tissue were processed within 20 minutes of removal from the patient. An optimized disaggregation method for human lung tumors was used that preserves the phenotype and function of the immune cells (Quatromoni et al., 2015. *J. Leukoc. Biol.* 1, 201-209). Briefly, under sterile conditions, all areas of tissue necrosis were trimmed away. The tumor and adjacent uninvolved lung tissue was sliced into 1-2 $mm^3$ pieces with microdissecting scissors equipped with tungsten carbide insert blades (Biomedical Research Instruments, Inc. Silver Spring, Md.). For enzymatic digestion, the pieces were incubated in a shaker for 45 minutes at 37° C. in serum-free L-15 Leibovitz media (HyClone) containing different enzymes at low concentrations and 1% Penicillin-Streptomycin (Life Technologies, Carlsbad, Calif.). L-15 Leibovitz media was formulated for use in carbon dioxide-free systems. After 45 minutes, any visible tumor pieces were vigorously pipetted against the side of a 50 mL tube to enhance disaggregation and then further incubated for 30-50 minutes under the same conditions. Larger pieces of tumor tissue were permitted to settle to the bottom of the tube and the supernatant was passed through a 70 μM nylon cell strainer (BD Falcon). The remaining pieces in the tube underwent further pipetting before being passed through the same cell strainer. Typically, less than 5% of the tissue (consisting of chiefly non-cellular connective tissue) remained on the cell strainer. After filtration the red blood cells were lysed using 1× Red Blood Cell (RBC) Lysis Buffer (Santa Cruz, Dallas, Tex.). The remaining cells were washed twice in RPMI supplemented with 2% FBS and re-suspended in the cell culture media. Cell viability, as determined by trypan blue exclusion or Fixable Viability Dye eFluor® 450 staining, was typically >90%. If the viability of cells was less than 80%, dead cells were eliminated using a "dead cell removal kit" (Miltenyi Biotec Inc., Germany).

Tumor-Conditioned Media. A single-cell suspension was obtained from lung tumors by enzymatic digestion as described herein. After washing the cells with PBS, the single cell suspensions were re-suspended in DMEM/F12 (HyClone) medium supplemented with 5% FBS/antibiotics (penicillin/streptomycin, HyClone) and placed in 175 $mm^2$ flasks at a concentration of $2\times10^6$ cells/mL. Twenty-four hours later, supernatant (tumor-conditioned medium, TCM) was collected, filtered, aliquoted, and frozen at −80° C.

Neutrophil Isolation. TANs were isolated from tumor single-cell suspensions using positive selection of $CD15^+$ or $CD66b^+$ cells with microbeads as previously described (Eruslanov et al., 2014. *J. Clin. Invest.* 12, 5466-5480). TAN subsets were flow sorted based on the phenotype of canonical ($CD11b^+CD66b^+CD15^{hi}HLA\text{-}DR^-$) and hybrid ($CD11b^+CD66b^+CD15^{hi}HLA\text{-}DR^+$) TANs. PBNs and BMNs were isolated from EDTA anticoagulated peripheral blood and BM single-cell suspension, respectively, using positive selection of $CD15^+$ or $CD66b^+$ cells with microbeads.

Since temperature gradients can activate neutrophils, all tissues and reagents were maintained at a constant temperature during preparation. After tumor harvest, the neutrophil populations used in this study were prepared at room temperature (RT) and rapidly utilized. TANs were isolated from tumor single-cell suspensions using positive selection of $CD15^+$ or $CD66b^+$ cells. In the rare instances when cellular aggregates formed, the suspensions were passed through a 30 μM pre-separation filter (Miltenyi) before addition to the LS columns (Miltenyi). For positive selection of TANs through engagement of the CD15 transmembrane protein, single cell suspensions were incubated with anti-CD15 antibody (Ab)-conjugated magnetic microbeads (Miltenyi Biotec) for 15 minutes. For positive selection of TANs through engagement of the CD66b transmembrane protein, single cell suspensions were first incubated with PEconjugated anti-CD66b Abs (Biolegend) and then with anti-PE microbeads (Miltenyi Biotec). In some experiments, TANs were isolated by flow cytometric cell-sorting based on the phenotype of TANs as $CD11b^+CD66b^+CD15^{hi}$. Neutrophils from distant non-involved lung tissue were isolated similarly to TANs.

TAN subsets were sorted based on the phenotype of canonical ($CD11b^+CD66b^+CD15^{hi}HLA\text{-}DR^-$) and hybrid ($CD11b^+CD66b^+CD15^{hi}\text{-}HLA\text{-}DR^+$) TANs. Gating strategy for flow cytometry sorting of canonical and hybrid TANs is shown in FIG. S1N and S1O. $CD11b^+$ myeloid cells are all $CD45^+EpCam^-$ cells. Sterile cell sorting was performed on the BD FACSAria II (BD Biosciences) and MoFlo® Astrios™ (Beckman Coulter).

PBNs were obtained from EDTA anti-coagulated peripheral blood collected from lung cancer patients during surgery or from healthy donors. The PBNs were obtained from Lymphoprep (Accu-Prep, 1.077 g/ml, Oslo, Norway) density gradient centrifugation followed by erythrocyte lysis with lx RBC Lysis Buffer. To account for any possible effect of tissue digestion enzymes on the function neutrophils, peripheral blood granulocytes were processed in a similar manner. Specifically, peripheral blood granulocytes were incubated with enzymatic cocktail before positive selection using microbeads or flow cytometry.

BMNs were isolated from bone marrow cell suspensions using positive selection of $CD15^+$ or $CD66b^+$ cells with microbeads according to the manufacturer's instructions (Miltenyi Biotec, Auburn, Calif.). Bone marrow cell suspension was obtained from the rib fragments that were removed from patients as part of their lung cancer surgery. The single cell suspension was obtained by vigorous pipeting of cells flushed from bone marrow and passing the disaggregated cells through a 70 μN1 nylon cell strainer. To exclude the possible contamination of common progenitors, neutrophils were isolated from a CD34-depleted population of bone marrow cells. Anti-CD15 Ab-conjugated magnetic microbeads (Miltenyi Biotec) or PEconjugated anti-CD66b Abs (Biolegend) and anti-PE microbeads (Miltenyi Biotec) were used for positive selection. Given that resting naïve neutrophils do not tightly adhere to cell culture plastic as opposed to macrophage and monocytes the bead sorted BM neutrophils were additionally cultured in cell culture dishes to exclude the possible contamination of BM macrophages/monocytes. Two-four hours later, the floating cells were removed and used for further experiments.

The purity and activation status of isolated TANs, BMNs and PBNs were measured by flow cytometry for the granulocyte/myeloid markers CD66b, CD15, arginase-1 (Arg), myeloperoxidase (MPO), CD11b, and the activation markers CD62L and CD54 as described (Eruslanov et al., 2014. *J. Clin. Invest.* 12, 5466-5480). All neutrophil subsets demonstrated high cell viability with minimal enzyme-induced premature cellular activation or cleavage of myeloid cell markers. The purity of TANs, BMNs and PBNs was typically higher than 94%. Isolates with less than 90% purity were discarded. To evaluate the cytomorphology of isolated PBNs, BMNs, and TAN subsets cells were spun on glass slides and stained with the Hema3 Stat Pack Kit (Fisher Scientific).

Lymphocyte isolation from Peripheral Blood. Standard approaches were utilized. Peripheral blood mononuclear cells (PBMCs) were separated by 1.077 g/ml Lymphoprep (Accu-Prep, Norway) gradient density centrifugation of EDTA anti-coagulated whole blood collected from cancer patients and healthy donors. T cells were purified from the PBMC fraction using human T cell enrichment columns (R&D Systems, Inc.) according to the manufacturer's protocol.

Generation of BM-Derived Hybrid and Canonical Neutrophils. To differentiate BMNs into cells that resemble canonical TANs, purified long-lived BMNs were cultured for 7 days with a TCM (50% v/v) collected from a patient's tumor digest where a large number of hybrid TANs were previously unable to be identified by flow cytometry. To differentiate BMNs into cells that resemble hybrid TANs, purified long-lived BMNs were cultured for 5-7 days with a TCM (50% v/v) collected from a tumor digest where the frequency of hybrid TANs was markedly elevated (≥15% of all TANs). Alternatively, hybrid-neutrophils were differentiated from BMNs with low doses IFN-γ (50 pg/ml) and GM-CSF (50 pg/ml) for 7 days. If it was observed that the formation of hybrid BMNs was less than 80% the HLA-DR+CD14+ hybrid cells from TCM treated BMNs were enriched by positive selection using magnetic beads coated with anti-HLA-DR antibodies or by flow cytometric cell sorting. The proliferation of BMNs during the differentiation was assessed by flow cytometry using BrdU Flow Kit (BD Pharmingen). BMNs were exposed to bromo-deoxyuridine for 6 hours.

To test the effect of hypoxia on hybrid neutrophil formation, BMNs were cultured for 6 days under normoxic and hypoxic culture conditions maintained in a 37° C. incubator containing 5% $CO_2$, and either atmospheric 21% $O_2$ or 5% $O_2$ condition (Hypoxia Incubator Chamber, Stemcell Techology). BMNs were also cultured in the presence of hybrid-inducing TCM and cobalt chloride (25 μM) (MP Biomedicals LLC), an agent that induces the hypoxia-inducible factor-1α, the main transcriptional factor activated in hypoxic conditions.

To differentiate hybrid neutrophils from circulating immature neutrophils, peripheral blood collected from healthy donors who were treated with G-CSF (filgrastim) was used to mobilize hematopoietic stem cells for allogeneic hematopoietic cell transplantation. Peripheral blood mononuclear cells (PBMCs) were separated by 1.077 g/ml Lymphoprep (Accu-Prep, Norway) gradient density centrifugation of EDTA anti-coagulated whole blood collected from G-CSF treated healthy donors. Low-density immature neutrophils were isolated from PBMC using anti-CD15 microbeads and cultured with hybrid-inducing TCM for 7 days.

Generation of BM-Derived Macrophages and Dendritic Cells. BM-derived macrophages and dendritic cells were generated by culturing $CD15^-CD11b^+$ BM cells with M-CSF or IL-4 and GM-CSF, respectively. Macrophages and dendritic cells were differentiated from myeloid C $CD11b^+$ cells purified with CD11b beads from CD15-depleted bone marrow cell suspensions. To obtain BM-derived mature dendritic cells (DC), CD11b cells were cultured in the presence of GM-CSF (25 ng/ml) and IL-4 (25 ng/ml) for 7 days in the complete cell culture medium, as described in detail elsewhere (Inaba, et al, 1992. *J. Clin. Invest.* 12, 5466-5480; Lutz, et al, 1999. *J. Immunol. Methods.* 1, 77-92). Maturation cocktail (LPS 100 ng/ml and sOX40L 50 ng/ml) was added during the last 24 hours of cell culturing. To obtain BM-derived macrophages (Mph), BM CD11b cells were cultured in the presence of M-CSF in the complete cell culture medium for 7 days as described in detail elsewhere (Manzanero, 2012. *Methods Mol. Biol.* 177-181).

Flow Cytometry. Flow cytometric analysis was performed according to standard protocols. Negative gating was based on a fluorescence minus one (FMO) strategy. To exclude dead cells from analysis, cells were stained with the Fixable Viability Dye eFluor® 450 (ebioscience), LIVE/DEAD® fixable dead cell stains (Molecular probes, Life Technologies), or Zombie Yellow™ Fixable Viability dye (Biolegend). To distinguish early-stage apoptotic and late-stage apoptotic/necrotic cells, cells were first stained with Fixable Viability Dye eFluor® 660 (eBioscience). Then cells were washed with the AnnexinV-Binding Buffer and stained with anti-AnnexinV Abs (FITC) in the AnnexinV-Binding Buffer for 10 min at RT. Cells were washed and analyzed by flow cytometry.

For intracellular staining, fixed cells stained for surface markers were permeabilized with BD Perm/Wash™ Buffer (BD Biosciences) and then stained with the following Abs for 45 minutes at RT: antihuman Arg (R&D Systems), anti-human MPO (e-bioscience), FITC-anti-human IFN-γ (Biolegend, clone: 4S.B3), APC anti-human GranzymeB (Biolegend, clone GB11) or PE-anti-human/mouse IRF8 (ebioscience, Clone: V3GYWCH). For NE staining, fixed cells stained for surface markers were permeabilized with BD Perm/Wash™ Buffer (BD Biosciences) and then incubated with 1×PBS/10% normal goat serum (Abcam)/0.3M glycine to block non-specific protein interactions followed by the antihuman Neutrophil Elastase antibodies (EPR7479, Abcam) for 30 min at RT. The secondary Abs used were goat anti-rabbit (Abcam) at 1/2000 dilution for 30 min at RT. Isotype control Abs were rabbit IgG used under the same conditions.

For transcription factor Ikaros staining, cells were stained with fluorochrome-labeled primary Abs for 20 min on ice. After washing in FACS buffer (BD Biosciences), cells were fixed with Fix/Perm™ Buffer (BD Biosciences). Following fixation, cells were permeabilized with Perm/Wash™ Buffer (BD Biosciences) and incubated with rabbit anti-mouse Ikaros (ab26083, Abcam, Cambridge, Mass.). Following staining with the Ikaros Ab, cells were washed and then stained with a PE-labeled anti-rabbit secondary Ab.

For phenotypic and functional analysis PBNs, BMNs, and TANs were gated on live $CD11b^{+}CD15^{hi}CD66b^{+}$ cells. The following cell surface antibodies were utilized: anti-CD11b (Biolegend, clone: ICRF44), anti-CD15 (Biolegend, clone: HI98), anti-CD66b (Biolegend, clone: G10F5), anti-CD54 (Biolegend, clone: HA58), anti-CD62L Biolegend, (clone: DREG-56), anti-CCR5 (Biolegend, clone: HEK/1/85a), anti-CCR7 (Biolegend, clone: G043H7), anti-CXCR1 (Biolegend, clone: 8F1/CXCR1), anti-CXCR2 (Biolegend, clone: 5e8/cxcr2), anti-PD-L1 (Biolegend, clone: M1H1), anti-Gal-9 (Biolegend, clone: 9M1-3), anti-CD301 (Biolegend, clone: H037G3), anti-CD200R, (Biolegend, clone: OX-108), anti-FASL (Biolegend, clone: NOK-1), anti-TRAIL (Biolegend, clone: RIK2), anti-TWEAK (clone: CARL-1), anti-CD86 (Biolegend, clone: IT2.2), anti-CD80 (Biolegend, clone:2D10), anti-CD40 (Biolegend, clone: 5C3), anti-OX40L (Biolegend, clone:11C3-1), anti-4-1BBL (Biolegend, clone:5F4), anti-HLA-A2 (Biolegend, clone: bb7.2), anti-CD14 (Biolegend, clone: M5E2), anti-HLA-DR (BD Bioscience, clone: G46-6), anti-CD206 (Biolegend, clone: 15-2), anti-CD115 (Biolegend, clone: 9-4D2-1E4), anti-CD83 (Biolegend, clone: HB15e), anti-CD1c (Biolegend, clone: L161), anti-CD204 (Biolegend, clone: 7G5C33), anti-CD209 (Biolegend, clone: 9E9A8), anti-CD163 (Biolegend, clone: GHI/61). All data were acquired using the BD FACSCalibur or BD LSRFortessa™ (BD Bioscience) flow cytometers and analyzed using FlowJo software (TreeStar Inc.).

Antigen Non-specific T Cell Response. To induce antigen non-specific T cell responses, PBMC or purified T cells were stimulated with plate-bound anti-human CD3 and/or anti-CD28 antibodies. To evaluate the effects of different neutrophil subsets on antigen non-specific autologous T cell response, several parameters were measured: (i) T cell proliferation using standard CFSE dilution method or BrdU incorporation assay, (ii) T cell IFN-γ production using intracellular cytokine staining, and (iii) expression of T cell activation markers CD25 and CD69 using flow cytometry.

PBMCs or purified T cells (responders) were labeled with 5 μM of the fluorescent dye 5,6-carboxyfluorescein diacetate succinimidyl ester (CFSE) (Invitrogen, Molecular Probe), according to the manufacturer's instructions. CFSE-labeled PBMCs or T cells were stimulated with plate-bound anti-human CD3 Ab or anti-human CD3 (clone: OKT3) and anti-human CD28 (clone: CD28.2) Abs (Biolegend), respectively. To coat the 96 U-bottom well plates with Abs, anti-CD3 (1 μg/ml) and/or anti-CD28 Abs (5 μg/ml) were added in 100 μL of PBS per well and incubated for 4 hours at 37° C. Wells were washed twice with PBS before the addition of cells. CFSE-labeled responders ($1.5\times10^{5}$ cells/well) were mixed with either different subsets of TANs or differentiated BMNs or PBNs in a 1:1 ratio and co-cultured in CD3/CD28-coated plates for 4 days in the complete cell culture media. The CFSE signal was analyzed by flow cytometry on gated CD4 and CD8 lymphocytes. In other experiments, the proliferation of T cells was assessed by flow cytometry using BrdU Flow Kit (BD Pharmingen). Forty-eight hours after stimulation, T cells were exposed to bromo-deoxyuridine for 12 hours.

To measure IFN-γ production, $1.5\times10^{5}$ autologous PBMCs stimulated with plate-bound antihuman CD3 Ab were co-incubated with different neutrophil subsets in a 1:1 ratio for 48 hr in 96 well Ubottom plate in the complete cell culture media. To accumulate intracellular IFN-γ, BD GolgiStop™ and BD GolgiPlug™ were added into the cell cultures during the last 12 hr. The cells were collected, washed in Stain Buffer (BD Biosciences) and stained for surface markers as described herein. Surface stained cells were fixed with BD Cytofix™ Fixation Buffer (BD Biosciences) for 20 minutes. The fixed cells were permeabilized with BD Perm/Wash™ Buffer (BD Biosciences) and then stained with the anti-human IFN-γ (Biolegend, clone: 4S.B3). The percent of IFN-γ positive CD4 and CD8 cells was analyzed by flow cytometry.

To measure the expression of T cell activation markers, purified autologous T cells stimulated with plate-bound anti-human CD3 and CD28 Ab were co-incubated with different neutrophil subsets at concentration $1.5\times10^{5}$ cells/well (96 well U-bottom plate) in a 1:1 ratio for 24 hr in the complete cell culture media. The cells were collected, washed in Stain Buffer (BD Biosciences) and stained for surface activation markers CD25 and CD69 as described herein.

Virus-Specific Memory T Cell Response. Autologous T cells purified from peripheral blood with human T cell enrichment columns (R&D Systems, Inc.) were used as responders and co-cultured with different subsets of neutrophils that had been pulsed with a mixture of peptides from Cytomegalovirus, Epstein-Barr virus, Influenza virus or *Clostridium tetani* with a broad array of HLA types. Since most humans have been exposed to these antigens, these peptide pools are good control antigens for eliciting a response from antigen-specific memory T cells in PBMC samples. Specifically, TAN subsets were sorted based on the phenotype of canonical ($CD11b^{+}CD66b^{+}CD15^{hi}HLA\text{-}DR^{-}$) and hybrid ($CD11b^{+}CD66b^{+}CD15^{hi}LA\text{-}DR^{+}$) TANs as described herein. BM-derived canonical and hybrid neutrophils were differentiated with different types of TCM as described herein. Tumor and BM-derived canonical and hybrid neutrophils were incubated with 2 μg/ml of PepMix-CEF-MHC class I or PepMixCEFT-MHC class II peptide pools (JPT Peptide Technologies) for 30 minutes. Neutrophil subsets incubated with irrelevant mesothelin-derived peptides were used as a negative control to define a background. Following extensive washing, $1\times10^{4}$ of neutrophils pulsed with viral peptides were incubated with $5\times10^{4}$ autologous T cells in 96-Well PVDF Membrane ELISPOT Plate (Millipore) for 2 days. The T cell response was quantified by human IFN-gamma ELISPOT (Ready-SET-Go!®, eBioscience) according to the manufacturer's instructions. IFN-γ positive spots were counted and analyzed using ImmunoSpot® S5 Micro Analyzer (Cellular Technology Limited).

Generation of NY-ESO specific Ly95 T cells and A549-NY-ESO-1-A2 target lung cancer cell line. The NY-ESO-1-reactive Ly95 TCR construct is an affinity-enhanced variant of the wild-type IG4 TCR identified from T cells recognizing the HLA-A2 restricted NY-ESO-1:157-165 peptide antigen. The generation of this Ly95 TCR construct and its packaging into a lentiviral vector has been described in detail previously (Moon et al., 2016. *Clin. Cancer Res.* 22, 436-447; Robbins et al., 2008. *J. Immunol.* 9, 6116-6131). Human T cells were isolated from PBMC of healthy volunteer donors by negative selection using RosetteSep kits (Stem Cell Technologies, Vancouver, Canada). Isolated T cells were stimulated with magnetic beads coated with anti-CD3/anti-CD28 at a 1:3 cell to bead ratio. T cells were transduced with lentiviral vectors at an MOI of approximately 5. Cells were counted and fed with complete cell culture medium every 2 days. A small portion of expanded cells was stained for flow cytometry confirmation of successful Ly95 transduction using the Vβ13.1 TCR chain antibody (Beckman Coulter: clone IMMU 222). Transduction of human T cells undergoing anti-CD3/CD28 bead activation with high titer lentivirus that encodes the Ly95 TCR recognizing NY-ESO-1 resulted in approximately 20-50% of $TCRVb13.1^+$ CD8 cells.

For target cells, the A549 human lung adenocarcinoma cell line was genetically modified to express both NY-ESO-1 protein and HLA-A*02 as described earlier (Moon et al., 2016. *Clin. Cancer Res.* 22, 436-447). Briefly, A549 cell line was transduced by a retroviral vector encoding NY-ESO-1-T2A-HLA-A*02. The transduced A549 cells were subjected to limiting dilution at 0.5 cell per well in 96-well plates. Resulting clones were tested by flow cytometry for HLA-A*02 expression using anti-HLA-A2 Abs (Biolegend, clone: bb7.2). HLA-A2 positive clones were selected and tested in co-culture with T cells expressing the NY-ESO-1 Ly95 TCR. The clones expressing HLA-A2 that could stimulate NY-ESO-1 Ly95 TCR-expressing T cells to secrete IFN-γ were pooled to generate the A549-NY-ESO-1-A2 (A549-A2-ESO) cell line.

NY-ESO-Specific T Cell Response. To study the regulation of antigen-specific effector T cell responses by neutrophil subsets, TCR transduced T cells (Ly95 T cells) recognizing the HLA-A2 restricted NY-ESO-1:157-165 peptide antigen were used. In one set of experiments, in order to stimulate the Ly95 T cell response, an A549 human lung adenocarcinoma cell line that was genetically modified to express both NY-ESO-1 protein and HLA-A*02 A549 (A2-NY-ESO-1 tumor cells) was used. The Ly95 T cells at concentration $1.5\times10^5$ cells/well (96 well-U-bottom plate) were mixed with A549 A2-NY-ESO-1 tumor cells in the presence of different neutrophil subsets at ratio 1:0.25:1 (Ly95 T cells: A549 A2-NY-ESO-1: Neutrophils) for 18 hours in the complete cell culture media. BD GolgiStop™ and BD GolgiPlug™ were added into the cell cultures during the last 12 hr. The Ly95 T cells co-cultured with NY-ESO-1 negative A549 tumor cells and neutrophil subsets were used as a negative control to define the level of allostimulation. The cells were collected, washed in Stain Buffer (BD Biosciences) and stained for CD8 and Ly95 TCR surface markers using anti-CD8 (Biolegend, clone: HIT8a) and anti-TCRVβ13.1 (Beckman Coulter: clone IMMU 222) antibodies with following intracellular staining for IFN-γ as described herein. The production of IFN-γ and Granzyme B was analyzed in gated $CD8^+TCRVP13.1^+$ cells by flow cytometry.

In several experiments, blocking Abs against CD86 (clone: IT2.2), OX40L (clone: 11C3.1), 4-1BBL (clone: 5F4), CD54 (clone: HCD54), (all from Biolegend) were added to the co-cultures of hybrid neutrophils and Ly95 T cells activated with A549 A2-NY-ESO-1 tumor cells. The blocking Abs at the concentration 5 μg/ml were present in neutrophils/Ly95 cell co-culture for 18 hours, starting from the beginning of the assay. Matched isotype antibodies were used as controls. Transwell assays were performed using 24-well flat-bottom Transwell culture plates (Corning) with inserts of 0.4 μm membrane pore size (Corning). To separate Ly95 T cells and neutrophil subsets, $0.5\times10^6$ Ly95 T cells were mixed with A549 A2-NY-ESO-1 tumor cells in ratio 1:0.25 and added to the bottom chamber. BM-derived canonical and hybrid neutrophils were placed in the top at a ratio of 1:1 (Ly95 cells:Neutrophils). Cells were cultured in complete cell culture media for 24 hours and the production of intracellular IFN-γ was measured in gated $CD8^+$ $TCRV\beta13.1^+$ cells by flow cytometry.

Antigen presenting cell functions of hybrid neutrophils. To assess whether the hybrid neutrophils perform functions of APCs, the effector Ly95 T cells were stimulated with different subsets of $HLA\text{-}A{*}02^+$ neutrophils pulsed with HLA-A*02-restricted NY-ESO-1 peptide. For this purpose, HLA-A*02 positive BM-derived canonical and hybrid neutrophils were incubated with NY-ESO-1 peptide (1 μg/ml) for 1 hour, washed three times with cell culture medium and mixed with Ly95 T cells at concentration $1.5\times10^5$ cells/well (96 well U-bottom plate) in ratio 1:1 in the complete cell culture media. Eighteen hours later, NY-ESO-specific activation of the Ly95 cells was assessed by measuring intracellular IFN-γ in gated $CD8^+TCRVP13.1^+$ cells.

To assess whether the hybrid neutrophils cross-present NY-ESO epitopes, HLA-A*02 positive BM-derived canonical and hybrid neutrophils were differentiated as described above but in AIM V AlbuMAX® serum free cell culture medium. These neutrophil subsets were incubated with free NY-ESO full-length protein (5 μg/ml) or NY-ESO immune complex for 12 hours in AIM V AlbuMAX® serum free cell culture medium prior Ly95 T cells assays. NY-ESO Immune complexes were formed by incubating the NY-ESO full-length protein (5 μg/ml) with monoclonal anti-NY-ESO Abs (clone E978, Thermo Scientific™) for 30 minutes at 37° C. Following extensive washing in serum free medium, $1\times10^5$ neutrophils were mixed with $5\times10^3$ Ly95 T cells (transduction efficiency: 20% of $CD8^+TCRVP13.1^+$ cells) in 96-Well PVDF Membrane ELISPOT Plate (Millipore) in AIM V AlbuMAX® serum free cell culture. NY-ESO-free neutrophils incubated with Ly95 T cells were used as a negative control to define a background and level of allostimulation. Twenty four hours later, the NY-ESO-specific production of IFN-Y by Ly95 cells was assessed by human IFN-γ ELISPOT (Ready-SET-Go!®, ebioscience) according to the manufacturer's instructions. IFN-Y positive spots were counted and analyzed using ImmunoSpot® S5 Micro Analyzer (Cellular Technology Limited).

To determine the ability of canonical and hybrid neutrophils to uptake and process an antigen, DQ-OVA (Molecular Probes) was used which is a self-quenched conjugate of ovalbumin that exhibits bright green fluorescence upon proteolytic degradation. Briefly, BM-derived canonical and hybrid neutrophil subsets were incubated with DQ-OVA (10 μg/ml) at 37° C. for 2 hours. Cells incubated at 4° C. served as controls. Neutrophils were collected, washed with cold Stain Buffer (BD Biosciences) and stained with APC-anti-HLA-DR Abs (BD Bioscience, clone: G46-6) at 4° C. The green fluorescence was analyzed by flow cytometry in canonical $HLA\text{-}DR^-$ and hybrid $HLA\text{-}DR^+$ neutrophils.

Allogeneic Mixed-Lymphocyte Reaction (MLR). Purified allogeneic T cells from healthy donor PBMCs were used as responders and reacted with $1\times10^5$ BM-derived canonical or hybrid neutrophils (inducers) from lung cancer patients at a ratio of 1:1 in 96-well round bottom plate (Corning®). Five days later, the proliferation of CD4 and CD8 T cells was measured using a BrdU incorporation assay (BD Pharmaingen) according to the manufacturer's instructions.

Phagocytosis. The phagocytic activity of neutrophil subsets was assayed with the pHrodo™ Red *E. coli* BioParticles® Phagocytosis Kit for flow cytometry (Life Technologies™), according to the manufacturer's instructions. Briefly, TANs or BM-derived hybrid neutrophils were incubated with pHrodo™ Red *E. coli* for 1 hour at 37° C. in 5% CO2. After incubation, the neutrophils were washed twice with cold PBS and stained for the surface HLA-DR to distinguish the canonical HLA-$DR^-$ and hybrid HLA-DR+ neutrophils. The level of phagocytosis was analyzed by flow cytometry in gated HLA-$DR^+$ and HLA-DR− cells.

Neutrophil survival in vitro. PBNs and BMNs were cultured at concentration $1\times10^6$/ml in the presence or absence of TCM (50% v/v) in 24 well clear tissue culture-treated plate (Corning®) in complete cell culture media. Three and 7 days later neutrophil viability was analyzed by flow cytometry using Fixable Viability dye FVD 660 (eBioscince).

Measurement of cytokines, chemokines and growth factors. The levels of 30 cytokines/chemokines and growth factors were measured in TCM using the Cytokine Human Magnetic 30-Plex Panel for the Luminex® platform (Invitrogen), according to the manufacturer's instructions. The concentration of IFN-γ and GM-CSF in TCM was measured with commercial ELISA kits purchased from BD Bioscience. Standards and samples were analyzed in triplicates and the mean value used for analysis.

TNF and IL-12 production by canonical and hybrid TANs were measured by intracellular staining after 6 and 24 hours of LPS stimulation (100 ng/ml), respectively. For intracellular cytokine staining, fixed TANs stained for HLA-DR were permeabilized with BD Perm/Wash™ Buffer (BD Biosciences) and then stained with the following Abs for 45 minutes at room temperature: APC anti-human TNF-α (Biolegend, clone: MAB11) and PE anti-human IL-12 (Biolegend, clone C 11.5).

Immunohistochemistry. Formalin-fixed, paraffin-embedded tumor specimens collected at the time of surgical resection were co-stained for neutrophils (MPO) and antigen-presenting cells (HLA-DR) using antibodies against HLA-DR (Biolegend; Clone L243, 1:12,000 dilution), CD66b (BD Biosciences: clone G10F5, 1:1000 dilution), and against human myeloperoxidase (MPO) (Dako; Polyclonal; 1:6000 dilution). Secondary staining was done using Leica Bond refine detection polymer (DAB) or Refine Red detection (Alk Phosphatase). All staining was performed on an automated stainer Bond III (Leica Biosystems Inc, Richmond Va.).

Statistics. All data were tested for normal distribution of variables. Comparisons between two groups were assessed with a two-tailed Student's t test for paired and unpaired data if data were normally distributed. Non-parametric Wilcoxon matched-pairs test and Mann-Whitney unpaired test were used when the populations were not normally distributed. Likewise, multiple groups were analyzed by one-way analysis of variance (ANOVA) with corresponding Tukey's multiple comparison test if normally distributed, or by the Kruskal-Wallis test with Dunn's multiple comparison test if not normally distributed. Non-parametric Spearman test was used for correlation analysis. All statistical analyses were performed with GraphPad Prism 6. p-values less than 0.05 were considered statistically significant.

The results of the experiments are now described.

Example 1: Identification of a Novel Subset of Tumor-Associated Neutrophils (TANs) Exhibiting the Composite Characteristics of Neutrophils and Antigen-Presenting Cells Characterization of tumor-associated neutrophils (TANs) revealed that the majority of TANs in early stage of non-small cell lung cancer (NSCLC) express classic neutrophil markers $CD11b^+CD15^{hi}CD66b^+MPO^+Arg1^+$ ("canonical TANs", FIG. 1B, boxes in lower left corner). However, another subpopulation of TANs that displayed a combination of neutrophil ($Arg1^+MPO^+CD66b^+CD15^+$) and antigen-presenting cell (APC) ($CD14^+HLA\text{-}DR^+CCR7^+ CD86^+$) markers was identified. This subpopulation of TANs is hereinafter referred to as "hybrid TANs" or "hybrid tumor-associated neutrophils." (FIG. 1B, boxes in upper right corner). The frequency of these newly identified "hybrid" subset of TANs varied widely in tumor tissues of cancer patients (FIG. 1C).

Figure 2C:
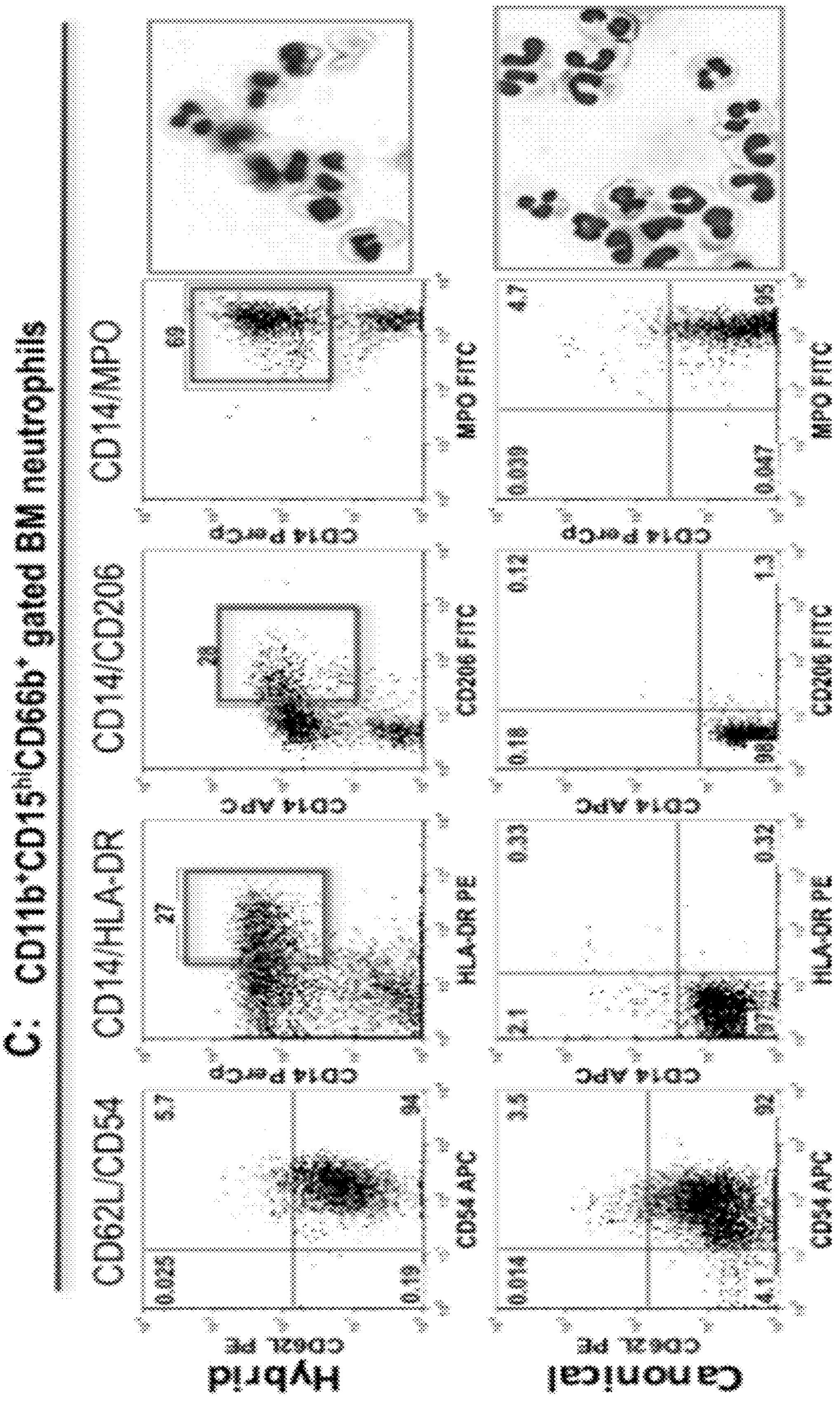

Example 2: Identification of Conditions in which the Immature Bone Marrow or Peripheral Blood Granulocytes could be Differentiated into Hybrid Neutrophils in a Large Numbers Using anti-CD15 magnetic beads, a highly enriched population of human bone marrow neutrophils (BMNs) was obtained from rib fragments that were removed from patients during routine lung cancer surgery. It was found that these BMNs exhibited a prolonged survival in vitro compared to peripheral blood neutrophils (PBNs). These $CD15^+$ BMNs expressed the myeloid/granulocytic specific markers CD11b, CD66b, Arg1, myeloperoxidase (MPO) and were mostly "band"-like immature neutrophils (FIG. 2A; FIG. 2C). Importantly, unlike blood, about 40% of these BMNs could survive in cell culture for up to 1 week (FIG. 2B). Thus, human BMNs have a prolonged lifespan in vitro, providing large quantities of cells (>50 million cells) that can be used to differentiate immature neutrophils into the hybrid neutrophils.

Several ways to differentiate immature granulocytes into the hybrid $CD14^+HLA\text{-}DR^+CD32^{hi}CD64^{hi}CD89^{hi}$ neutrophils that resemble hybrid TANs were developed. The various methods are described herein.

Incubation of BM Immature CD15 Cells with Tumor Conditioned Medium

As used herein, a "tumor conditioned medium" is medium collected from digested tumors where a high frequency of hybrid TANs was detected. In the studies described herein, tumor conditioned medium (TCM) was collected from digested tumors where a high frequency of hybrid TANs was previously detected by flow cytometry (FIG. 3A).

To obtain TCM, a single cell suspension obtained from digested tumors was cultured for 24 hours. Cell culture supernatant was collected, filtered, aliquoted and frozen down. Bone marrow granulocytes were isolated with anti-CD15 magnetic beads (FIGS. 3D-3E), washed and plated on Corning® Costar® Ultra-Low attachment multi-well plates/6 well plates at a concentration of $1\text{-}2\times10^6$/ml in complete cell culture medium supplemented with TCM (50% v/v). Cells were cultured in the presence of hybrid-inducing TCM for 5 days. The differentiated cells were then collected, washed from TCM and analyzed for the markers of hybrid neutrophils (HLA-DR, CD14, CD15, CD66b) to ensure that hybrid neutrophils were formed (FIG. 3F).

Incubation of BM Immature CD15 Cells with IFN-γ and GM-CSF

Figures 3A, 3B, 3C:
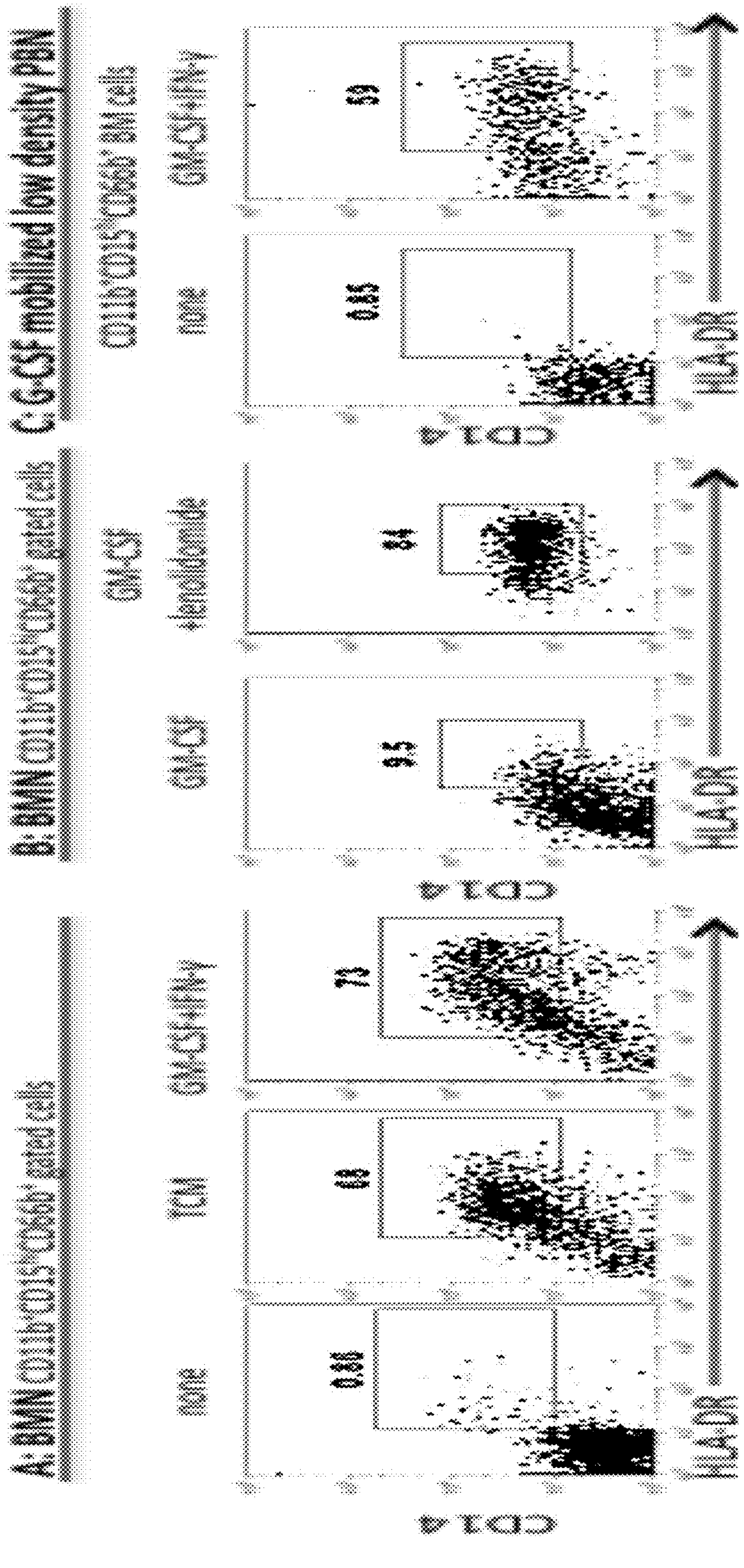
FIGS. 3A-3F are a series of plots showing the differentiation of human long-lived bone marrow (BM) immature neutrophils into the hybrid neutrophils. Neutrophils were purified from BM cell suspension using anti-CD15 magnetic beads.
Figures 3D, 3E, 3F:
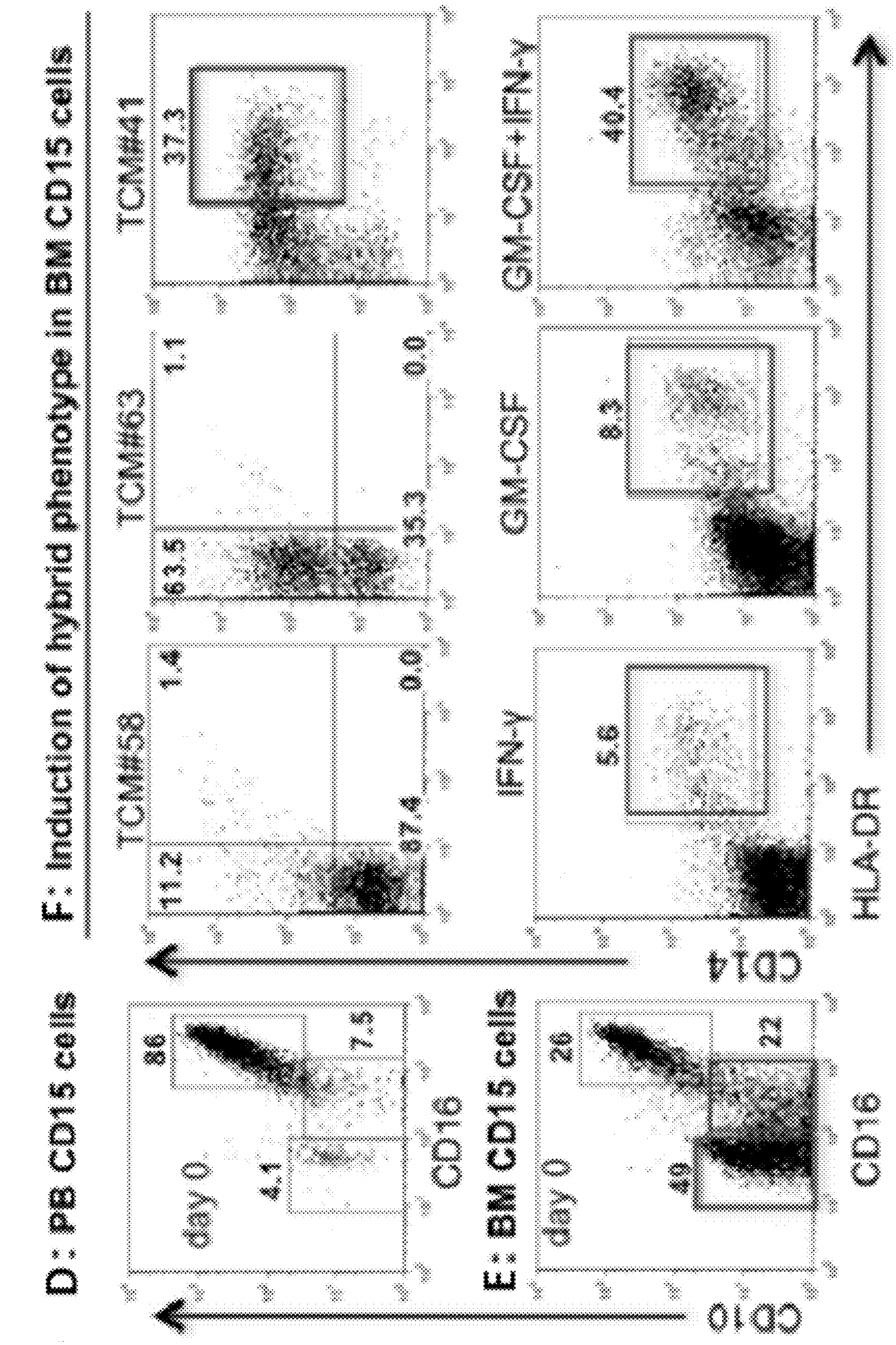

Bone marrow (BM) immature CD15 cells were incubated with IFN at low concentrations (50-100 pg/ml) (FIG. 3A). Comparative analysis of TCMs collected from digested tumors with or without hybrid TANs revealed that IFN-γ and GM-CSF are necessary factors in the tumor microenvironment for the development of the hybrid neutrophils. It was found that only IFN-γ and GM-CSF at the very low concentration of 50 pg/ml were able to induce expression both CD14 and HLA-DR on the surface of BMNs in a synergistic manner. Similar to differentiation of hybrid neutrophils with TCM described above, CD15 immature granulocytes were cultured for 5 days in the complete cell culture medium supplemented with IFN-γ and GM-CSF.

Incubation of BM Immature CD15 Cells with GM-CSF and Lenalidomide

Bone marrow (BM) immature CD15 cells were incubated with GM-CSF (50-100 pg/ml) along with the FDA approved drug lenalidomide. Lenalidomide reduces the level of the transcriptional factor Ikaros in BM immature neutrophils by inducing proteosomal degradation of this protein (Kronke et al., *Oncoimmunology.* 2014 Jul. 3; 3(7): e941742) (FIG. 3B). Similar to differentiation of hybrid neutrophils with TCM described above, the bone marrow granulocytes were isolated with anti-CD15 magnetic beads, washed and plated down to Corning® Costar® Ultra-Low attachment multi-well plates/6 well plates at concentrations of 1-2 million/ml in the complete cell culture medium supplemented with GM-CSF (100 ng/ml) and lenalidomide (3004). Cells were cultured in the presence of these factors for 6 days.

Differentiation from Peripheral Blood Immature Neutrophils

Hybrid neutrophils could be differentiated from peripheral blood immature neutrophils mobilized in peripheral blood by an administration with GM-SCF or G-CSF. Patients were treated with GM-SCF or G-CSF and peripheral blood low-density immature neutrophils were isolated by gradient separation. Cells were cultured in the presence of hybrid-inducing TCM (50% v/v) or IFN-γ and GM-CSF at concentrations between 50-100 pg/ml. At day 5, similar to BMNs, a significant portion of GM-CSF or G-CSF mobilized low-density PBNs acquired the HLA-$DR^+CD14^+$ phenotype (FIG. 3C).

Figure 4:
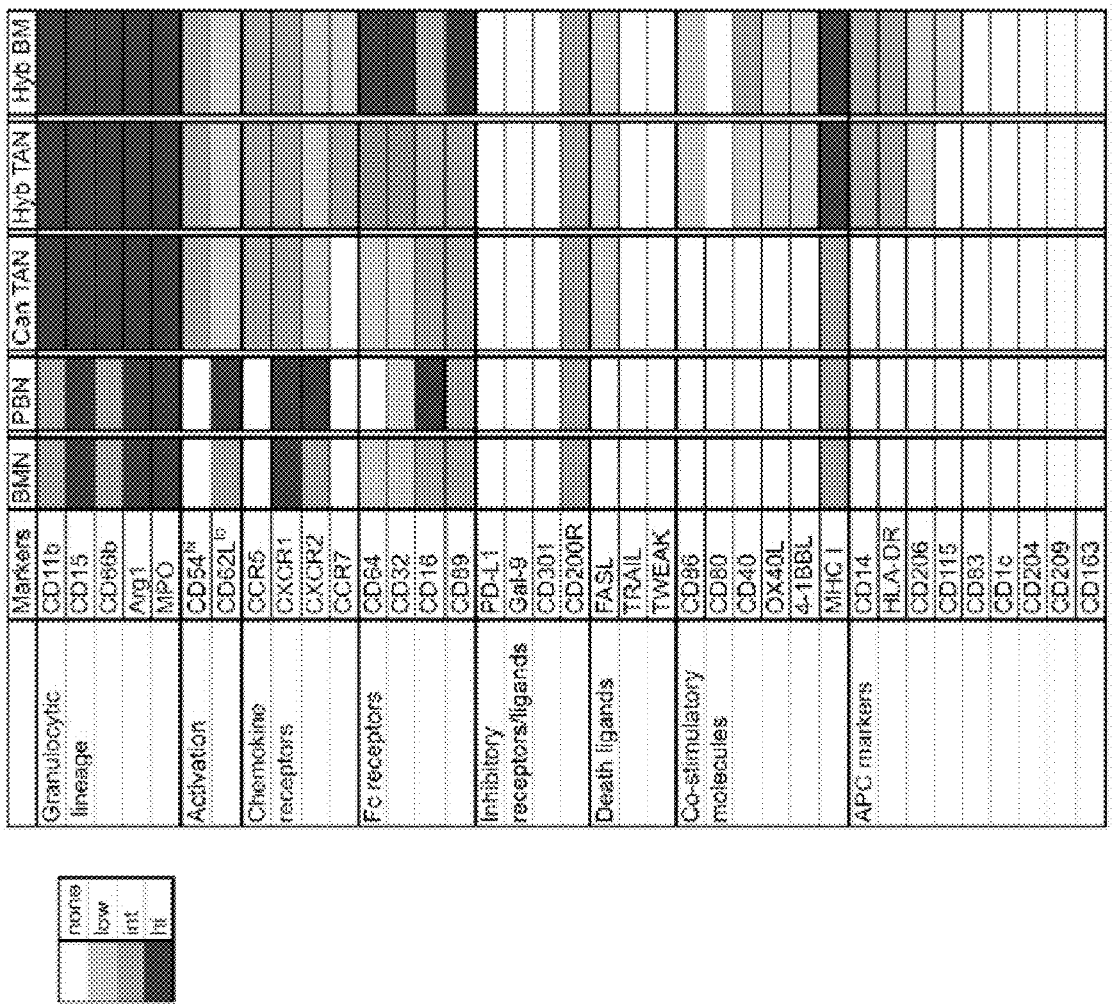
FIG. 4 is a heat map depicting the phenotype of canonical and hybrid neutrophils. The heat map compares the phenotypes of bone marrow neutrophils ("BMN"), peripheral blood neutrophils ("PBN"), canonical tumor-associated neutrophils ("Canonical TAN"), hybrid tumor-associated neutrophils ("Hybrid TAN") and bone marrow derived hybrid neutrophils ("BM Hybrid"). Neutrophils were gated on live $CD11b^+CD15^{hi}CD66b^+$ cells (PBN, BMN, canonical TAN) and $CD11b^+CD15^{hi}CD66b^+$HLA-$DR^+CD14^+$ cells (hybrid neutrophils) and further analyzed for the expression of indicated markers by flow cytometry. Expression of each marker was analyzed at least in 7 patients. The intensity key for the heat map is shown in the top left corner of FIG. 4.

The detailed phenotypic analysis described herein has revealed that hybrid neutrophils were phenotypically different from canonical neutrophils in multiple ways (summarized in FIG. 4). The differences included (1) upregulation of the MHC class II and class I molecules; (2) increased expression of T cell co-stimulatory molecules OX40L, 4-1BBL, CD86, CD40 and chemokine receptor CCR7, and (3) upregulation of the FcγRI (CD64), FcγRII (CD32) and FcαRI (CD89), which are the most potent Fc receptors for triggering antibody-dependent cell cytotoxicity (ADCC).

Example 3: Hybrid $CD14^+$HLA-$DR^+CD32^{hi}CD64^{hi}$ $CD89^{hi}$ Neutrophils Efficiently Phagocytose Bacteria and Mediate a High Level of Antibody Dependent Phagocytosis (ADP)

Figures 5A, 5B:
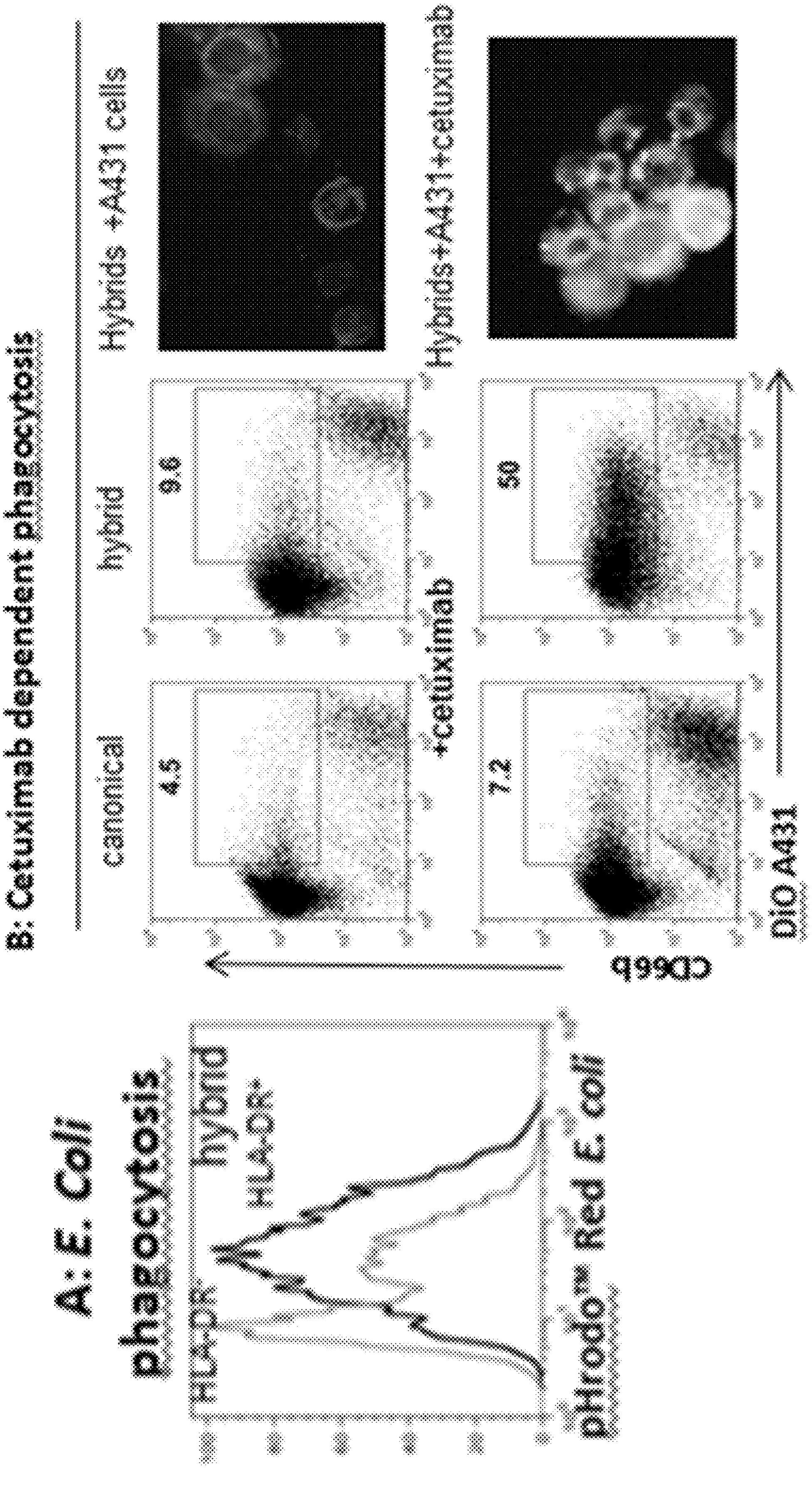
FIGS. 5A-5D are a series of plots and images showing the functional characterization of the canonical and hybrid neutrophils.
Figures 5C, 5D:
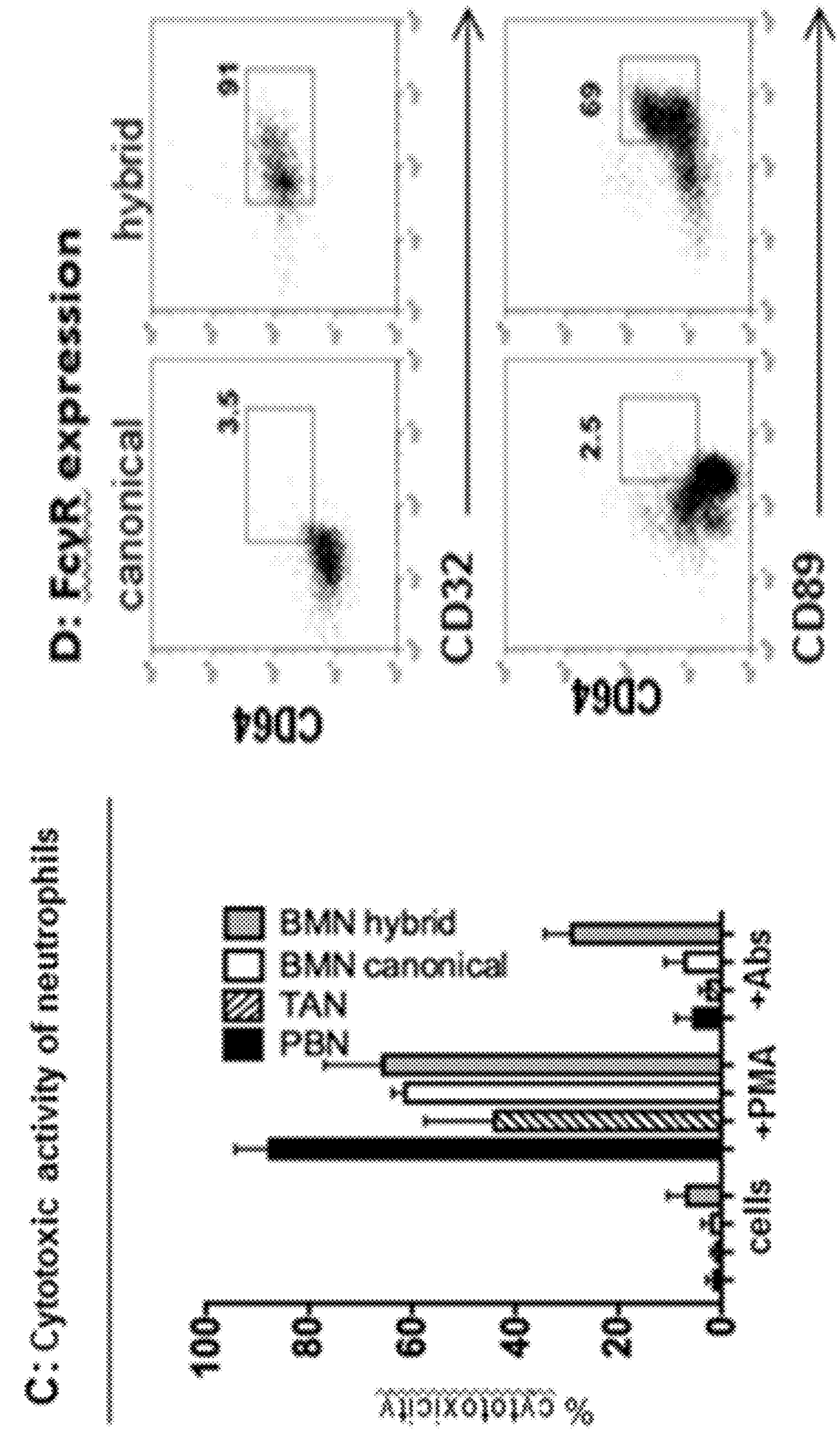

$CD32^{hi}CD64^{hi}CD89^{hi}$ hybrid neutrophils (which could be generated in large numbers from immature bone marrow or peripheral blood) are powerful effector cells that trigger sufficient removal of tumor cells or infectious pathogens through ADP or ADCC. The support for this claim comes from a comparative analysis of canonical and hybrid neutrophils that revealed that hybrid neutrophils are characterized by (1) augmented ability to phagocytose bacteria (FIG. 5A); (2) expression of very high levels of FcγRI (CD64), FcγRII (CD32) and FcαR (CD89) (FIG. 5D) (of note, the high affinity FcγRI/CD64 represents the most potent neutrophil FcγR for induction of ADCC (Valerius et al., *Blood.* 1993 Aug. 1; 82(3): 931-939)); (3) increased ability to mediate the high level of antibody-dependent phagocytosis (FIG. 5B); and (4) ability to mediate ADCC (FIG. 5C).

Figures 6A, 6B:
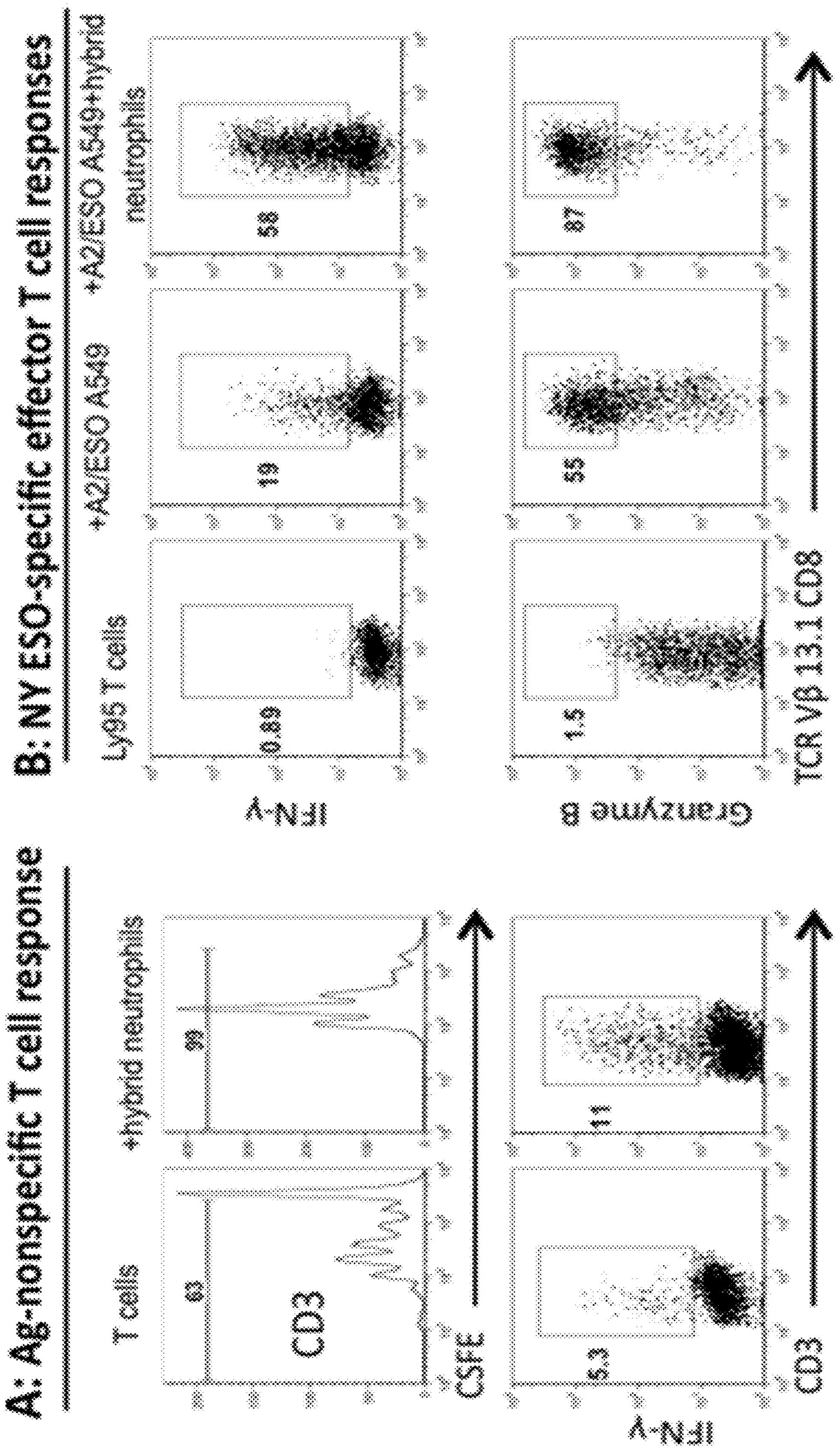
FIGS. 6A-6M are a series of plots and images showing the effect of canonical and hybrid neutrophils on T cell responses.
Figures 6C, 6D:
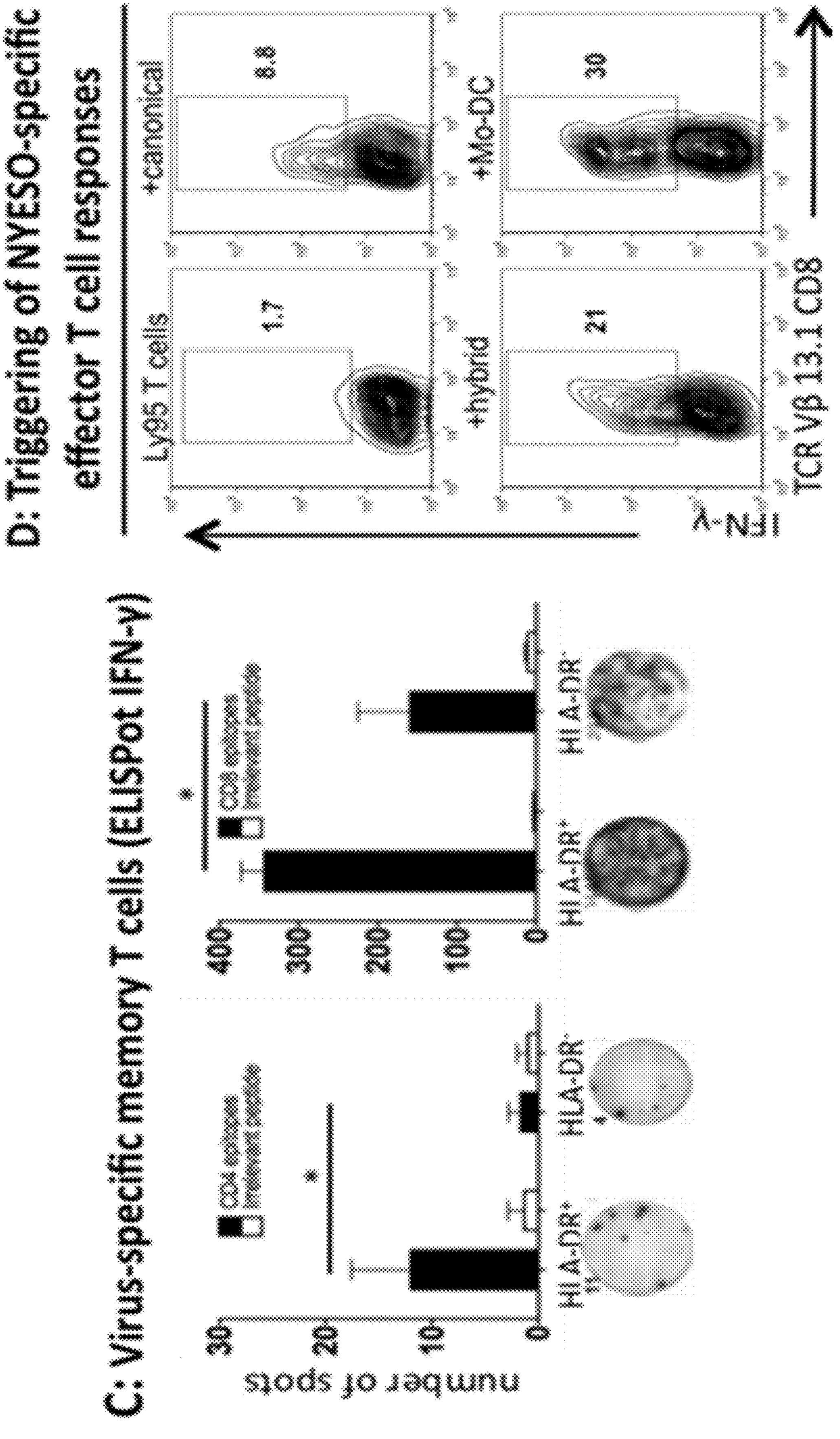
Figures 6E, 6F, 6G, 6H:
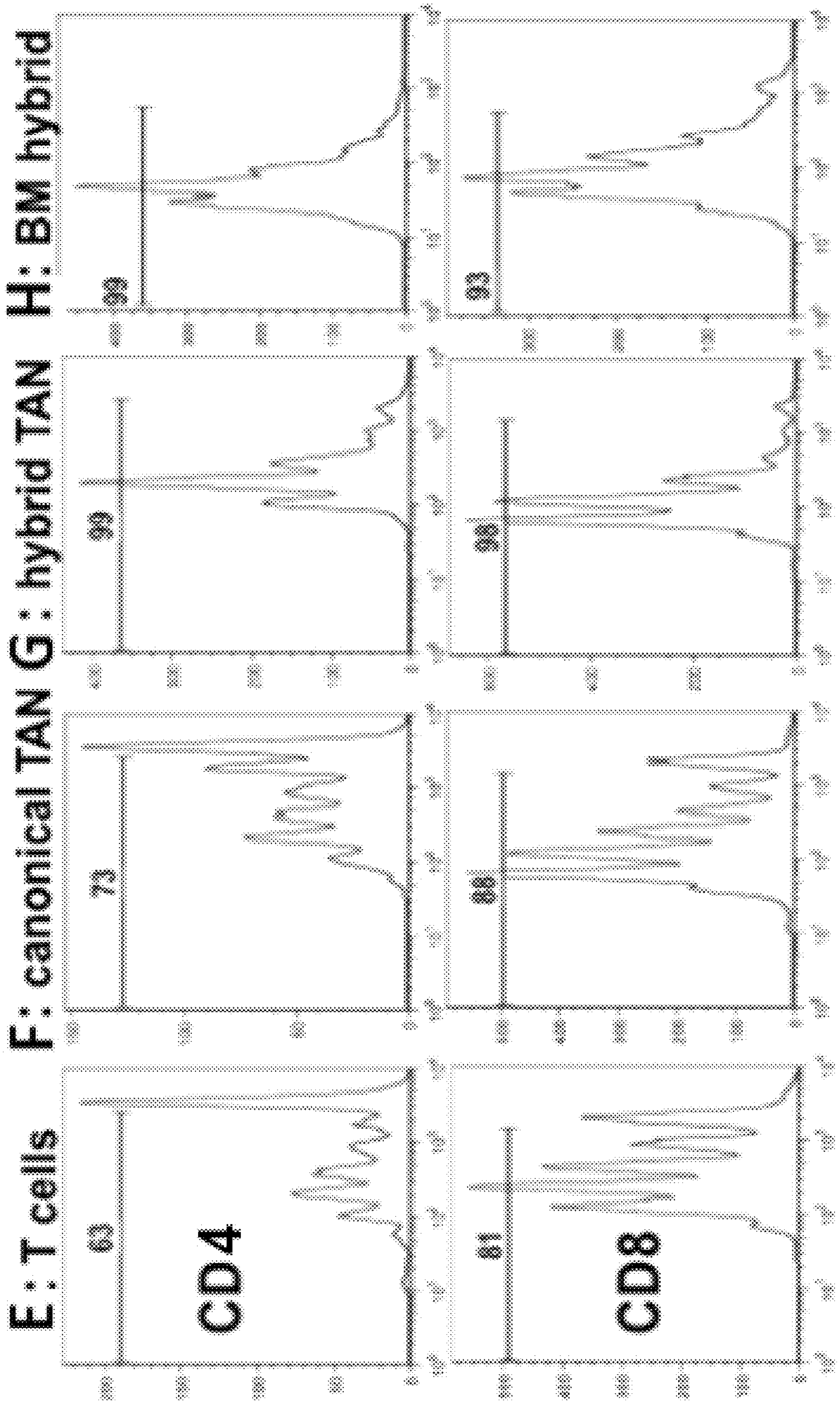
Figures 6I, 6J, 6K, 6L:
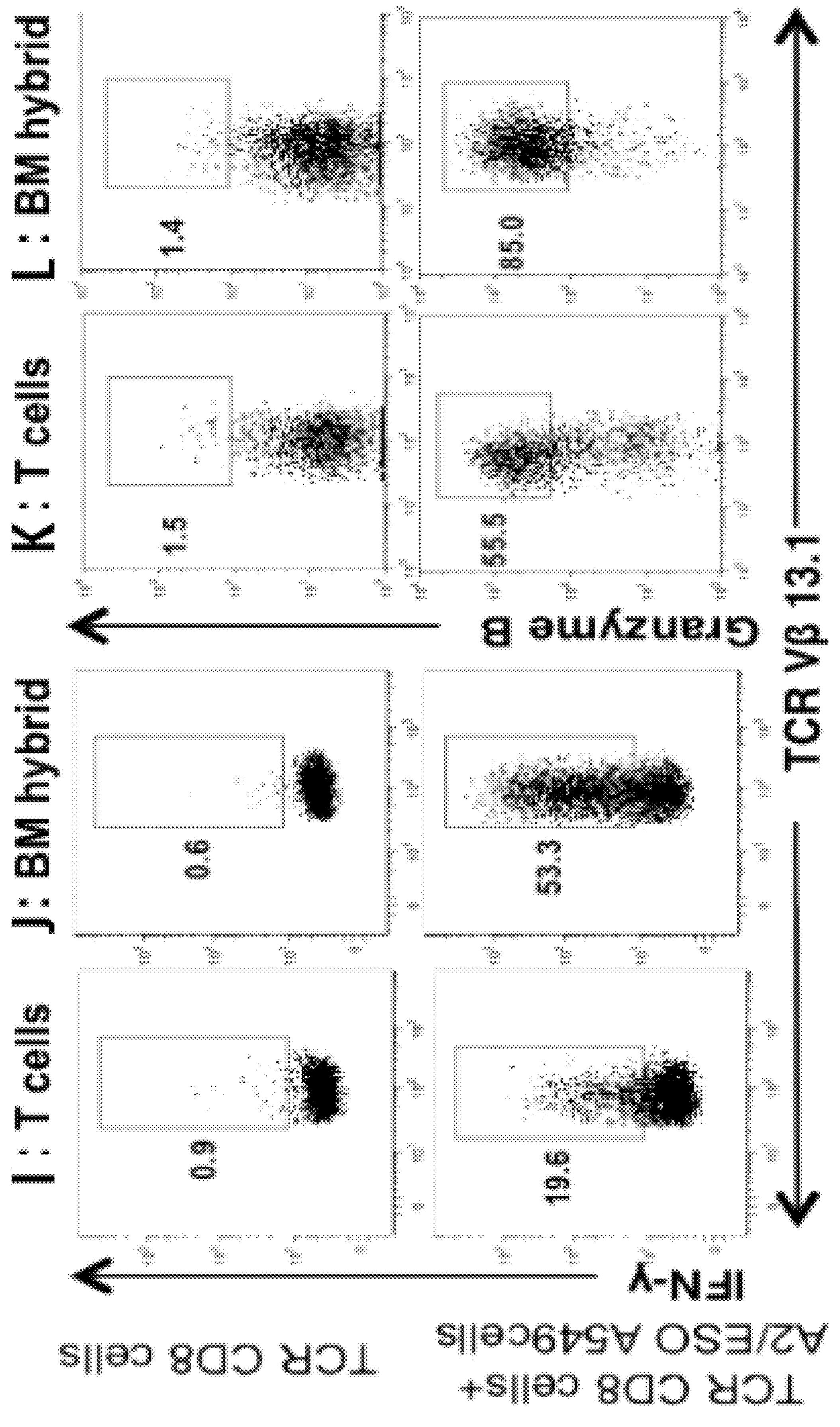
Figure 6M:
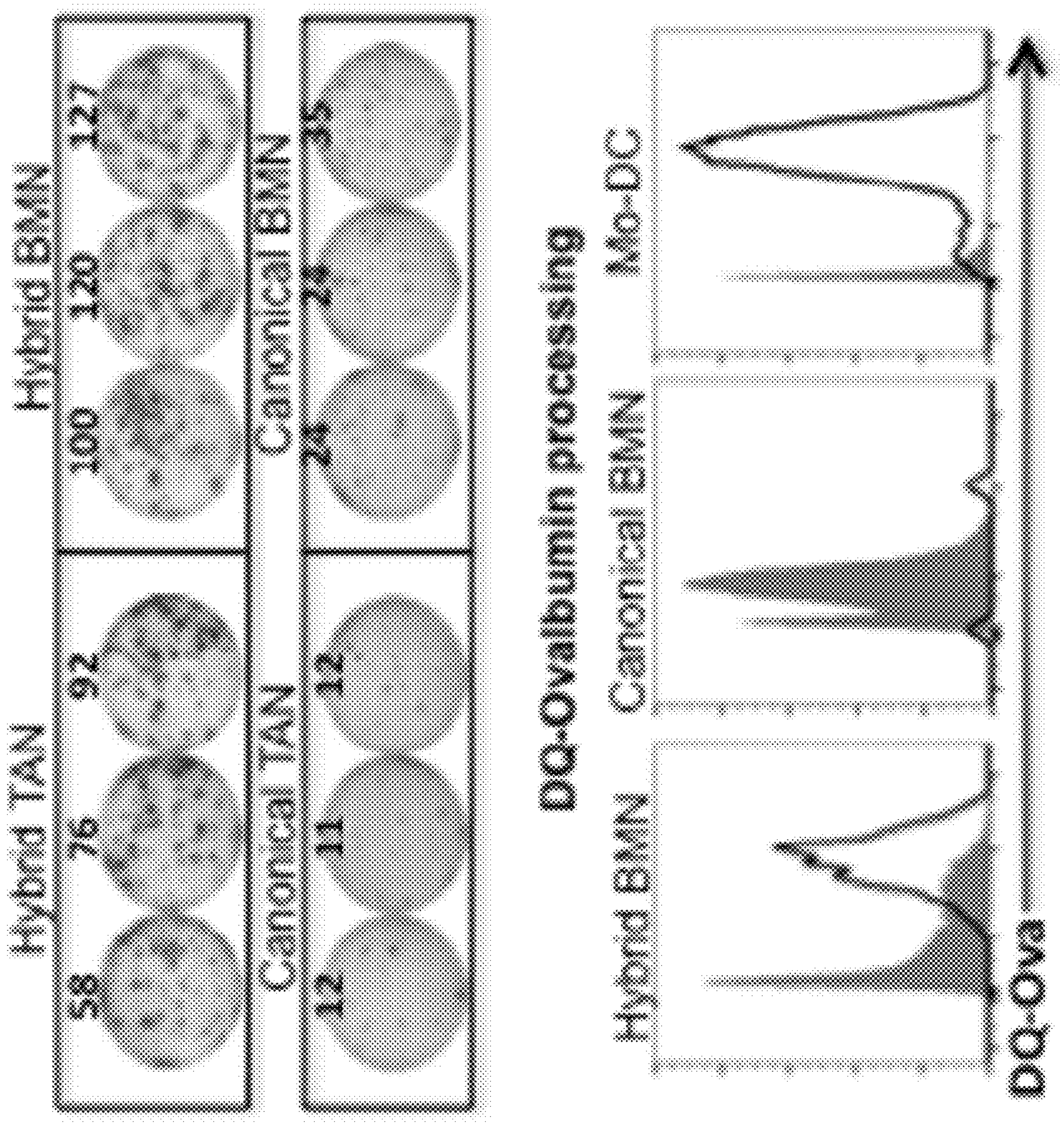

Example 4: Hybrid Neutrophils Trigger and Stimulate Effector T Cell Responses Results of the studies described herein demonstrate that tumor or BM-derived hybrid neutrophils were able to: (1) dramatically augment proliferation of naïve resting T cells stimulated with anti-CD3/CD28 Abs compared to canonical neutrophils (FIG. 6A; FIGS. 6E-6H); (2) augment response of anti-tumoral effector T cells (FIG. 6B; FIGS. 6I-6L); (3) present viral antigens to autologous memory CD8 and CD4 cells (FIG. 6C); and, (4) cross present tumor antigens to cytotoxic T cells (FIG. 6D; FIG. 6M). Given these findings, it is expected that the expansion and use of hybrid neutrophils in humans can significantly augment the efficacy of therapeutic antibodies and boost anti-tumor and anti-infectious immunity.

Figures 7A, 7B:
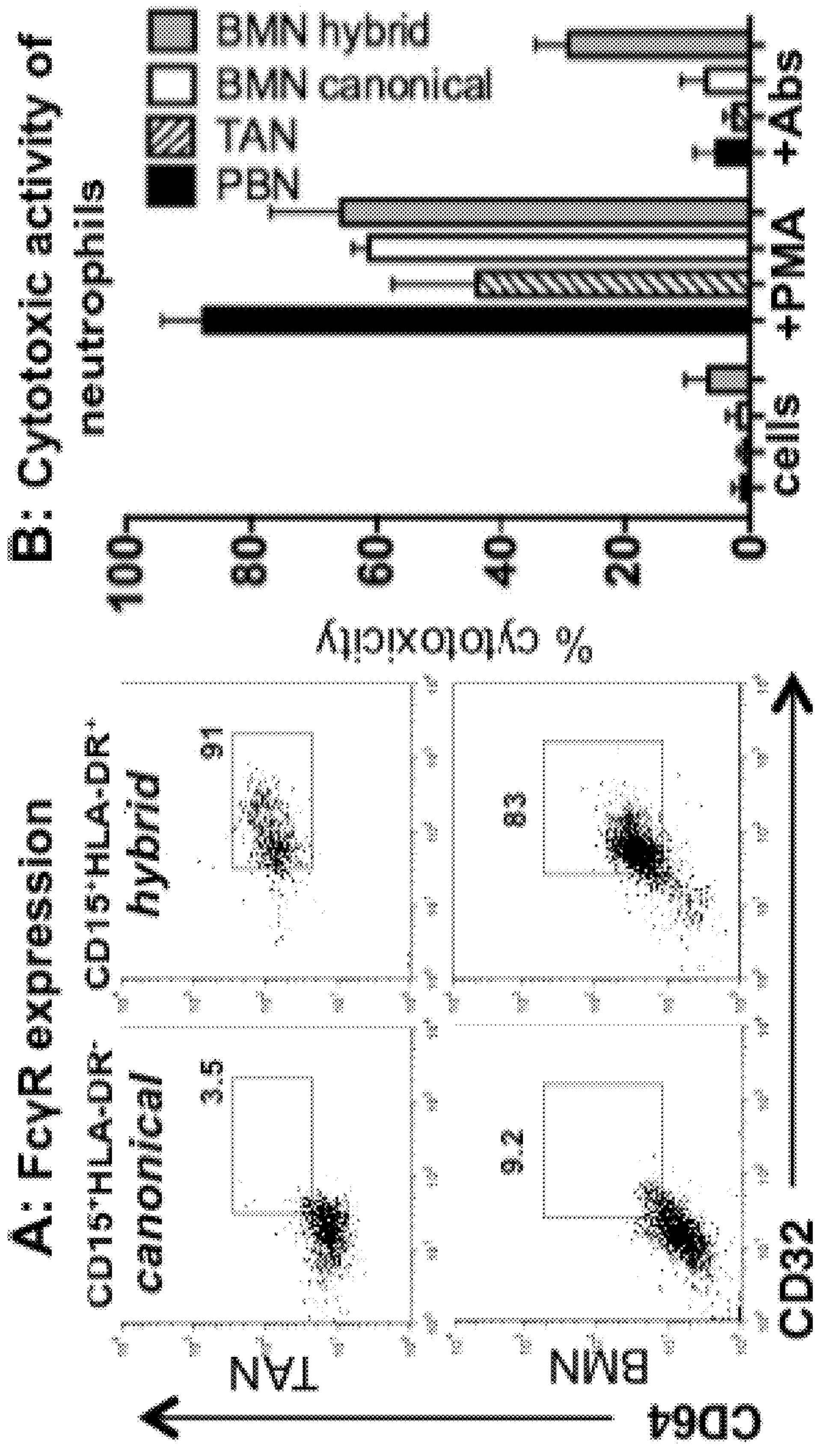
FIGS. 7A-7B are plots showing the expression of FcγRI (CD64) and FcγRII (CD32) and neutrophil tumoricidal activity.

Example 5: Hybrid Neutrophil Cytotoxicity Triggered by Tumor Antigen Specific Antibodies Comparative analysis of BM and tumor-derived canonical and hybrid neutrophils revealed that hybrid neutrophils are characterized by expression of high levels of FcγRI (CD64), FcγRII (CD32) and FcaR (CD89) (FIG. 7A, FIG. 5D). It was tested whether the elevated levels of these receptors, particular the high affinity FcγRI, significantly enhanced ADCC. To study tumor cell killing by neutrophils in vitro, a GFP expressing A549 tumor cell line (lung carcinoma) was generated. Using this cell line as a target, it was found that PBNs, TANs and canonical BMNs, were unable to directly kill tumor cells unless a non-physiologic activator, such as phorbol ester was added (FIG. 7B). These cells were also not able to kill tumor cells opsonized with the anti-EGFR monoclonal antibody (mAb) (cetuximab). Interestingly, however, the BM-derived hybrid neutrophils showed significant antitumor activity when cultured with anti-EGFR mAbs-opsonized target cells (FIG. 7B, right bars).

To characterize the mechanisms of Cetuximab-induced tumor cell killing by BM hybrid neutrophils, these cells were incubated with A549 tumor cells opsonized with anti-EGFR Abs with or without different inhibitors. Tumor cell death was quantified after 24 hours of co-culture as described in FIG. 7B.

Effector Mechanisms of Hybrid Neutrophil Mediated ADCC

To identify if antibody-dependent phagocytosis (ADP) by hybrid neutrophils is involved in the elimination of opsonized target cells, anti-EGFR Ab-coated GFP-A549 cells are co-cultured with red-fluorescent dye DiI-labeled BM-derived hybrid neutrophils for 4 and 18 hours. Phagocytosed A549 cells are identified as both GFP+ and DiI+ cells by flow cytometry. To determine the role of reactive oxygen species (ROS) dependent mechanisms, an inhibitor of the NADPH oxidase complex (apocynin) is added to the cytotoxicity assay. To assess the role of superoxide anion $O_2$—, hydrogen peroxide, or hypochlorous acid (HOCl) in hybrid neutrophil-mediated killing, cytotoxic assays are performed in the presence of their specific inhibitors: superoxide dismutase, catalase, and taurine, respectively. The ability of each neutrophil subtype to produce ROS following the incubation with opsonized A549 tumor cells using Amplex Red or CM-H2DCFDA in parallel with the cytotoxicity assays are compared as described (Eruslanov et al., 2010. *Methods Mol Biol.* 594: 57-72). To identify whether the generation of reactive nitrogen intermediates by neutrophils is involved in neutrophil mediated tumor cell killing, the nitric oxide synthase inhibitor L-NMMA is added to the cytotoxic assay.

Contribution of FcγR Signaling to Hybrid Neutrophil Mediated ADCC

It has been demonstrated that cross-linking of Fc receptors triggers activation of the PI3K and RAS-ERK pathways which then play a critical role during NK cell and macrophage-mediated ADCC (Garcia-Garcia et al., *J Immunol.* 2009 Apr. 15; 182(8): 4547-4556; Joshi et al., *PLoS One.* 2009; 4(1): e4208; Jiang et al., Nat Immunol. 2000 November; 1(5): 419-425; Wei et al., *J Exp Med.* 1998 Jun. 1; 187(11): 1753-1765). Thus, the hypothesis that these signaling pathways are activated and necessary for triggering the tumoricidal activity of hybrid neutrophils can be tested. Activation of RAS-ERK pathway is assessed by measuring the phosphorylation of MEK1/2 and Erk1/2 in hybrid neutrophils stimulated with opsonized GFP-A549 tumor cells for 15 minutes. Cells are fixed with BD PhosFlow Fix Buffer™ and stained for intracellular ERK1/2 (pT202/pY204) and MEK1 (pS218)/MEK2 (pS222) Abs (BD Phosflow™). Levels of MEK and ERK phosphorylation are quantified by flow cytometry on gated GFP-negative neutrophils. In order to examine whether the activation of the PI3K and RAS-ERK pathways are important during neutrophil-mediated ADCC, the hybrid neutrophils are pre-treated with the specific inhibitors wortmannin (PI3K inhibitor), PD98059 (MEK1/2 inhibitor) or LY294002 (PI3K inhibitor). In order to determine what class of Fc receptors on hybrid neutrophils triggers the high level of ADCC, BM-derived hybrid neutrophils are pre-incubated with blocking Abs against CD32 or CD64 (Biolegend) and added to opsonized A549 cells.

Hybrid TANs Killing by ADCC

To evaluate the ability of canonical and real hybrid TANs to mediate ADCC, TAN subsets are isolated from tumors and mixed with anti-EGFR Ab opsonized A549 tumor cells at different ratios, as described above.

Without being bound by specific theory, it is expected that BM and tumor-derived hybrid neutrophils will mediate high levels of ADCC by antibody-dependent phagocytosis of opsonized A549 cells and by subjecting them to oxidative damage. Given that the high affinity FcγRI/CD64 represents the most potent neutrophil FcγR for induction of ADCC, it is anticipated that triggering of FcγRI/CD64 signal pathway will lead to activation of tumoricidal activity of hybrid neutrophils. If the hybrid neutrophils are not able to phagocytose the opsonized A549 cells or do not use ROS as their primary killing mechanism, other extracellular cytotoxic mechanisms such as NET (neutrophil extracellular traps) formation after binding opsonized tumor cells will be investigated. NETs are visualized by fluorescence imaging of extracellular DNA stained with Sytox Green. Without intending to be bound by specific theory, it is also possible that alternative non-oxidative pathways can be involved in tumor cell lysis by hybrid cells. This can be explored by using inhibitors of different serine proteinases and peptide defensins in the cytotoxic assay performed. Antibodies that block possible death receptor/death receptor ligands, including anti-TRAIL and anti-FASL antibodies, will be used. It is possible that hybrid TANs will not show the same type of high tumoricidal activity as BM hybrid cells during ADCC. This will be useful and important information, however, it will not diminish the potential clinical value of BM-derived hybrid neutrophils that can be generated in large numbers from lung cancer patients for potential treatment with therapeutic antibodies.

Example 6: Clinical Potential of Hybrid Cells Generated from BM to Mediate ADCC In Vivo Epidermal growth factor receptor (EGFR) is commonly overexpressed in NSCLC (Brabender et al., *Clin Cancer Res.* 2001 July; 7(7): 1850-1855) and targeting this receptor is a validated approach to treating cancer. However, the efficacy of therapeutic anti-EGFR monoclonal antibody (mAbs) (cetuximab)-based monotherapy is poor (Liu et al., *Cancer Chemother Pharmacol.* 2010 April; 65(5): 849-861. 47). Combined treatment of tumors with G-CSF/GM-CSF to induce the recruitment of effector neutrophils from bone marrow and therapeutic mAbs was used in several clinical trials to enhance the efficacy of cetuximab through ADCC (Repp et al, *Br J Cancer.* 2003 Dec. 15; 89(12): 2234-2243; Pullarkat et al., *Cancer Immunol Immunother.* 1999 April; 48(1): 9-21; Cartron et al., *J Chn Oncol.* 2008 Jun. 1; 26(16): 2725-2731). However, these trials only showed limited therapeutic effects, indicating that improvement of neutrophil-mediated Ab therapy is required (Fury et al, *Cancer Immunol Immunother.* 2008 February; 57(2): 155-163; Repp et al., *Br J Cancer.* 2003 Dec. 15; 89(12): 2234-2243). It was hypothesized that $CD64^{hi}CD32^{hi}$ hybrid neutrophils (which could be generated in large numbers from bone marrow) are powerful effector cells to trigger sufficient ADCC.

Figures 8A, 8B:
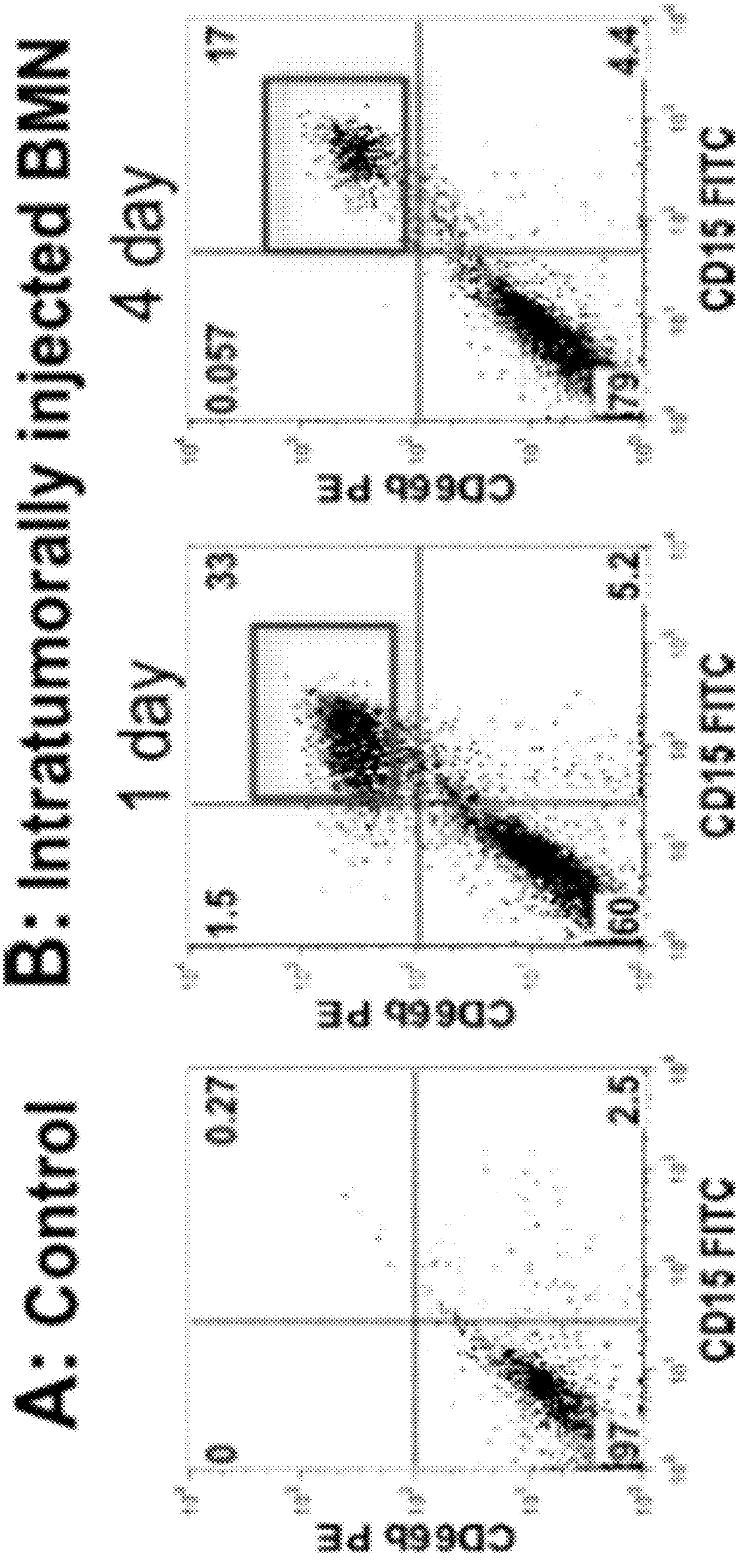
FIGS. 8A-8B are plots showing results of a murine model to study the human neutrophils mediated ADCC in vivo.
Figure 10:
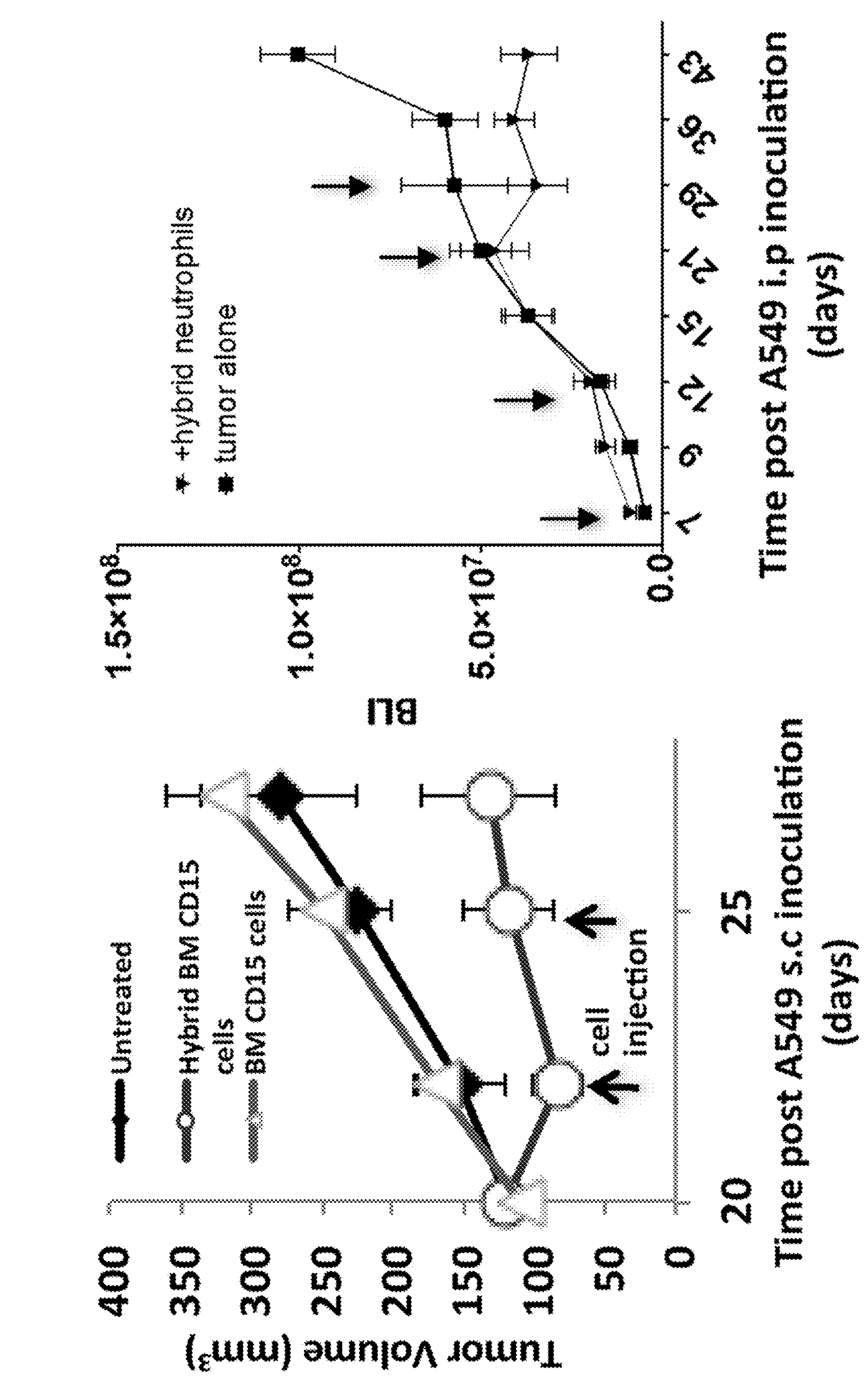
FIG. 10 is a set of graphs showing tumoricidal activity of hybrid BM neutrophils in vivo. A549 tumor cells were injected subcutaneously ($2\times10^6$ cells/mouse) or intraperitoneally ($1\times10^6$ cells/mouse). Arrows show when hybrid neutrophils were injected intratumorally. Sizes of subcutaneous tumors were measured with calipers. The tumor growth in the peritoneum was monitored by measuring bioluminescence (BLI) following intraperitoneal transplantation of Luciferase-expressing A549 tumor cells.

It has been difficult to study human neutrophils in any animal models because after systemic injection of human peripheral neutrophils, the cells are either rapidly destroyed or are trapped in the lung and do not localize to the tumors. However, this limitation was overcome herein by injecting $10^6$ human neutrophils intratumorally into established human lung cancer cell line-derived tumors (100 $mm^3$ A549 lung cancer xenografts) in NOD/SCID/γ-chain knockout (NSG) mice. It was found that injected BM neutrophils (but not blood neutrophils) were still present in A549 tumors 4 days post-injection (FIGS. 8A-8B). It has been previously demonstrated that cetuximab is capable of activating ADCC activity against A549 lung cancer cells (Kurai et al., *Clin Cancer Res.* 2007 Mar. 1; 13(5): 1552-1561). Thus, this model allowed the cetuximab-induced tumoricidal effect of hybrid neutrophils to be studied in vivo (FIG. 10).

NSG mice with established A549 flank tumors (100-200 $mm^3$) can be studied. The ability of BM-derived hybrid neutrophils to mediate ADCC in vivo using the cetuximab can be characterized. Briefly, cetuximab is injected IV into tumor-bearing mice. Next, $10^7$ BM-derived hybrid or canonical neutrophils are injected intratumroally (IT). All IV injections are performed 2 hours before the IT injections to allow antibody binding to tumors. Tumor size over 5 days is measured. Table 1 shows the groups needed in this study. Ten (10) mice per group (enough to enable detection of 25% differences in tumor size-based on years of previous similar studies and consultation with a biostatistician) are studied. Compared to a control group (Group 1), little effect of antibody alone is expected (Group 2). No effect from canonical BMN (groups 3 and 4) or the hybrid BMN without cetuximab is expected (Group 5). If the hypothesis is correct, the most dramatic effects will be observed in Group 6, where the hybrid BMN is highly active against opsonized tumor and leads to tumor regression.

TABLE 1

Experimental groups to study ADCC in vivo

| | IV Injection | IT injection |
|---|---|---|
| Group 1 | saline | saline |
| Group 2 | cetuximab | saline |
| Group 3 | saline | canon BMN |
| Group 4 | cetuximab | canon BMN |
| Group 5 | saline | hybrid BMN |
| Group 6 | cetuximab | hybrid BMN |

If ADCC is not observed in vivo, it will be confirmed first that tumors are coated with cetuximab by harvesting tumors after injection and staining with anti-human IgG to detect cetuximab. If very low levels of Ab penetration are observed, cetuximab will be injected intratumorally. Without being bound by specific theory, binding of cetuximab to the receptor may result in sufficient internalization of the antibody-receptor complex that leads to downregulation of EGFR expression (Patel et al., *Anticancer Res.* 2007 September-October; 27(5A): 3355-336663). The dissociation from FcRs is also possible. To determine these effects, the level of bound cetuximab on EpCam+ cells in A549 lung cancer xenografts is measured at different time points following IV and IT injection of cetuximab in NSG mice. For this purpose, tumors at 1, 4, 6 and 24 hours are harvested and enzymatically digested. The tumor single cell suspensions are stained for EpCam (to detect tumor cells) and anti-human IgG (Fc) secondary Ab (to detect bound cetuximab). If substantial downregulation of EGFR in tumors is observed, the injections of cetuximab daily are repeated. Alternatively, other therapeutic antibodies against EGFR, such as necitumumab and panitumumab, that may better penetrate tumor tissue and have a lower rate of antibody-receptor complex internalization, are used.

Figures 11A, 11B, 11C:
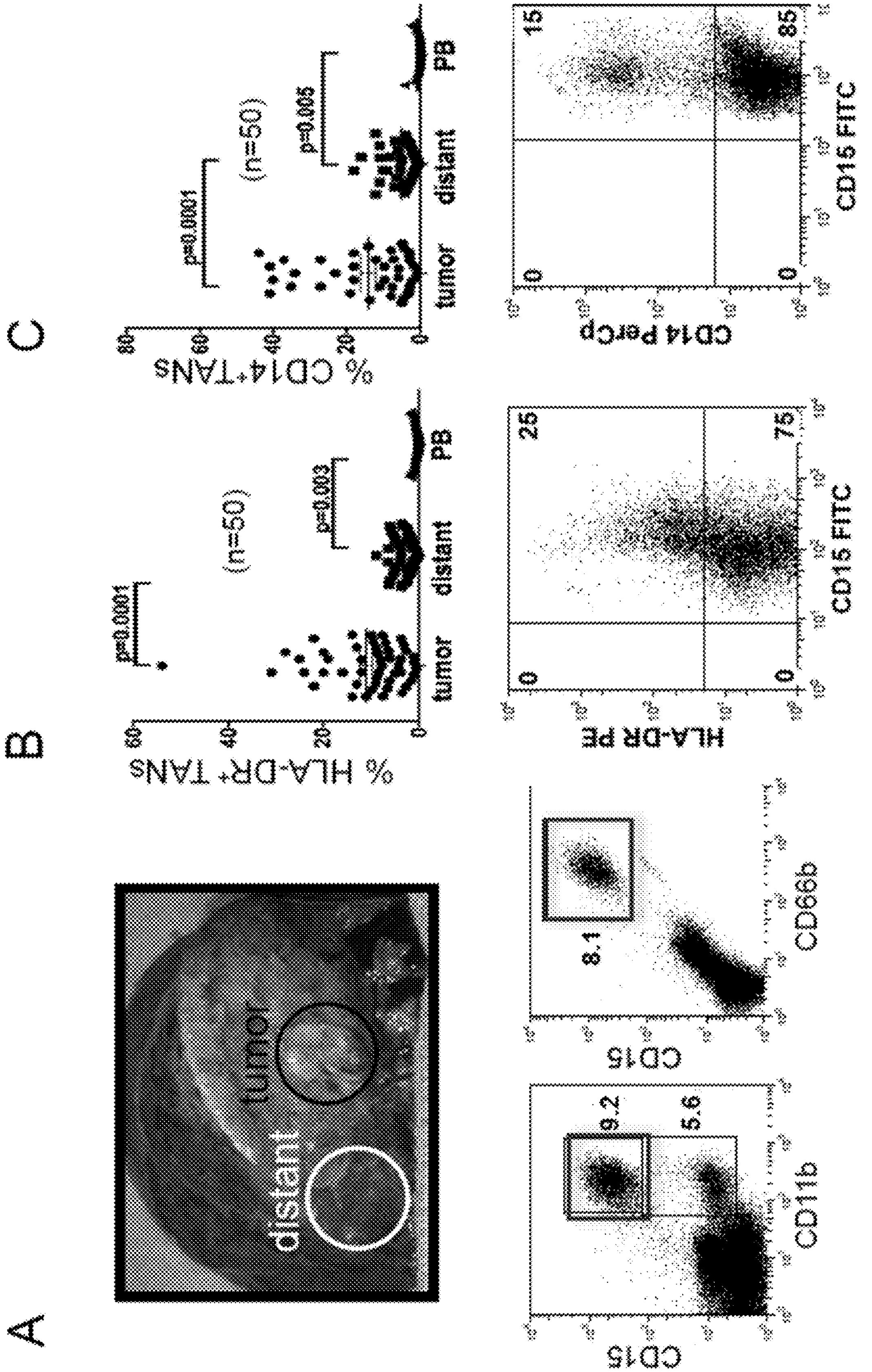
Figures 11D, 11E, 11F:
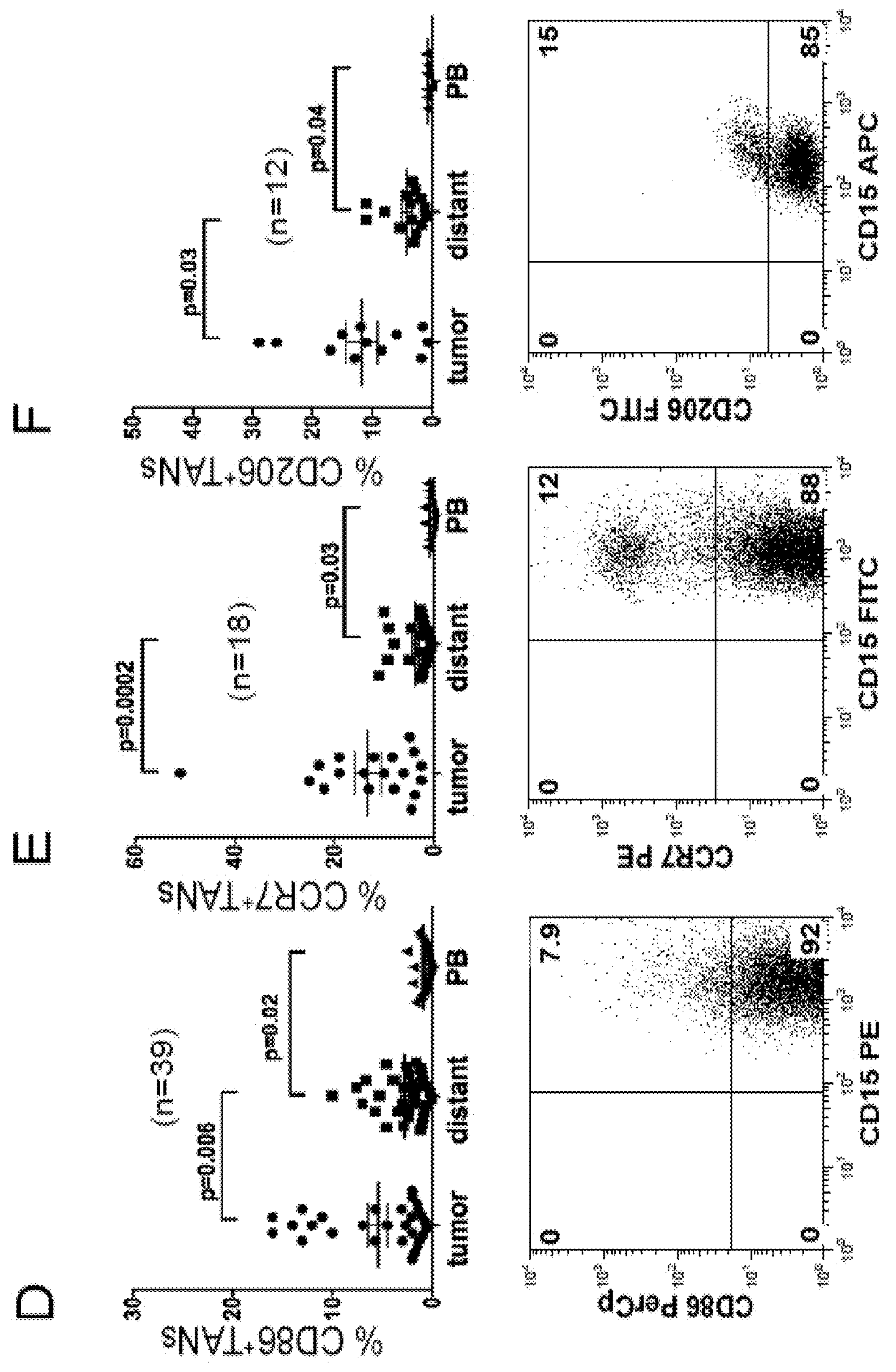
Figures 13A, 13B:
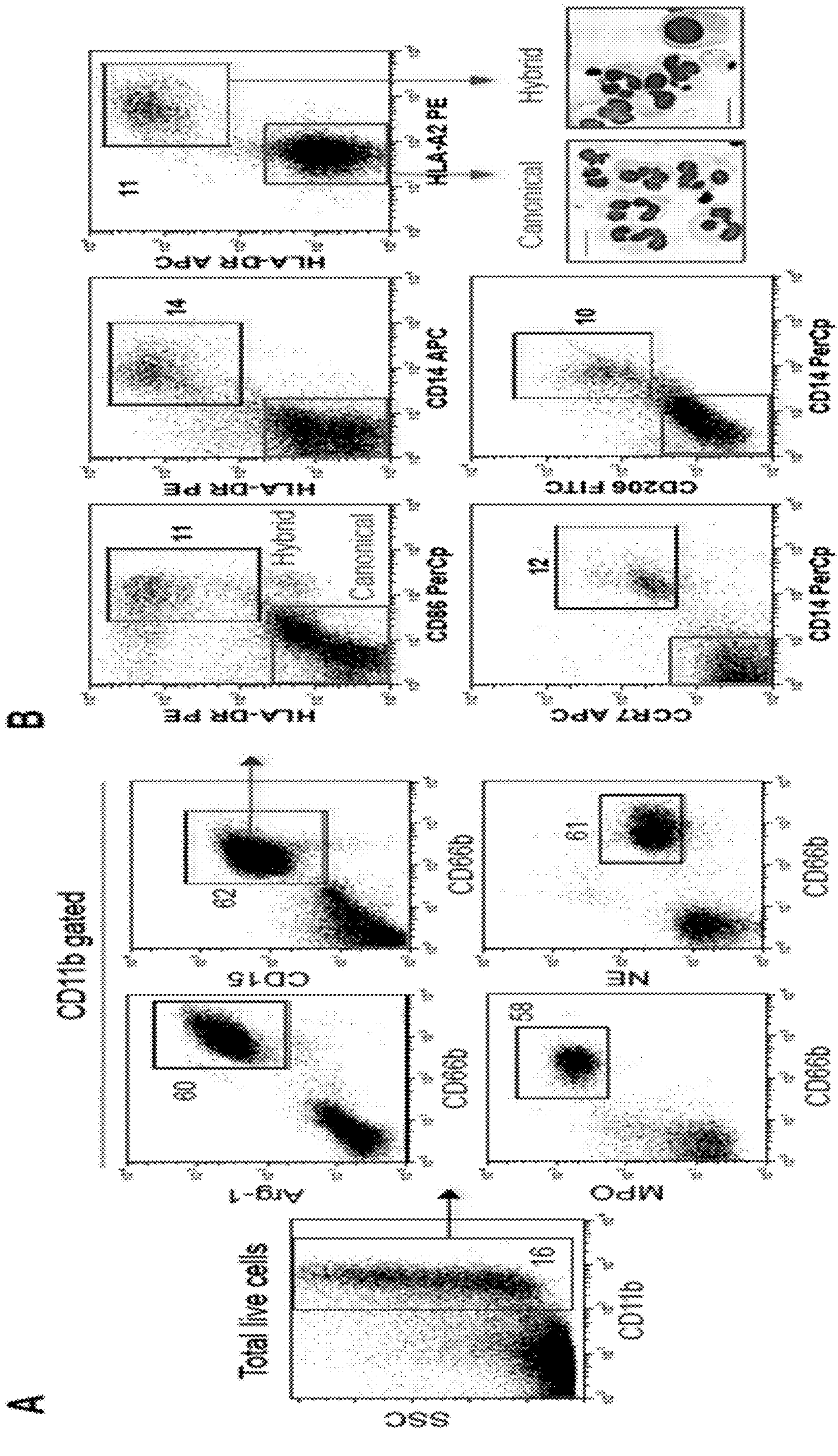
FIGS. 13A-13G are a series of graphs and images showing a subset of TANs with hybrid characteristics of neutrophils and APCs.

Example 7: Early-Stage Human Lung Cancers Accumulate a Neutrophil Subset with a Composite Phenotype of Granulocytes and APCs The expression of APC surface markers was measured on neutrophils from three locations: lung cancer tissue, adjacent (within the same lobe) lung parenchyma (termed "distant tissue"), and peripheral blood (FIG. 11A). Phenotypic analysis of 50 random patients with stage I-II non-small cell lung cancer (NSCLC) was performed. Detailed characteristics of all patients involved in this study are shown in FIG. 12. Fresh tissue was digested using defined conditions that minimize enzyme-induced ex vivo effects on the viability, premature activation, phenotype, and function of neutrophils (Quatromoni et al., *J. Leukoc. Biol.* 2015 1, 201-209). TANs were previously characterized as $CD11b^+CD15^{hi}CD66b^+$ $MPO^+Arg1^+CD16^{int}IL\text{-}5R\alpha^-$ cells (Eruslanov et al., 2014 *J Clin. Invest.* 12, 5466-5480). Importantly, all $CD66b^+$ $CD11b^+$ cells also expressed the other neutrophil/myeloid cell markers CD15, MPO (myeloperoxidase), Arg-1(arginase-1), and NE (neutrophil elastase) at very high levels (FIG. 13A, inset boxes) and thus could be segregated from other $CD15^{lo}MPO^{lo}NE^{lo}Arg^-$ non-granulocytic $CD11b^+$ myeloid cells. Since there was a high concordance among the selected neutrophil markers, for the present study TANs were defined as $CD15^{hi}CD66b^+CD11b^+$ cells. Analysis revealed that the majority of neutrophils from lung tumors, termed "canonical TANs," expressed only these classic neutrophil markers (FIG. 13A and FIG. 11A). However, TANs with surface expression of additional markers normally expressed on APCs were also identified, specifically human leukocyte antigen (HLA)-DR, CD14, CD206, CD86, and CCR7 (FIGS. 11B-11F). These receptors were completely absent in peripheral blood neutrophils (PBNs). The "distant tissue" neutrophils also expressed these APC markers, albeit at much lower levels in comparison with TANs.

Figures 13C, 13D, 13E:
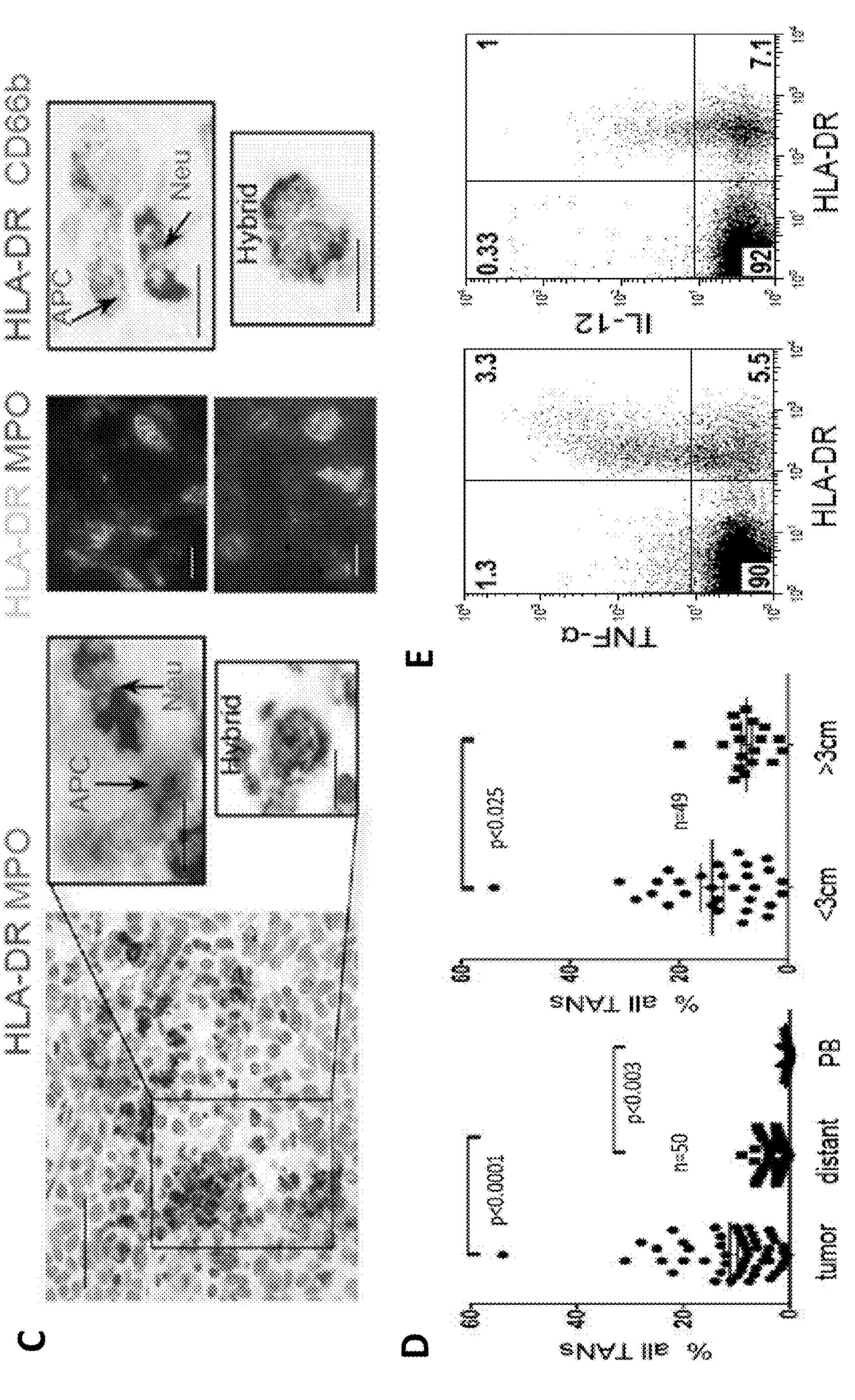

Further analysis revealed that the APC markers ($CD14^+$ $HLA\text{-}DR^+HLA\text{-}ABC^{hi}CCR7^+CD86^+CD206^+$) were co-expressed on a unique subset of $CD11b^+CD66b^+CD15^{hi}$ TANs (FIG. 13B and FIG. 1B), exhibiting a composite phenotype of canonical neutrophils and APCs. As used herein, this subset is termed "APC-like hybrid TANs", "hybrid TANs" or "hybrid tumor-associated neutrophils." This population of hybrid TANs expressed some markers of the APC phenotype (e.g., CD14, HLA-DR, CCR7, CD86, and CD206) but lacked other defining markers of "professional APC" such as CD209, CD204, CD83, CD163, CD1c, and CCR6. Of note, the expression of CD206, CCR7, and CD86 varied, whereas there was a consistent co-expression of HLA-DR and CD14 on hybrid TANs. Cytospins prepared from flow-sorted $HLA\text{-}DR^-$ canonical and $HLA\text{-}DR^+$ hybrid TANs revealed that some of the hybrid TANs had round and oval nuclear shapes in comparison with the classic nuclear segmentation of canonical TANs (FIG. 13B). Histological review of lung tumors also revealed "double-positive" $MPO^+HLA\text{-}DR^+$ and $CD66b^+$ $HLA\text{-}DR^+$ TANs that were scattered throughout lung tumors (FIG. 13C). Additionally, a small but clearly distinguishable population of $HLA\text{-}DR^+CD15^{hi}CD66b^+$ $CD11b^+$ cells were detected in the draining lymph nodes of several lung cancer patients (FIG. 11G).

Figures 11G, 11H, 11I, 11J:
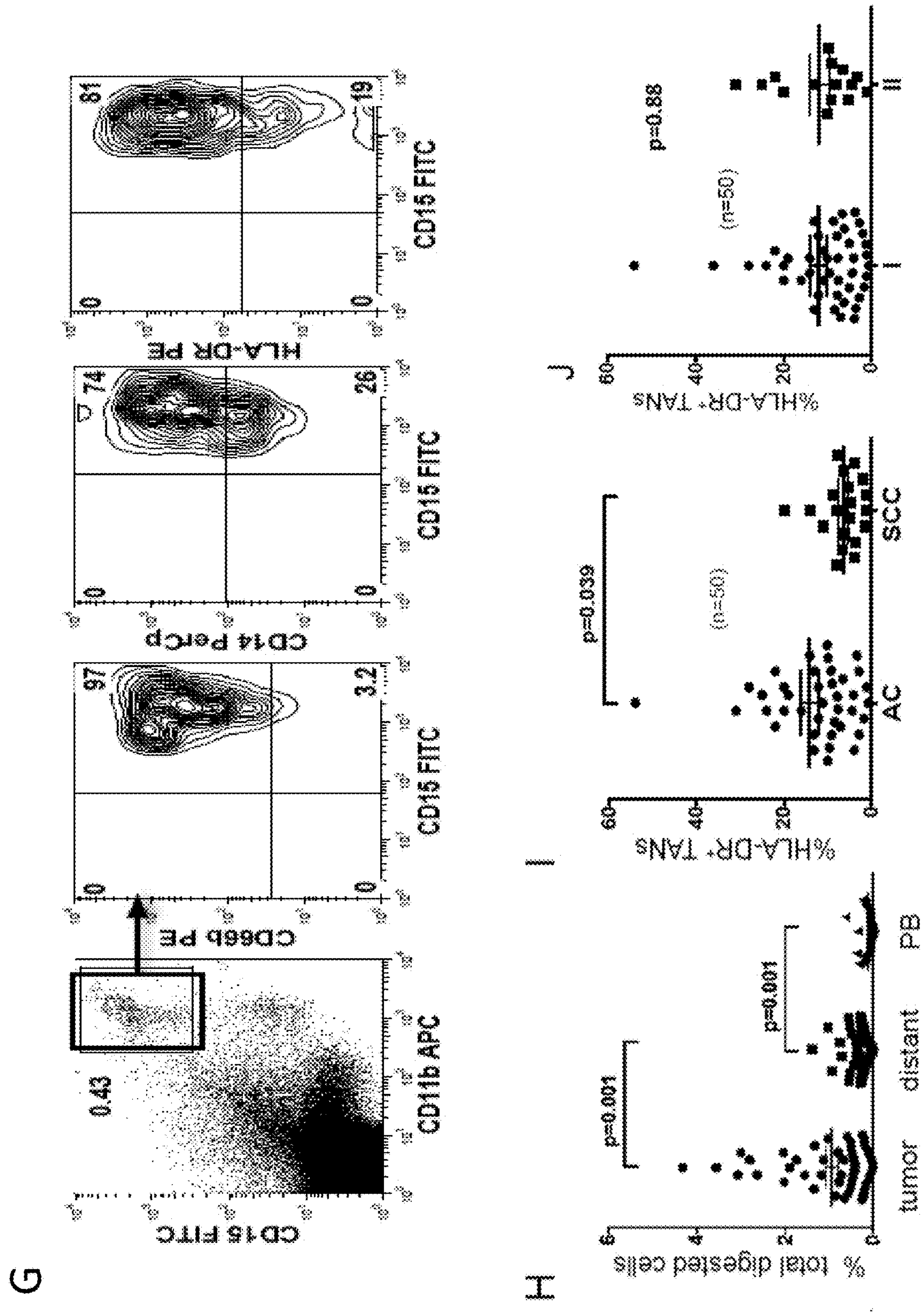
Figures 11K, 11L, 11M, 11N, 11O:
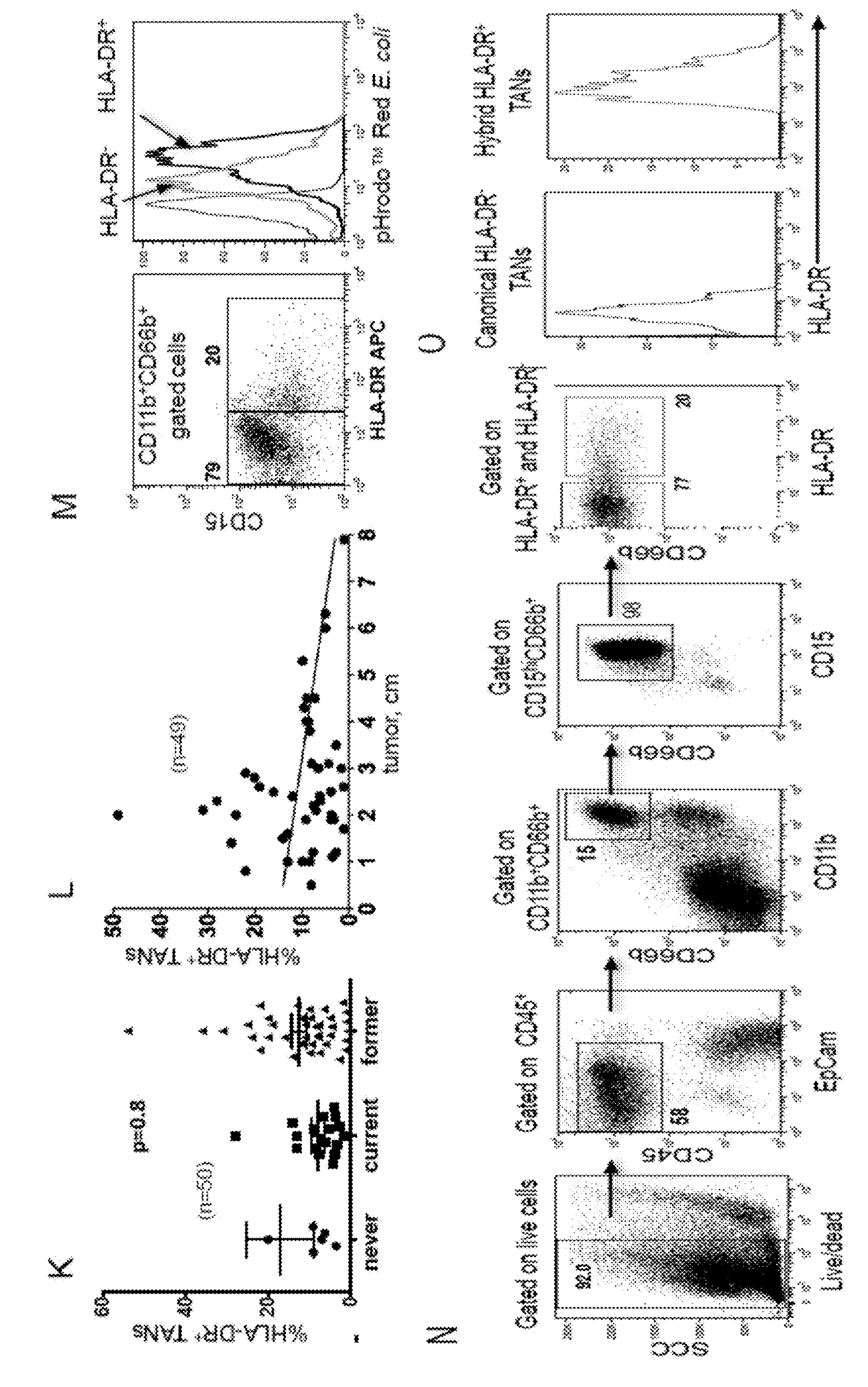

The frequency of this identified subset of TANs varied from 0.5% to 25% among all TANs (FIG. 13D) and from 0.1% to 4.3% among all cells in tumor digests (FIG. 11H). The hybrid population was significantly higher in patients with adenocarcinoma compared with patients with squamous cell carcinoma (FIG. 11I). There were no significant associations between the frequency of APC-like TANs and tumor stage or smoking history (FIG. 11J-11K). Interestingly, a significantly smaller percentage of $HLA\text{-}DR^+$ hybrid neutrophils among TANs in large tumors (diameter>3 cm) versus the small tumors (diameter<3 cm) (FIG. 13D and FIG. 11L) was observed. Thus, the hybrid population appears to decline as tumors enlarge, and is completely absent in tumors greater than 5-7 cm in diameter. Together, these data demonstrate that neutrophils in some early-stage lung tumors undergo unique phenotypic changes, yielding a subset of TANs with composite characteristics of neutrophils and APC.

Example 8: APC-Like Hybrid TANs Stimulate and Support T Cell Responses

The functional activity of APC-like TANs was first evaluated to ensure that these activated cells were not "exhausted" or hypo-functional. TANs were thus isolated from tumors and stimulated with lipopolysaccharide (LPS). After LPS stimulation, $HLA\text{-}DR^+$ hybrid TANs produced much more tumor necrosis factor α (TNF-α) and interleukin-12 (IL-12) when compared with $HLA\text{-}DR^+$ canonical TANs (FIG. 13E). Furthermore, $HLA\text{-}DR^+$ hybrid TANs phagocytosed *Escherichia coli* bioparticles more efficiently than $HLA\text{-}DR^-$ canonical TANs (FIG. 11M). These data demonstrate that APC-like hybrid TANs are fully functional and, in fact, perform major functions such as cytokine production and phagocytosis superior to canonical TANs.

Figure 13F:
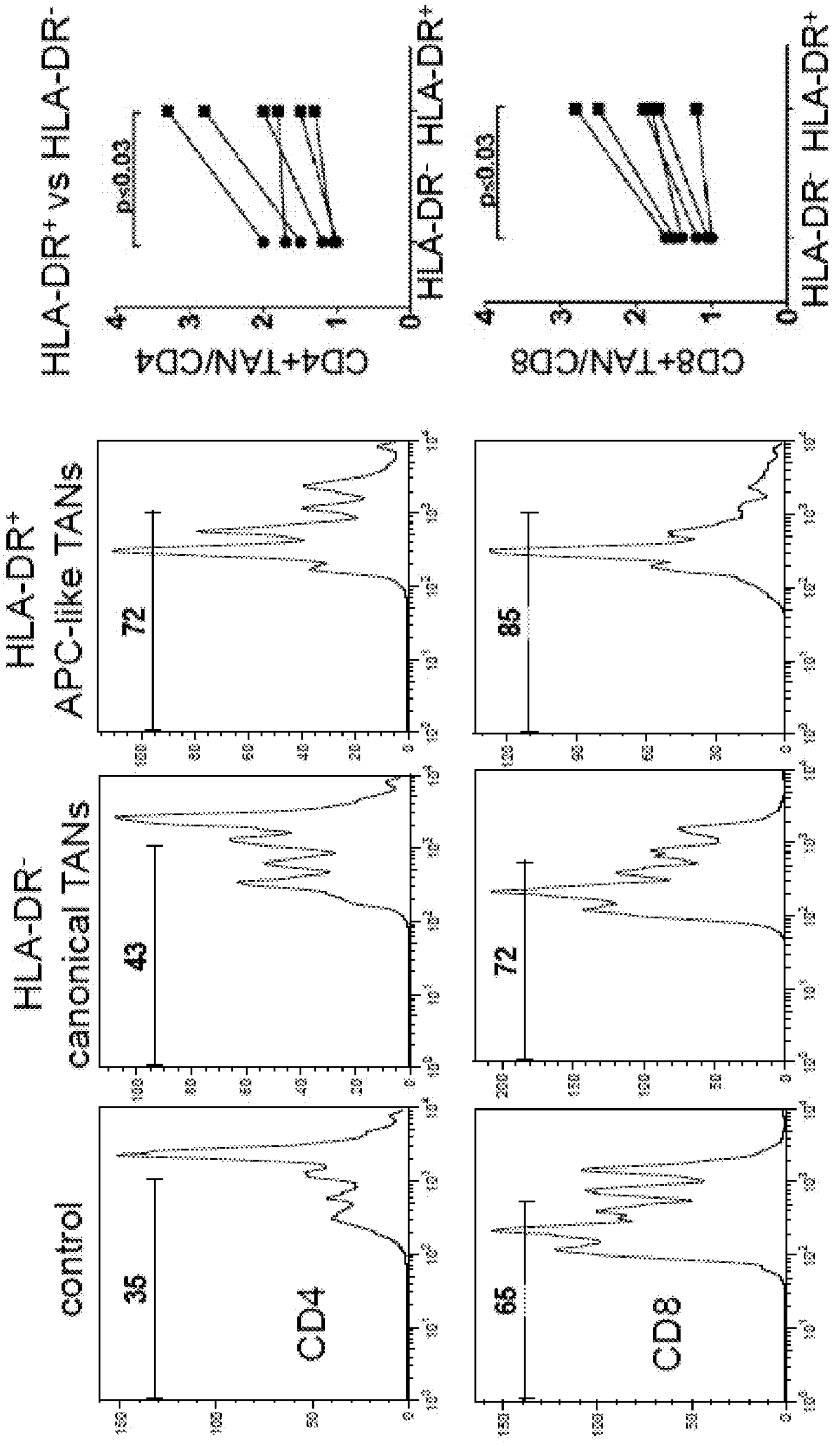

To determine the effect of APC-like hybrid TANs on T cell responses, TAN subsets were isolated by flow cytometry cell sorting (FIG. 11N-11O). Each sorted TAN subset was co-cultured with autologous carboxyfluorescein succinimidyl ester (CFSE)-labeled peripheral blood mononuclear cells (PBMCs) that had been stimulated with plate-bound anti-CD3 antibodies (Abs) (FIG. 13F). The proliferation of CD4 and CD8 cells after 4 days of stimulation was markedly augmented after exposure to $HLA\text{-}DR^+$ hybrid TANs versus the $HLA\text{-}DR^-$ canonical TANs (FIG. 13F).

Figure 13G:
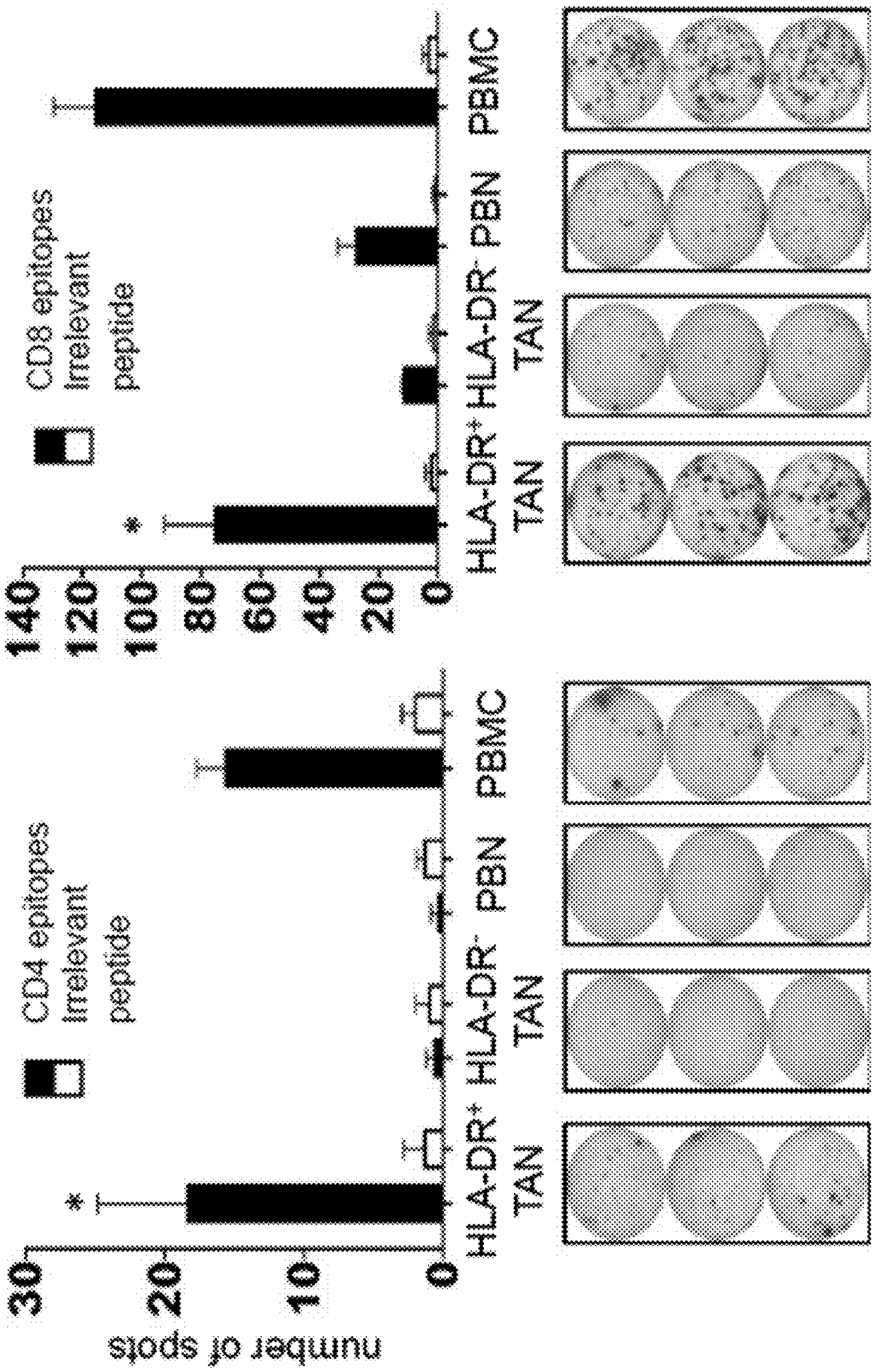

Experiments were performed to determine whether APC-like hybrid TANs could trigger and sustain antigen-specific T cell responses. Autologous T cells were co-cultured with TAN subsets that had been pulsed with mixtures of overlapping peptides from commercially available peptide pools. Each peptide pool corresponded to defined HLA class I or II restricted T cell epitopes from cytomegalovirus, Epstein-Barr virus, influenza virus, or *Clostridium tetani* designed to stimulate T cells with a broad array of HLA types. As shown in FIG. 13G, the HLA-$DR^+$ hybrid TANs efficiently triggered memory CD8 and CD4 T cell responses to HLA class I and II restricted T cell epitopes, respectively. Canonical TANs and PBNs induced only weak CD8 T cell responses and did not trigger CD4 T cell responses. Together, these data demonstrate that HLA-$DR^+$ hybrid TANs are able to function as efficient APCs.

Example 9: Long-Lived Immature Neutrophils Recapitulate the Phenotype of APC-Like Hybrid TANs in the Presence of Tumor-Derived Factors Given the anti-tumor activity of APC-like TANs due to their strong stimulatory effect on T cell responses, the mechanisms by which these cells could originate and expand in the human tumor microenvironment was investigated.

Figure 14A:
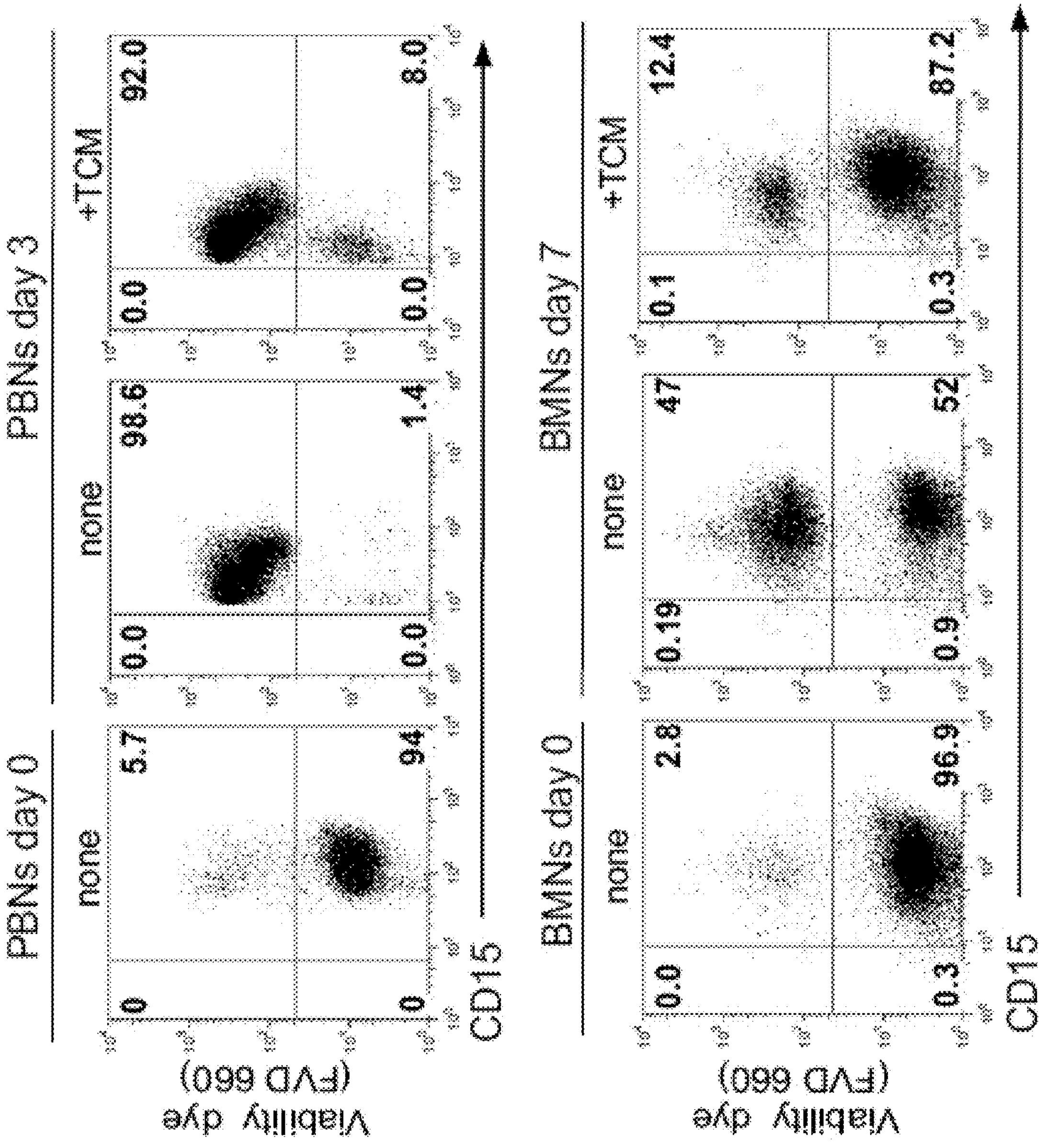
FIGS. 14A-14F are a series of graphs and images showing tumor-derived factors differentiate long-lived immature BMNs into a hybrid subset with a partial phenotype of dendritic cells and macrophages.
Figures 14B, 14C:
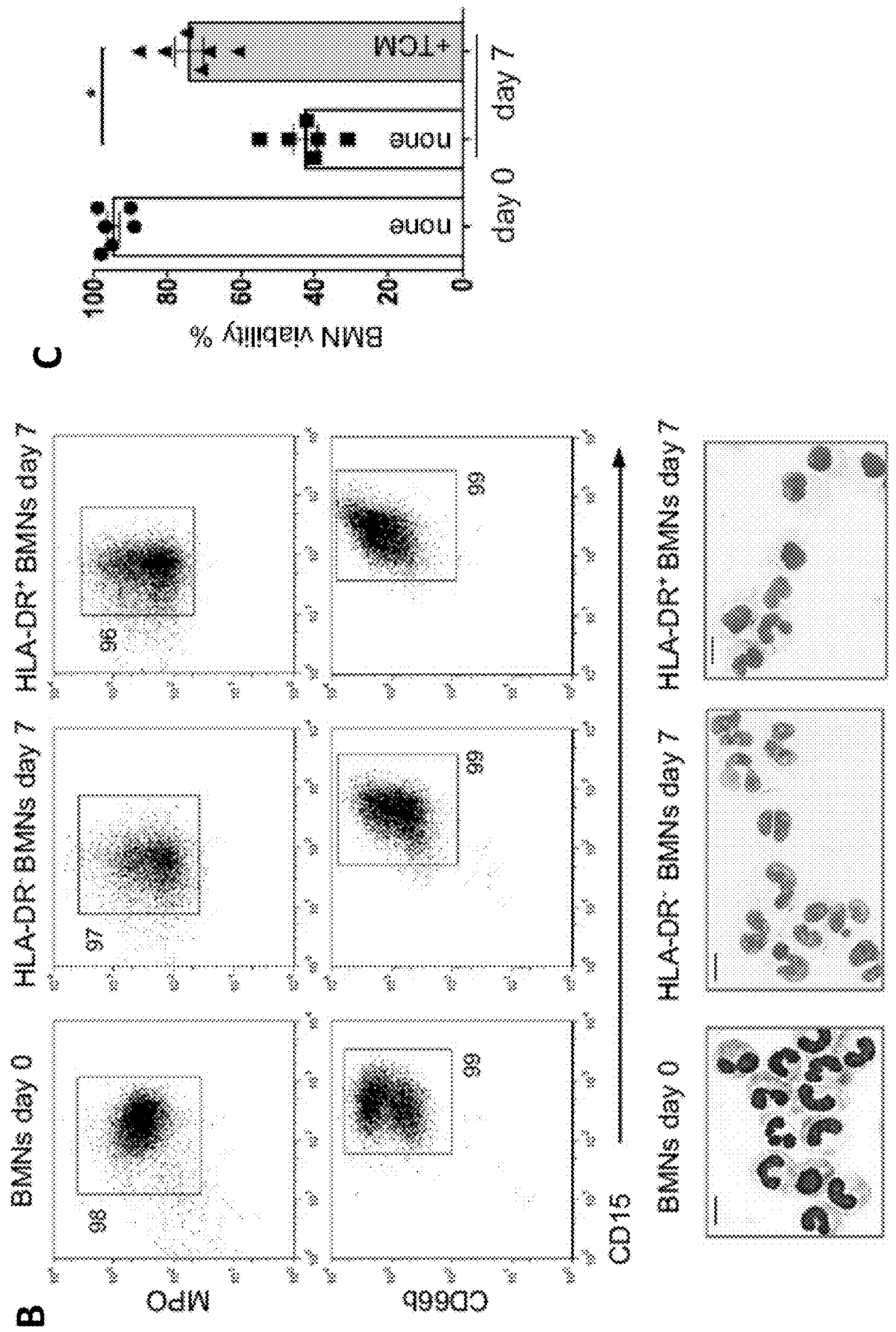
Figure 15A:
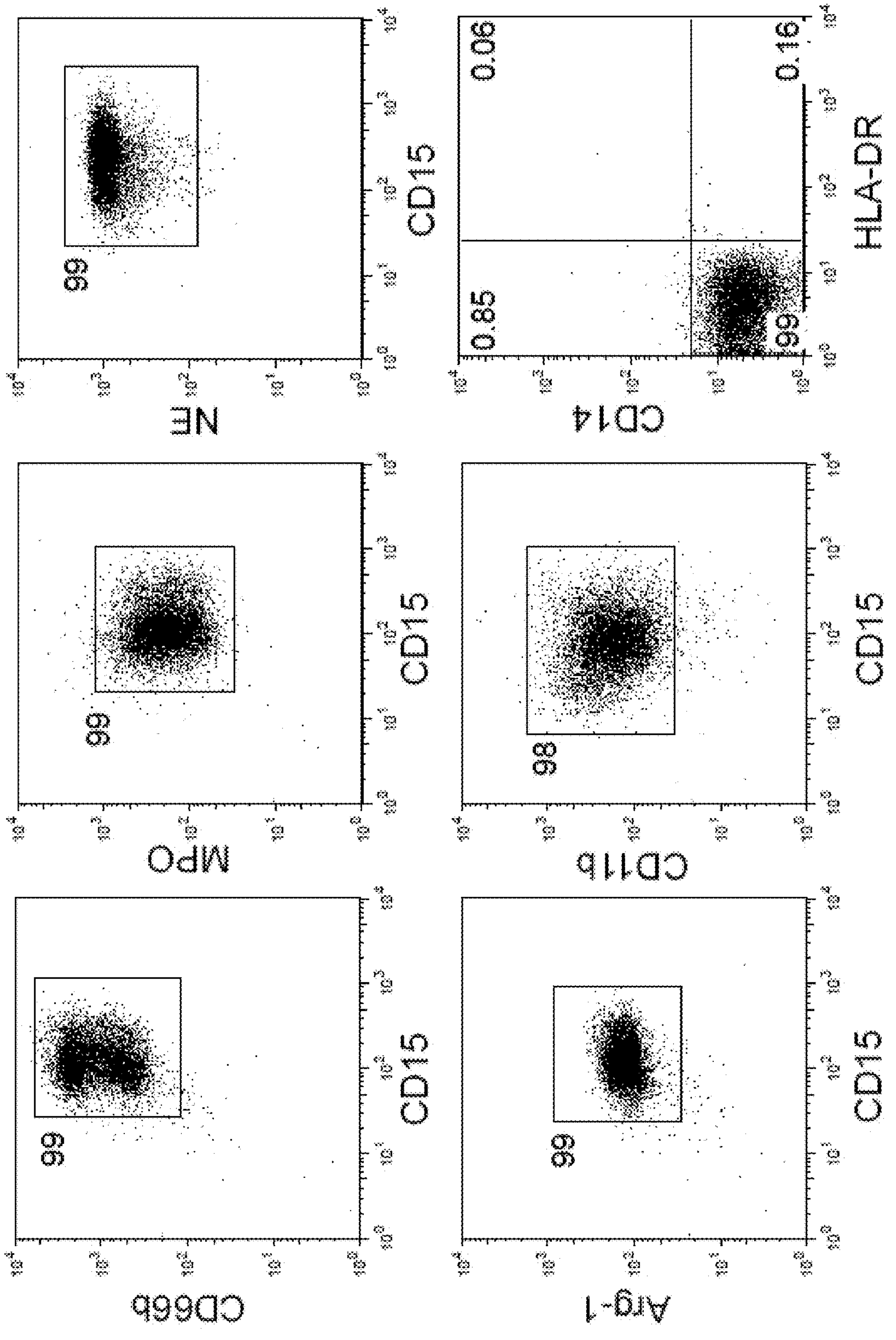
FIGS. 15A-15F are a series of graphs showing tumor-derived factors differentiate long-lived immature BMNs into a hybrid subset with a partial phenotype of dendritic cells and macrophages.
Figures 15B, 15C:
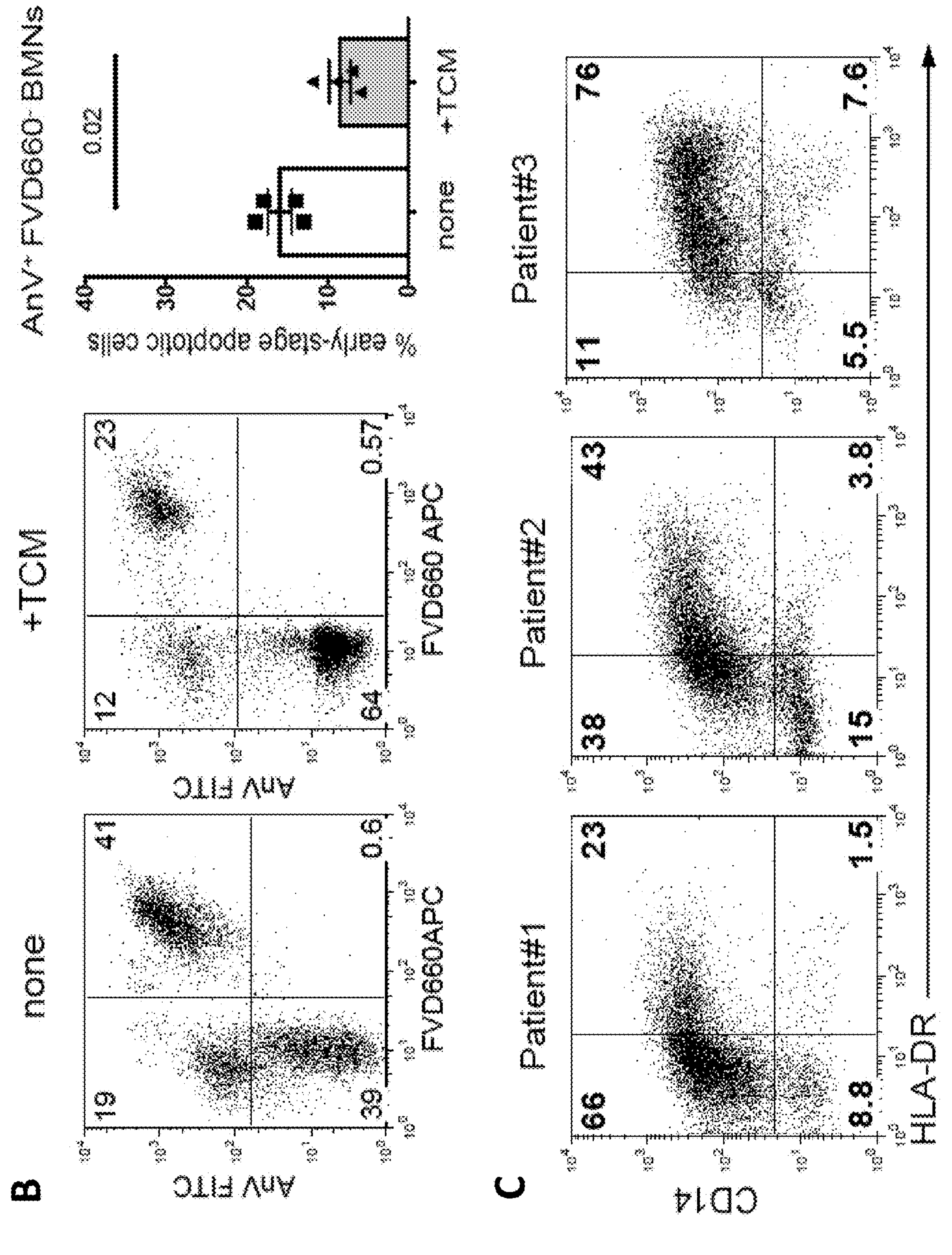

Tumor-conditioned media (TCM) was collected from digested lung cancers that contained >15% of hybrid TANs among all TANs (termed hybrid-inducing TCM). Purified PBNs were exposed to hybrid-inducing TCM and it was discovered that PBNs did not differentiate into the HLA-$DR^+CD14^+$ neutrophils and died within 3 days (FIG. 14A). To determine whether more immature neutrophils with a higher degree of plasticity differentiate into APC-like hybrid neutrophils, a highly enriched population of immature human bone marrow neutrophils (BMNs) was obtained. Isolated BMNs expressed the myeloid/granulocytic specific markers CD11b, CD66b, CD15, Arg-1, NE, and MPO, and were mostly "band"-like immature neutrophils in appearance (FIG. 14B and FIG. 15A). Of note, the purified BMNs did not express HLA-DR and CD14 and were not contaminated with macrophages and monocytes (FIG. 15A). Unlike blood neutrophils, about 40% of these BMNs could survive in cell culture for up to 1 week and their viability was dramatically increased in the presence of TCM (FIGS. 14A, 14C, and 15B). Thus, BMNs with a prolonged lifespan in vitro provided large quantities of cells that could be used to model the origins and differentiation process of neutrophils in the tumor microenvironment.

Figure 14D:
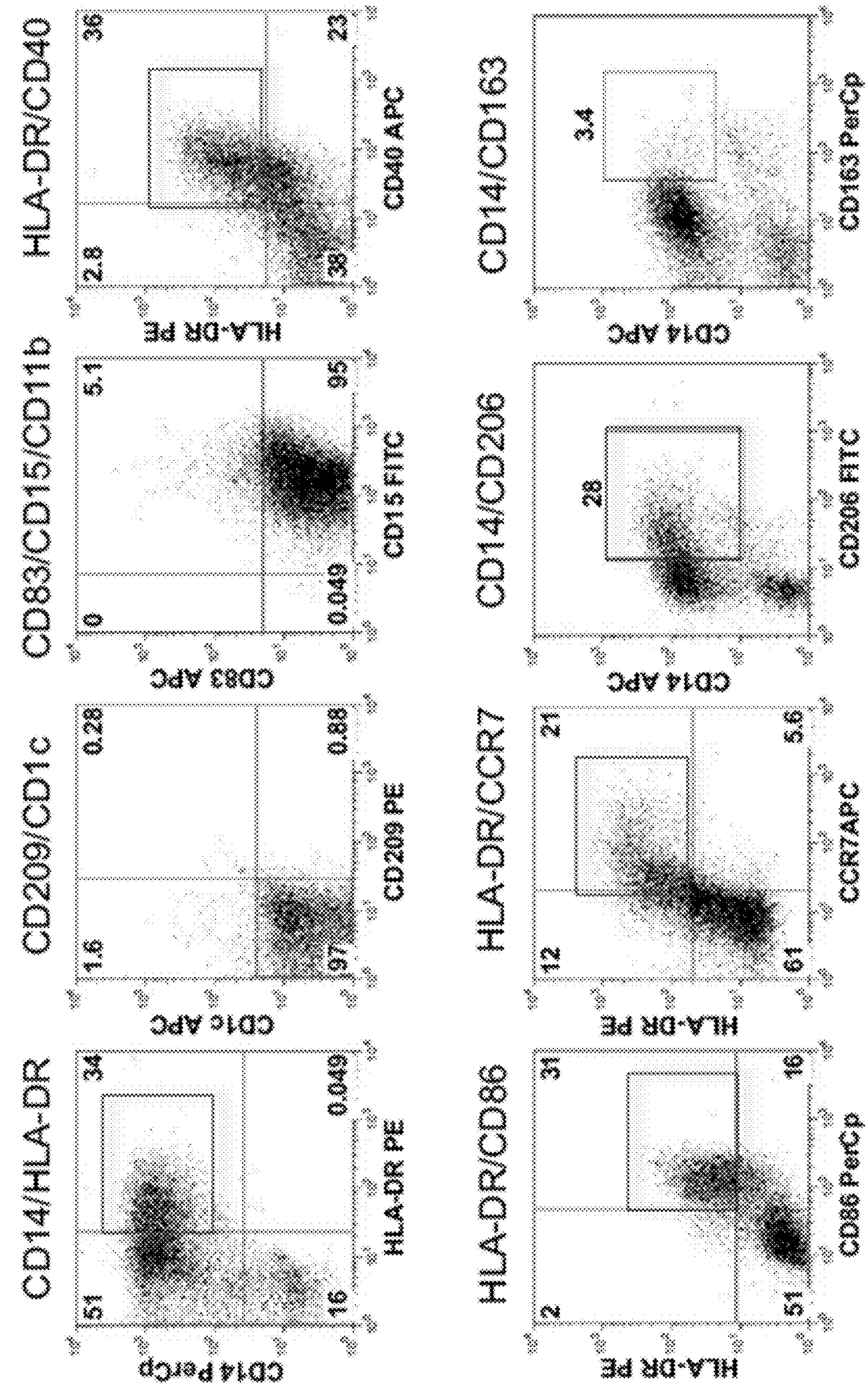
Figures 14E, 14F:
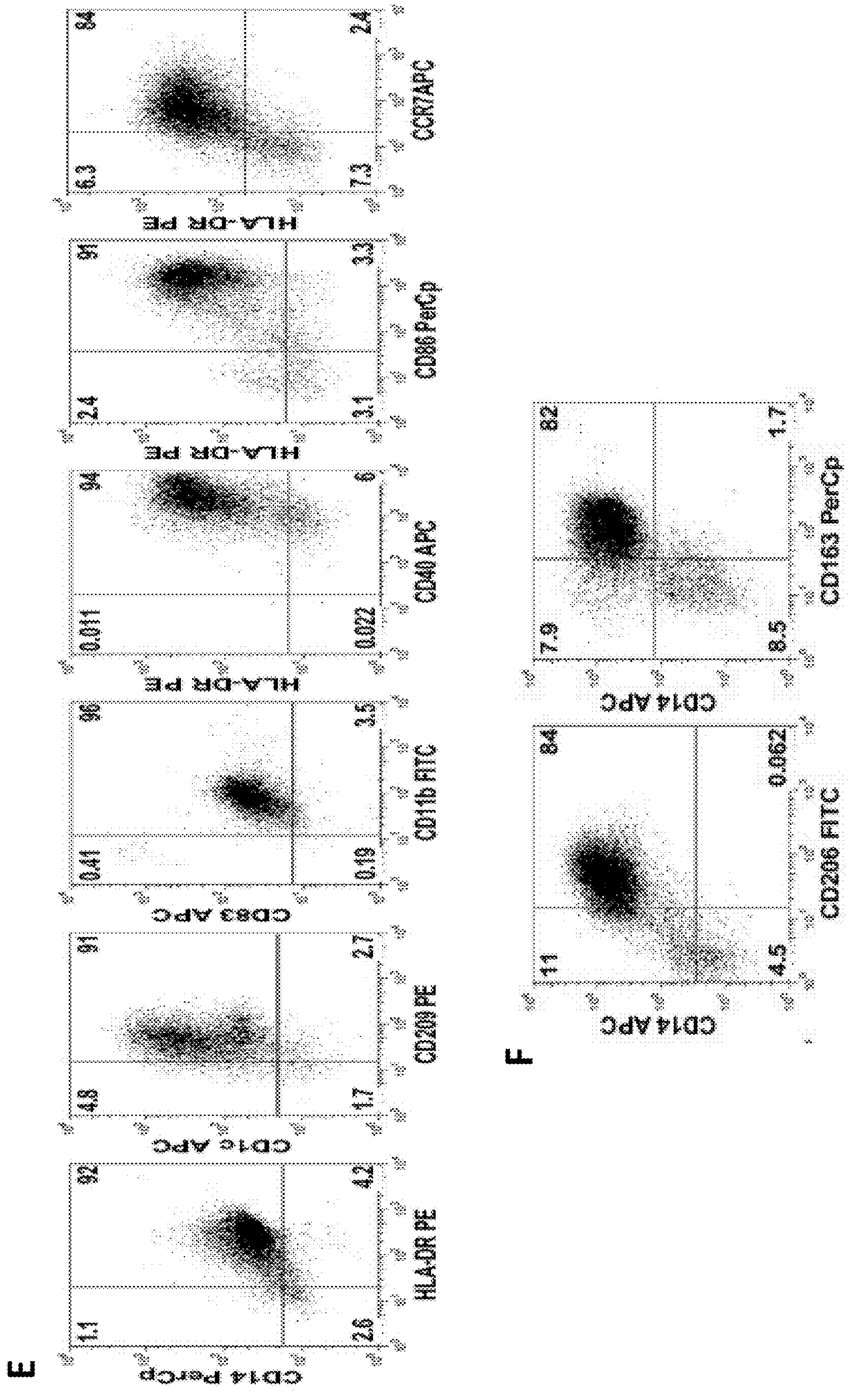
Figures 15D, 15E:
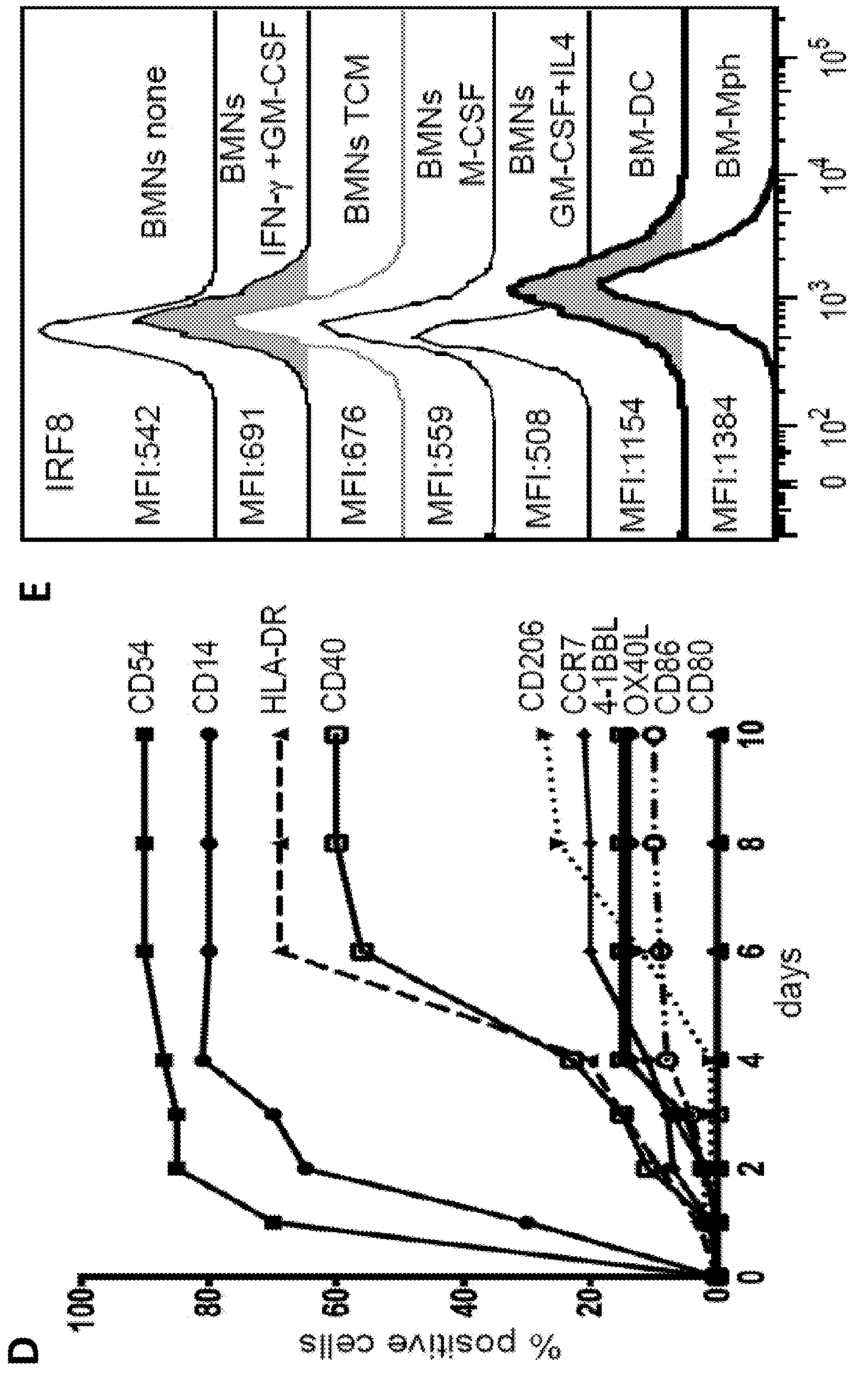

After 7 days of incubation of BMNs with hybrid-inducing TCMs, the formation of a cell subset that retained all its granulocytic markers (FIG. 14B and FIG. 4) and acquired the same phenotype as the tumor-derived hybrid TANs (HLA-$DR^+CD14^+CD86^+CD206^+CCR7^+$) was observed (FIG. 14D). Similar to hybrid TANs, most of the BMNs also changed their nuclear shape from band-like to oval when they converted into hybrid BMNs (FIG. 14B). A detailed phenotypic comparison of PBNs, BMNs, and bone marrow (BM)- and tumor-derived hybrid neutrophils is summarized in FIG. 4. The differentiation of BMNs into HLA-$DR^+$ $CD14^+$ APC-like hybrid BMNs after exposure to hybrid-inducing TCM was donor dependent and varied from 20% to 80% of the initial BMN population (FIG. 15C). BMNs began to upregulate CD14 within 24 hr of co-culturing with hybrid-inducing TCM, while the expression of HLA-DR, CD86, CCR7, and CD206 markers did not appear until day 4 (FIG. 15D). This suggests that these late APC markers are synthesized de novo.

Similar to hybrid TANs, differentiated hybrid BMNs acquired only the partial phenotype of dendritic cells (DC) and macro-phages (Mph) (HLA-$DR^+CD14^+CD86^+$ $CD206^+$) (FIGS. 2E-2G). The hybrid subset of BMNs and TANs differed from BM-derived DC and Mph by absence of CD1c, CD83, CD163, and CD209 markers, and low expression of CD40, CD86, CD115, and CCR7 (FIGS. 14D-14G). The level of the transcription factor IRF8, which regulates monocyte/DC lineage commitment (Yanez et al., 2015. *Blood* 9, 1452-1459), was not dramatically changed in hybrid BMNs and was much lower than the amount detected in BM-derived Mph and DC (FIG. 15E).

Figure 15F:
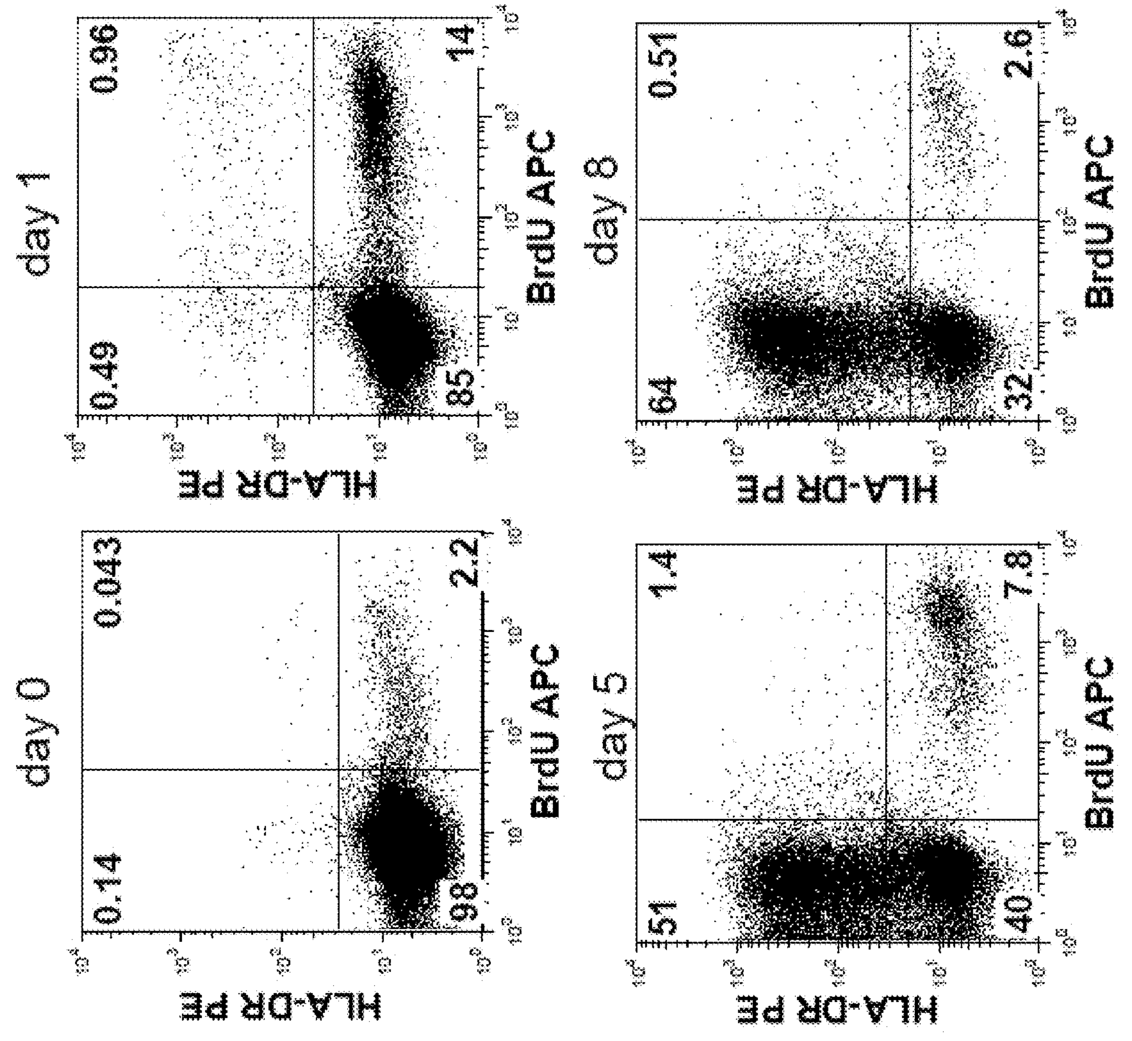

The ability of differentiated APC-like hybrid BMNs to proliferate in the presence of hybrid-inducing TCM and thus represent a self-maintained population of neutrophils was tested. A bromodeoxyuridine (BrdU) incorporation assay revealed that within 24 hr of treatment with hybrid-inducing TCM, 10%-15% of BMNs begin to synthesize DNA in vitro (FIG. 15F). As the differentiation process progressed, a small proportion of HLA-$DR^-$ BMNs continued to incorporate BrdU up to day 8, whereas the differentiated HLA-$DR^+$ neutrophils lost proliferative potential (FIG. 15F).

Figures 16A, 16B:
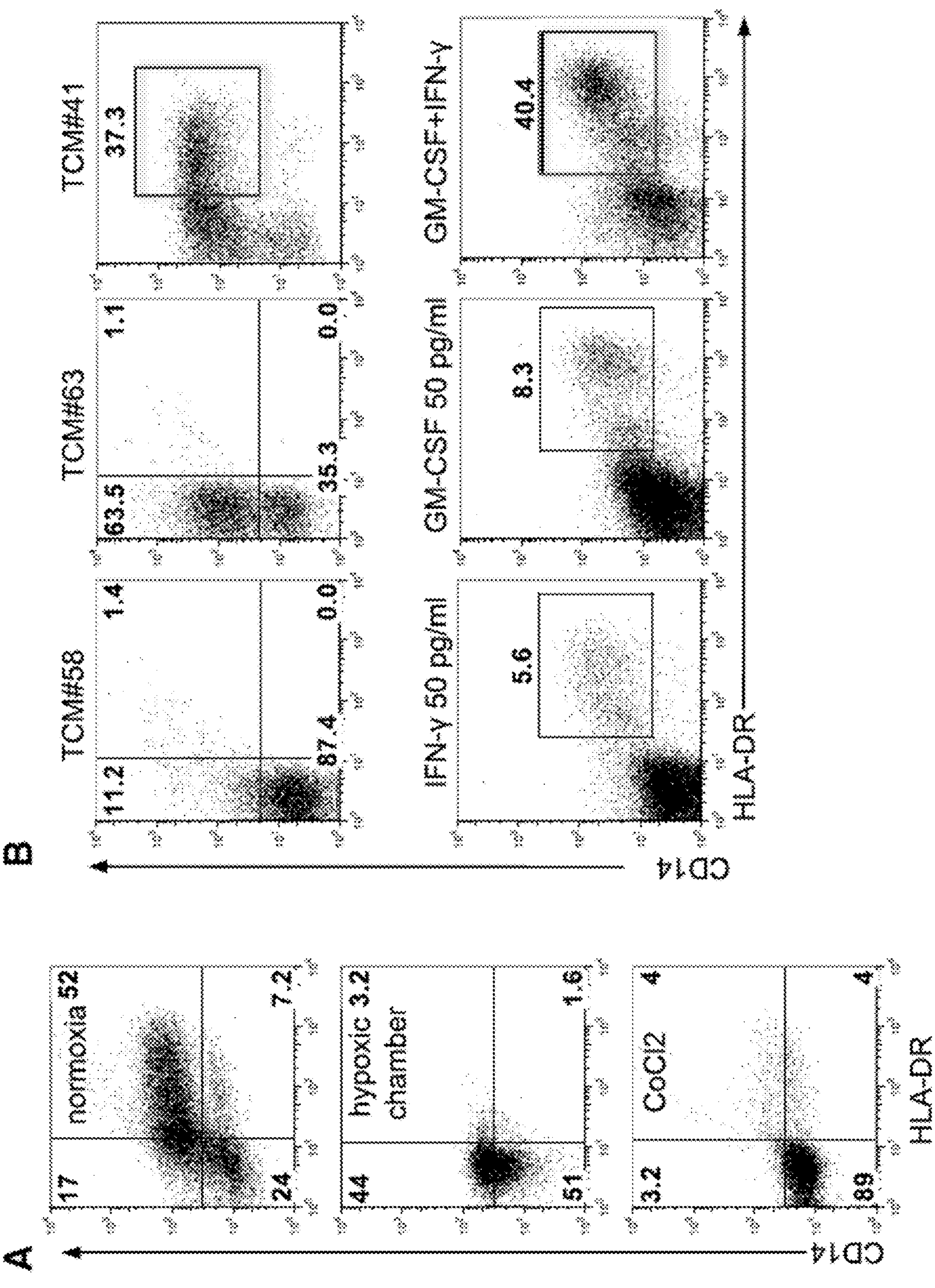
FIGS. 16A-16F are a series of graphs showing tumor-derived IFN-γ and GM-SCF synergistically differentiate immature neutrophils into a subset of APC-like hybrid neutrophils.

Given that the frequency of hybrid TANs was reduced in large tumors (FIG. 13D), it was hypothesized that hypoxia, which is strongly associated with the tumor progression, may negatively regulate the formation of hybrid neutrophils. Thus, BMNs were cultured in the presence of hybrid-inducing TCM for 6 days under normoxic (5% $CO_2$ and 21% $O_2$) and hypoxic (5% $CO_2$ and 5% $O_2$) cell culture conditions. BMNs were also cultured in the presence of hybrid-inducing TCM and cobalt chloride, an agent that induces hypoxia-inducible factor 1 α (HIF-1α), the main transcriptional factor activated in hypoxic conditions. The development of hybrid $CD14^+$HLA– $DR^+$ neutrophils was profoundly inhibited under these hypoxic and hypoxia-simulating conditions (FIG. 16A).

Figure 16C:
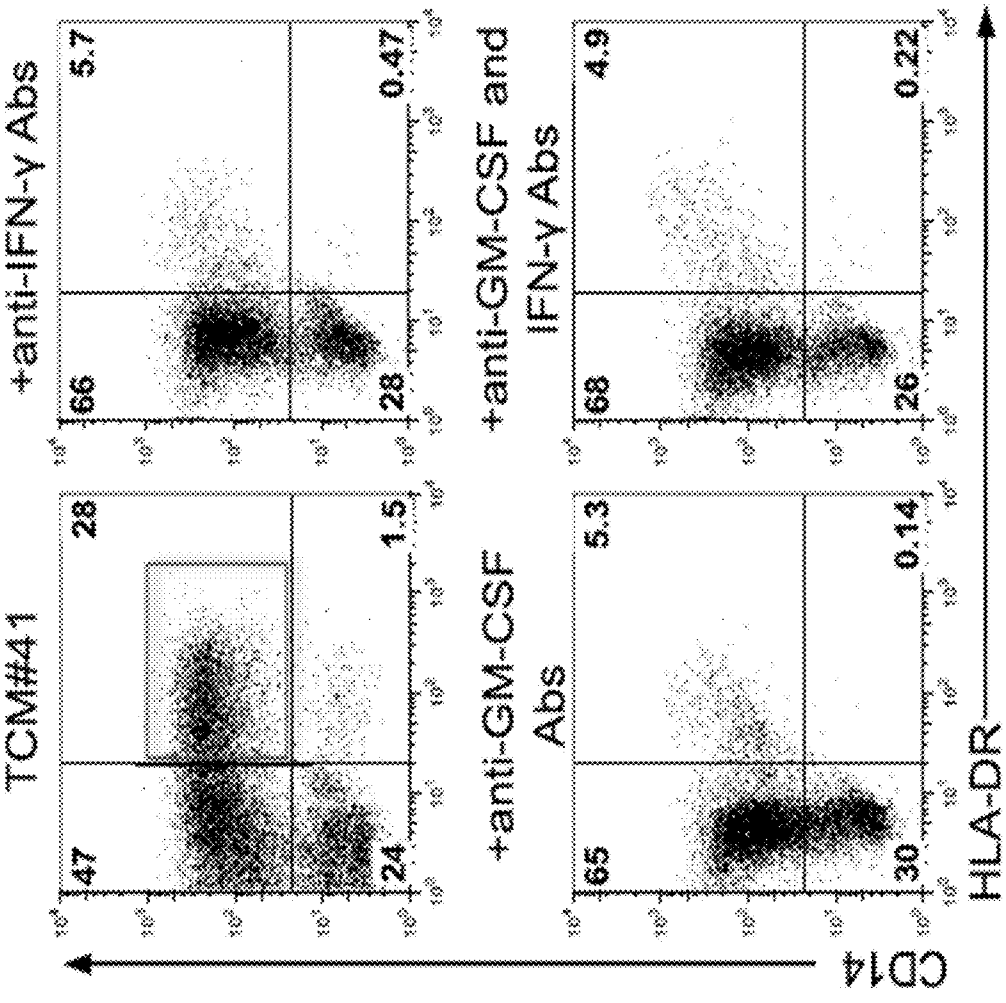
Figure 16D:
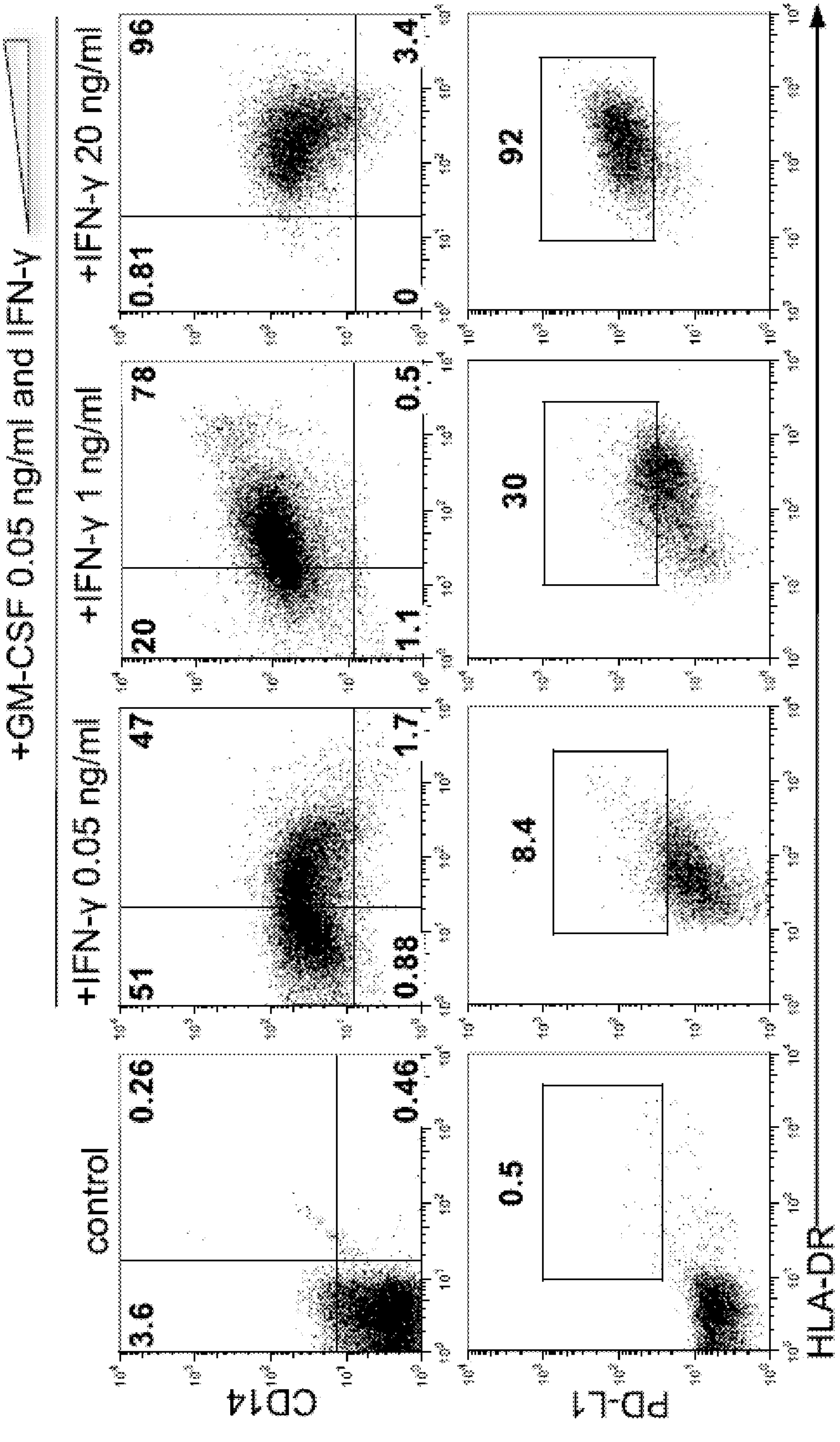
Figure 17A:
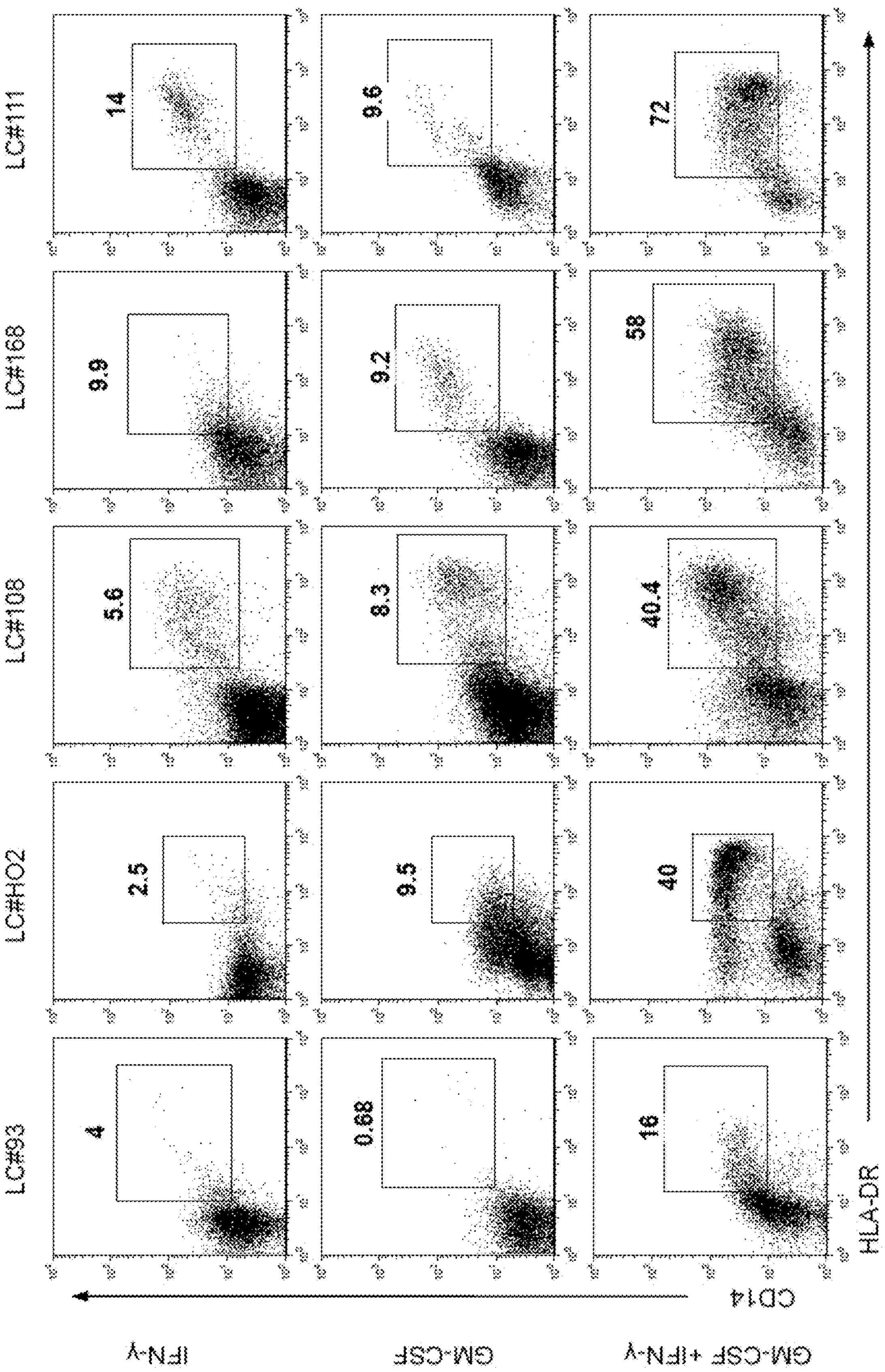
FIGS. 17A-17B are a series of graphs and images showing tumor-derived IFN-γ and GM-SCF synergistically differentiate immature neutrophils into a subset of APC-like hybrid neutrophils.

Example 10: IFN-γ and GM-CSF are Requisite Factors in the Tumor Microenvironment for the Development of Hybrid Neutrophils To determine the particular tumor-specific factors that promote the formation of hybrid TANs, primary TCMs collected from 20 consecutive lung cancer patients were screened and categorized based on their ability to induce: (1) the full phenotype of hybrid cells ($CD14^+$HLA–$DR^+$ $CD11b^+CD66b^+CD15^{hi}$) (FIG. 16B, example TCM #41); (2) the partial phenotype of hybrid cells ($CD14^+$HLA-$DR^-$ $CD11b^+CD66b^+CD15^{hi}$) (FIG. 16B, example TCM #63); or (3) no phenotypic changes (FIG. 16B, example TCM #58). Each TCM was evaluated using a multiplex cytokine/chemokine bead assay. Those TCMs that induced $CD14^+$ HLA-$DR^+$ hybrid cells had increased amounts of granulocyte-colony stimulating factor (G-CSF), IL-6, IL-15, granulocyte-macrophage colony-stimulating factor (GM-CSF), interferon-γ (IFN-γ), macrophage inflammatory protein-1α (MIP-1α), TNF-α, monocyte chemoattractant protein-1 (MCP-1), and monokine induced by IFN-γ (MIG) compared with TCMs that did not induce hybrid cells. The ability of each of these factors (at the low concentrations found in the TCMs) to induce the $CD14^+$HLA-$DR^+$ hybrid phenotype in BMNs was tested and only IFN-γ and GM-CSF were able to induce the phenotype, although in a relatively low percentage of cells (FIG. 16B and FIG. 17A). However, these factors worked in a synergistic manner: when combined at very low concentrations of 50 pg/ml of each factor, they induced expression of APC markers in a large proportion (>40%) of the cells in a donor-dependent fashion (FIG. 3F and FIG. 17A). The addition of neutralizing monoclonal antibodies for either IFN-γ or GM-CSF completely inhibited the formation of BM hybrid cells in the presence of hybrid-inducing TCM (FIG. 16C), thereby confirming that both IFN-γ and GM-CSF play a key role in the induction process. Interestingly, incubation of BMNs with a low dose of GM-CSF (50 pg/ml) and increasing concentrations of IFN-γ (from 50 pg/ml to 20 ng/ml) resulted in the expansion of $CD14^+HLA\text{-}DR^+$ BMNs from 40% to 96% among all BMNs (FIG. 16D, upper panel). However, the treatment of BMNs with IFN-γ at a concentration of more than 1 ng/ml gradually induced the expression of PD-L1 on the $HLA\text{-}DR^+$ BMNs (FIG. 16D, lower panel), resulting in the formation of hybrid neutrophils with T cell suppressive activity (described in detail herein).

Figures 16E, 16F:
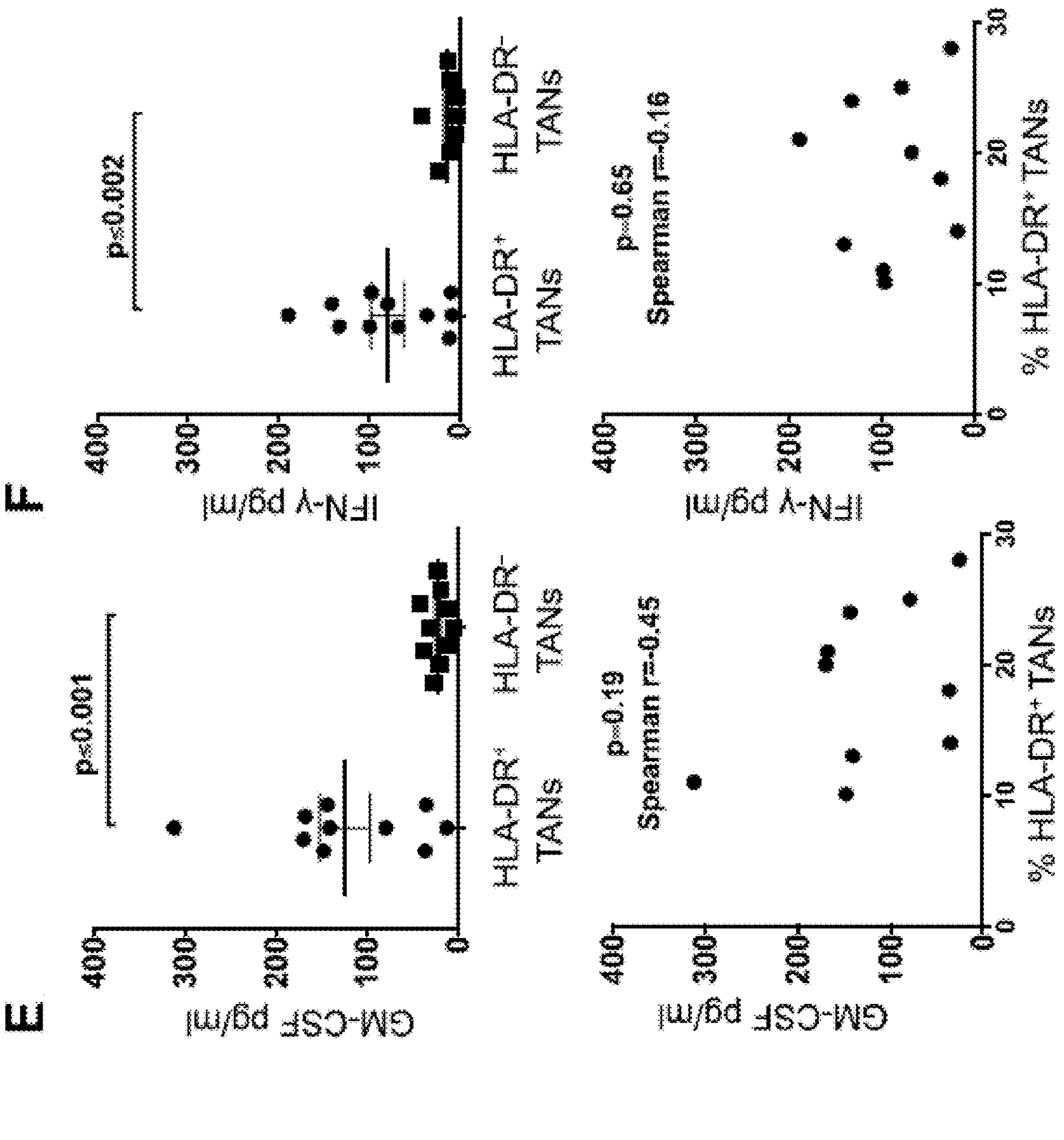
Figure 17B:
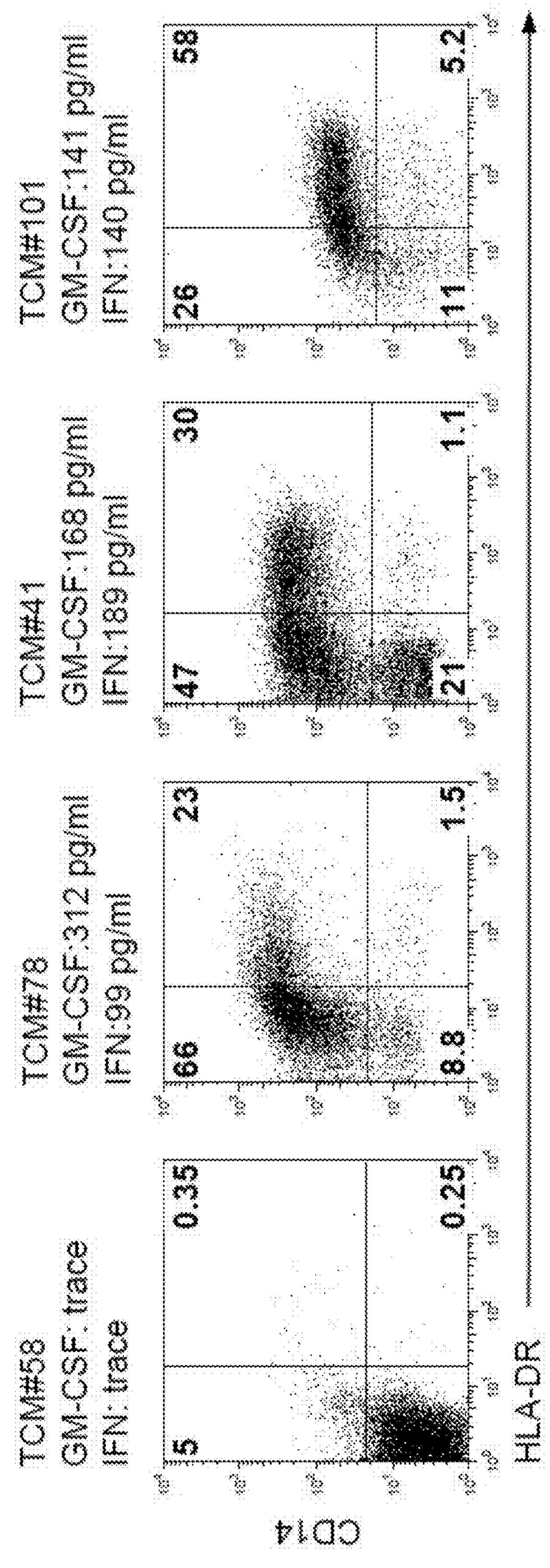

The frequency of APC-like TANs in the tumor digests was analyzed, and, in parallel, the concentration of IFN-γ and GM-CSF in the supernatants collected from digested autologous tumor cell cultures was measured. FIGS. 16E-16F demonstrate that the levels of IFN-γ and GM-CSF were statistically higher in tumors where there was a high proportion of hybrid TANs (>10% of all TANs). However, the generation of hybrid neutrophils in vivo is most likely more complex and not solely due to IFN-γ and GM-CSF levels, because the absolute levels of IFN-γ and GM-CSF in the TCM did not necessarily correlate with the frequency of hybrid neutrophils (>10% of all TANs) in each tumor as shown in FIGS. 16E-16F. Also, when BMNs from the same donor were exposed to different hybrid-inducing TCMs containing variable concentrations of IFN-γ and GM-CSF, a clear relationship between absolute levels of GM-CSF and IFN-γ and the degree of hybrid neutrophil formation was not observed (FIG. 17B). These data suggest that there is a requisite threshold level of GM-CSF and IFN-γ, and additional tumor-derived factors may contribute to the process of hybrid neutrophil differentiation.

Example 11: $CD11b^+CD15^{hi}CD10^-CD16^{int/low}$ Progenitors Give Rise to APC-Like Hybrid Neutrophils The low frequency of APC-like hybrid TANs along with high heterogeneity in their accumulation in cancer patients suggested that there might be precursor cells that could differentiate into this unique subset of neutrophils under specific favorable conditions in some tumors. Therefore, whether the ability of long-lived immature BMNs to develop hybrid neutrophils is either shared by all immature subsets or limited to a specific differentiation stage was investigated.

Figures 18A, 18B, 18C, 18D:
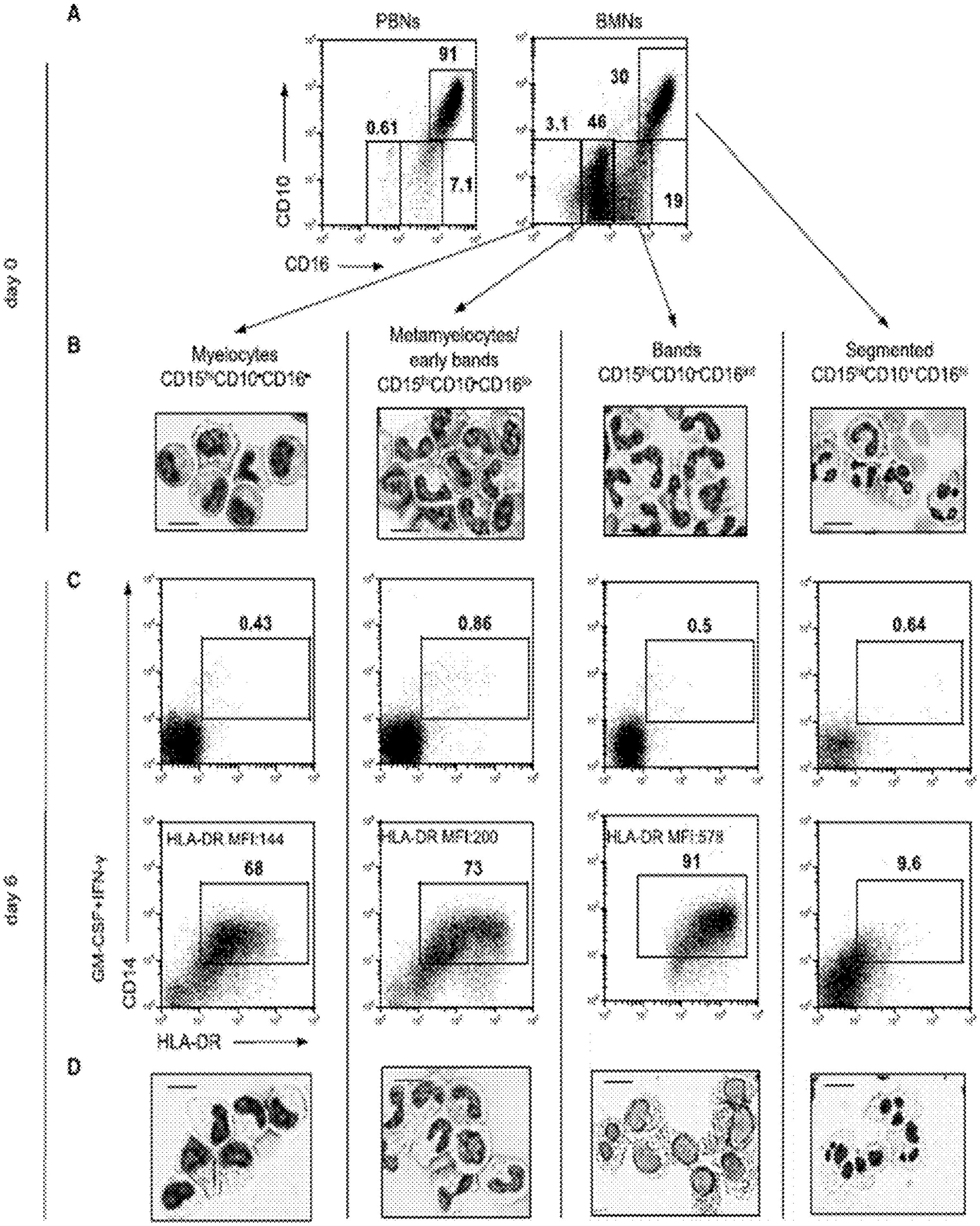
FIGS. 18A-18D are a series of graphs and images showing APC-like hybrid neutrophils originate from $CD11b^+$ $CD15^{hi}$ $CD66b^+CD10-CD16^{lo/int}$ progenitors.
Figures 19A, 19B, 19C:
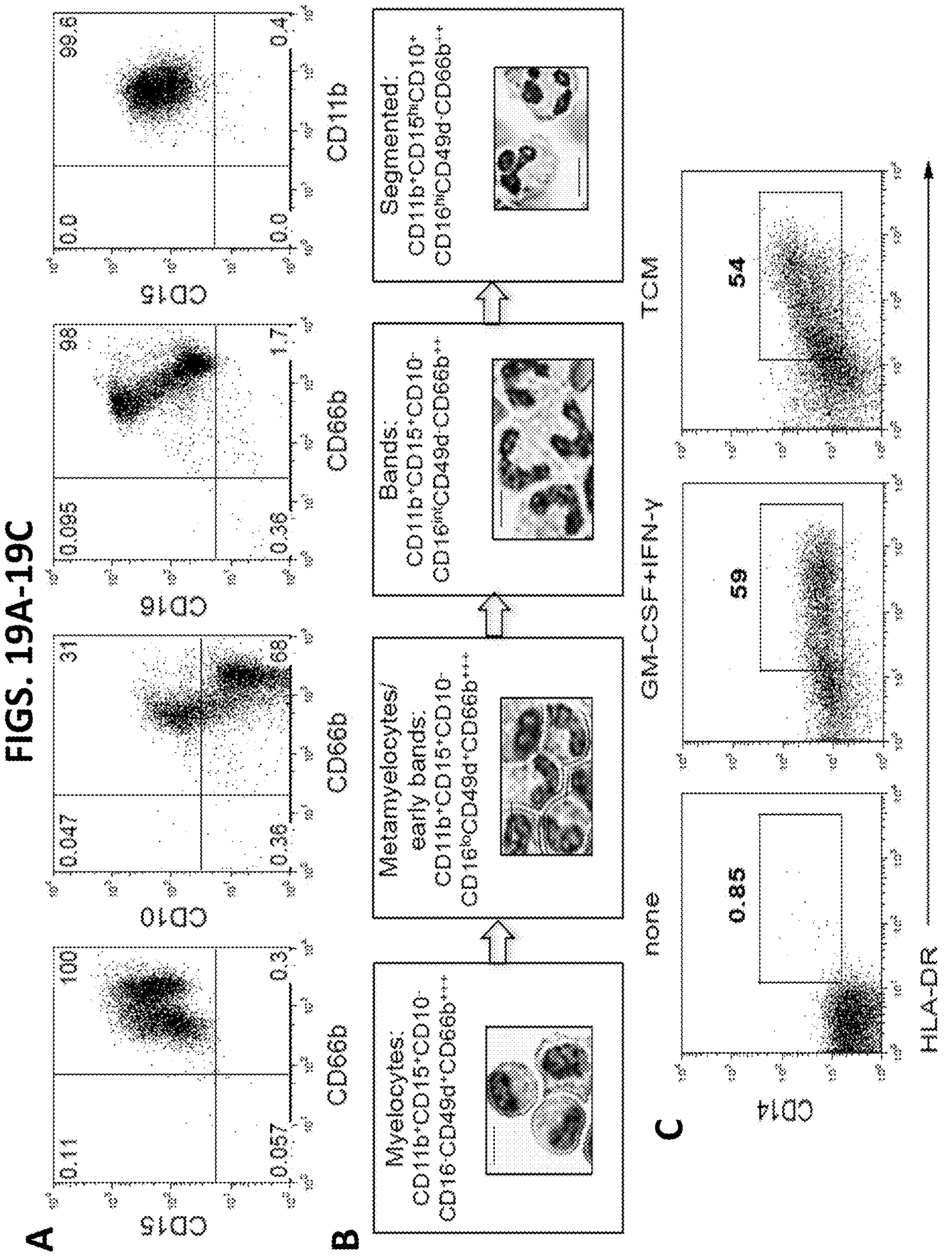
FIGS. 19A-19C are a series of graphs and images showing APC-like hybrid neutrophils originate from $CD11b^+$ $CD15^{hi}CD66b^+CD10-CD16^{lo/int}$ progenitors.

The combined expression of CD11b, CD15, CD10, CD49d, and CD16 was used to distinguish the different maturational states of BMNs (Elghetany, 2002. *Blood Cells Mol. Dis.* 2, 260-274). $CD11b^+CD15^{hi}$ BMNs consisted of a heterogeneous combination of mature $CD16^{hi}CD10^+$ $CD49d^-$ cells, immature $CD16^{int}CD10^-CD49d^-$ band cells, and $CD16^{low/-}CD10^-$ $CD49d^+$ metamyelocytes/myelocytes (FIG. 18A). Of note, all mature and immature BMNs express CD66b but at slightly different levels (FIG. 19A). The detailed phenotype of neutrophils at different maturation stages is summarized in FIG. 19B. BMNs were isolated at different stages of maturation by flow cytometry sorting based on these phenotypes. Cytomorphology confirmed that each population was associated with distinct maturation stages (FIG. 18B). These sorted subsets of BMNs were cultured in the presence of low concentration of IFN-γ (50 pg/ml) and GM-CSF (50 pg/ml) for 6 days, after which the resulting $CD11b^+CD15^{hi}CD66b^+$ neutrophil populations were analyzed for surface expression of CD14 and HLA-DR (FIG. 18C). Data revealed that $CD14^+HLA\text{-}DR^+$ hybrid neutrophils could be generated from all immature stages of neutrophils except the terminally differentiated, mature, segmented neutrophils. However, the level of HLA-DR expression on these hybrid neutrophils was affected by the degree of immaturity of the neutrophils prior to exposure to IFN-γ and GM-CSF: the more mature $CD15^{hi}CD10''$ $CD16^{int}$ band cells gave rise to hybrid neutrophils, with the highest expression of HLA-DR on the surface when compared with hybrid neutrophils differentiated from $CD15^{hi}CD10^-CD16^{-/lo}$ myelocytes and metamyelocytes/early bands (FIG. 18C). Interestingly, the majority of the neutrophils differentiated from $CD15^{hi}CD10^-CD16^{int}$ band cells were able to change their nuclear contour from band-like to oval when compared with neutrophils differentiated from myelocytes and metamyelocytes/early bands (FIG. 18D).

Importantly, the circulating blood $CD16^{int/lo}CD10^-$ immature neutrophils that could potentially traffic into tumors were also able to differentiate into hybrid neutrophils in the presence of hybrid-inducing TCM or IFN-γ and GM-CSF (FIG. 19C).

Example 12: Ikaros Negatively Regulates the Development of APC-Like Hybrid Neutrophils Murine models have shown that the transcription factor Ikaros is involved in the control of neutrophil differentiation by silencing specific pathways in common precursors that allow for macrophage-monocyte development. Given that hybrid neutrophils exhibit some characteristics of monocytic lineage cells, but can be differentiated from granulocyte-committed precursors, it was hypothesized that the hybrid-inducing ability of TCM may be due to two possible synergistic effects on granulocyte progenitor cells: (1) premature downregulation of Ikaros, thus allowing some degree of monocyte differentiation to occur; and (2) the provision of the appropriate macrophage stimulating factors (i.e., GM-CSF) to activate the monocyte differentiation pathways.

Figure 20A:
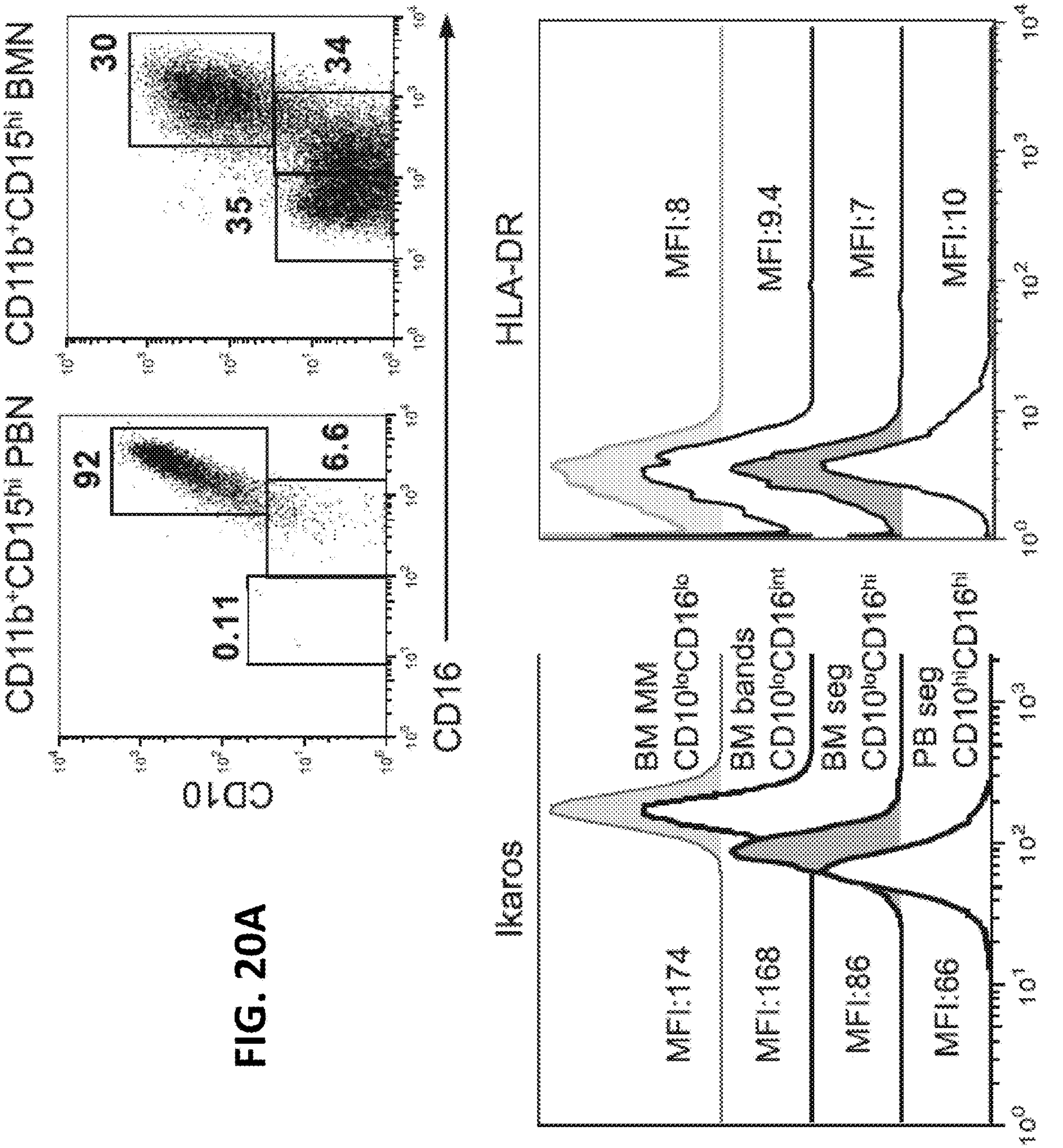
FIGS. 20A-20D are a series of graphs showing the transcription factor Ikaros negatively regulates the differentiation of hybrid neutrophils.
Figures 20B, 20C:
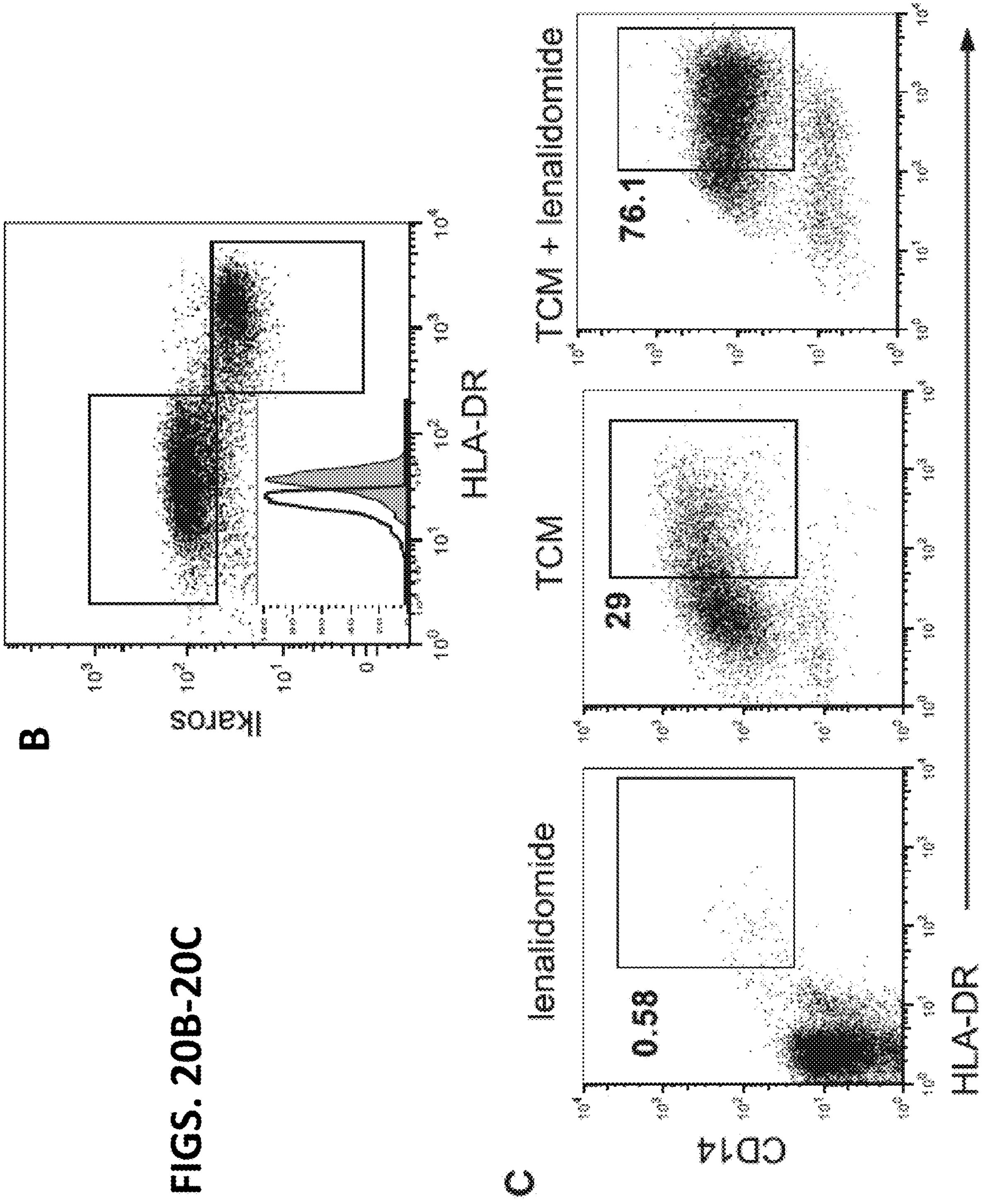

The level of Ikaros expression were measured in BMNs at different stages of maturation and Ikaros was upregulated in all immature neutrophils (bands and metamyelocytes), with lower levels in mature BMNs and PBNs (FIG. 20A). The analysis of BMNs treated with hybrid-inducing TCM revealed that the Ikaros level was lower in $HLA\text{-}DR^+$ hybrid BMNs compared with $HLA\text{-}DR^-$ canonical BMNs (FIG. 20B). Thus hybrid-inducing TCM induced premature downregulation of Ikaros in $HLA\text{-}DR^+$ hybrid BMNs. BMNs were cultured with hybrid-inducing TCM in the presence or absence of the drug lenalidomide, which causes proteasomal degradation of the human Ikaros proteins (Kronke et al., 2014. *Oncoimmunology.* 7, e941742). The addition of lenalidomide to TCM-treated BM neutrophils dramatically facilitated the development of $HLA\text{-}DR^+CD14^+$ hybrid neutrophils (FIG. 20C). Together, these data suggest that Ikaros negatively regulates this process in the presence of tumor-derived factors.

Figure 20D:
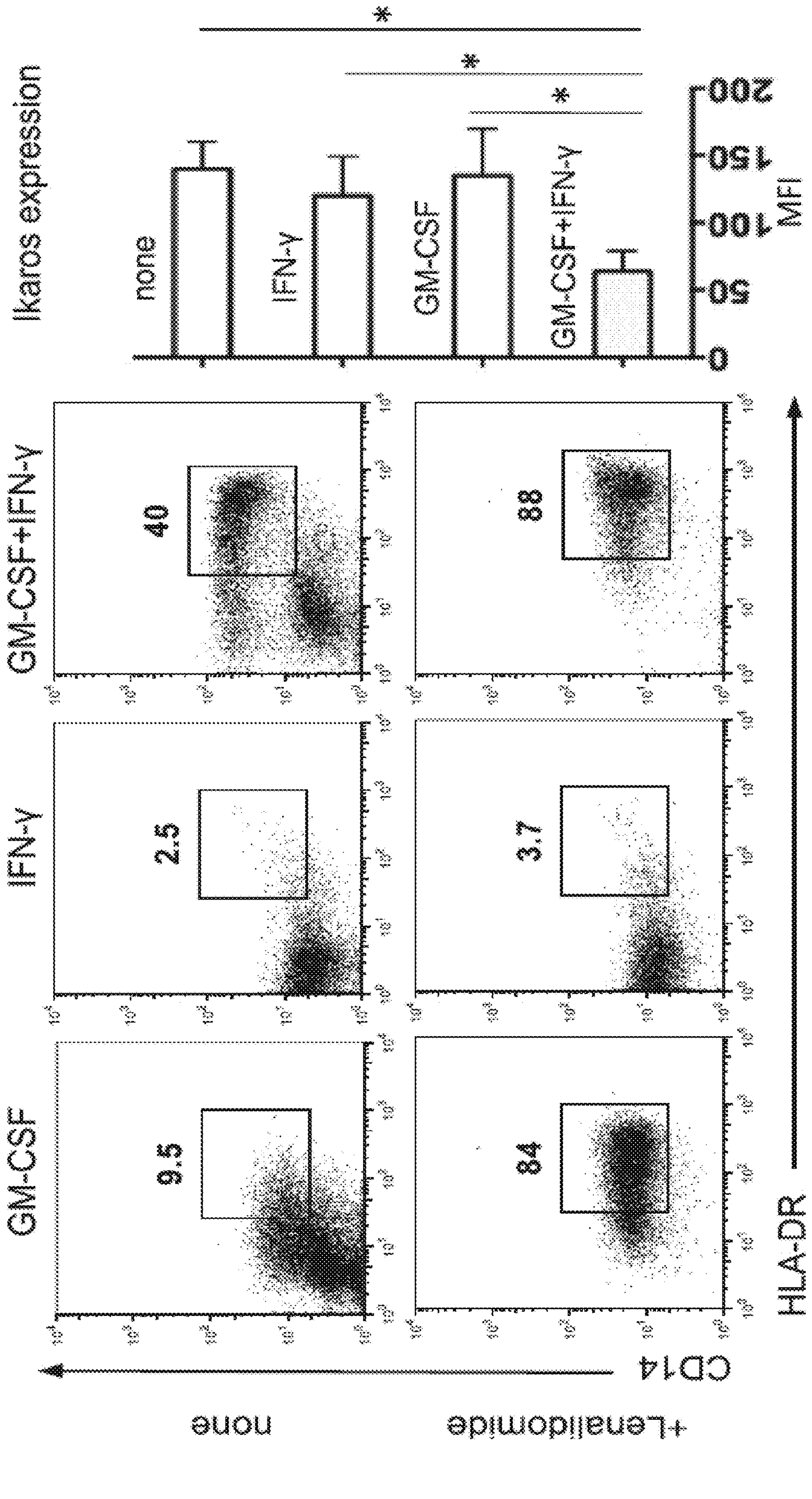

The level of Ikaros was measured in BMN progenitors incubated with or without low-dose IFN-γ and/or GM-CSF at days 1, 3, and 5. Downregulation of Ikaros was only observed when both IFN-γ and GM-CSF were present for at least 5 days, confirming their synergistic effect in this process (FIG. 20D). Next, Ikaros was downregulated in BMNs by adding lenalidomide and culturing these cells with either IFN-γ or GM-CSF. The incubation of BMNs with the combination of GM-CSF and lenalidomide, but not IFN-γ and lenalidomide, resulted in efficient development of $HLA\text{-}DR^+CD14^+$ hybrid cells (80%-90% among all BMNs) (FIG. 20D). These data confirm the hypothesis that the premature downregulation of Ikaros in concert with the macrophage stimulatory factor GM-CSF are requisite for the development of hybrid neutrophils from neutrophil progenitors.

Figure 21A:
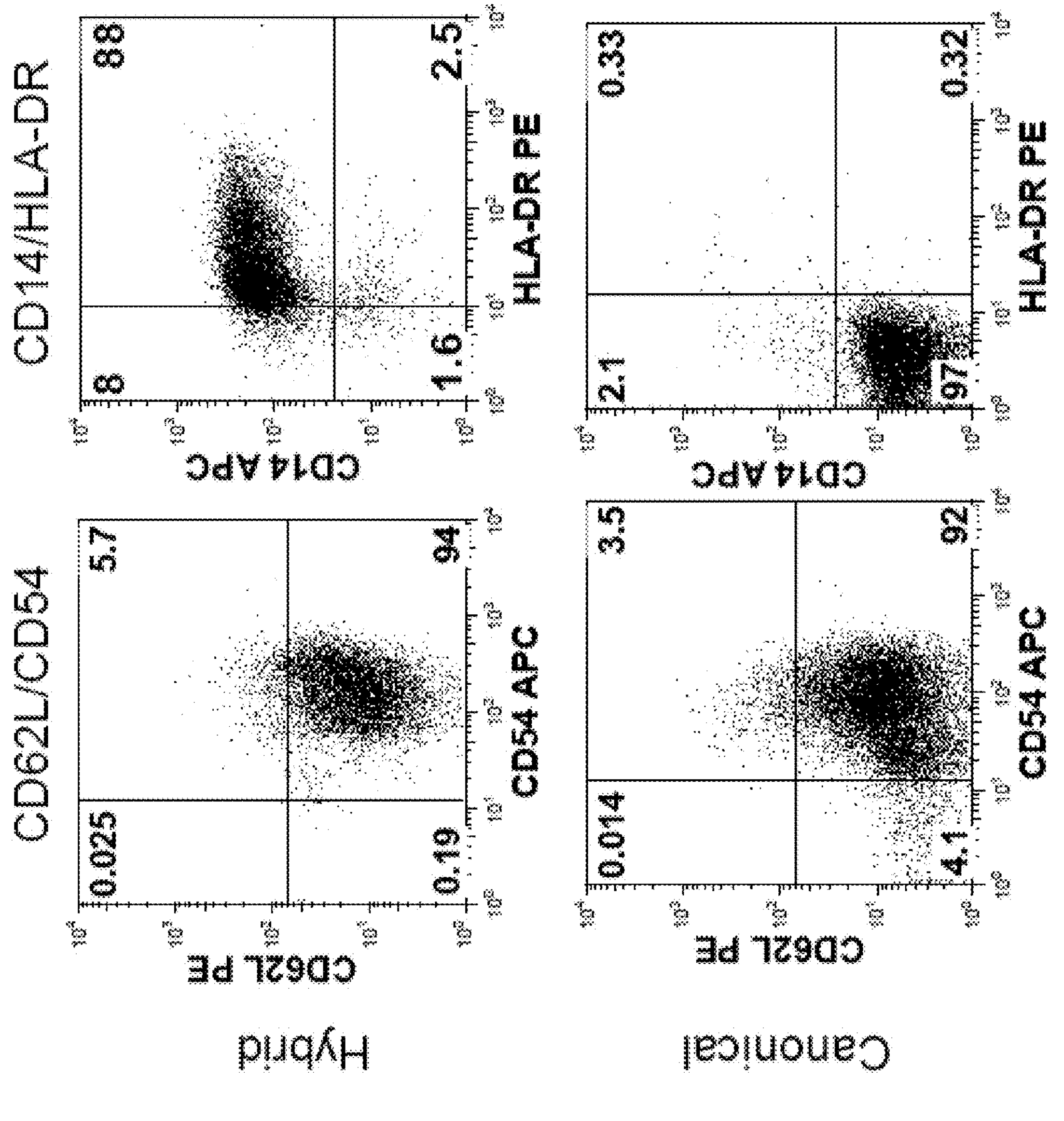
FIGS. 21A-21D are a series of graphs and images showing APC-like hybrid neutrophils are able to stimulate T cell responses.
Figure 21B:
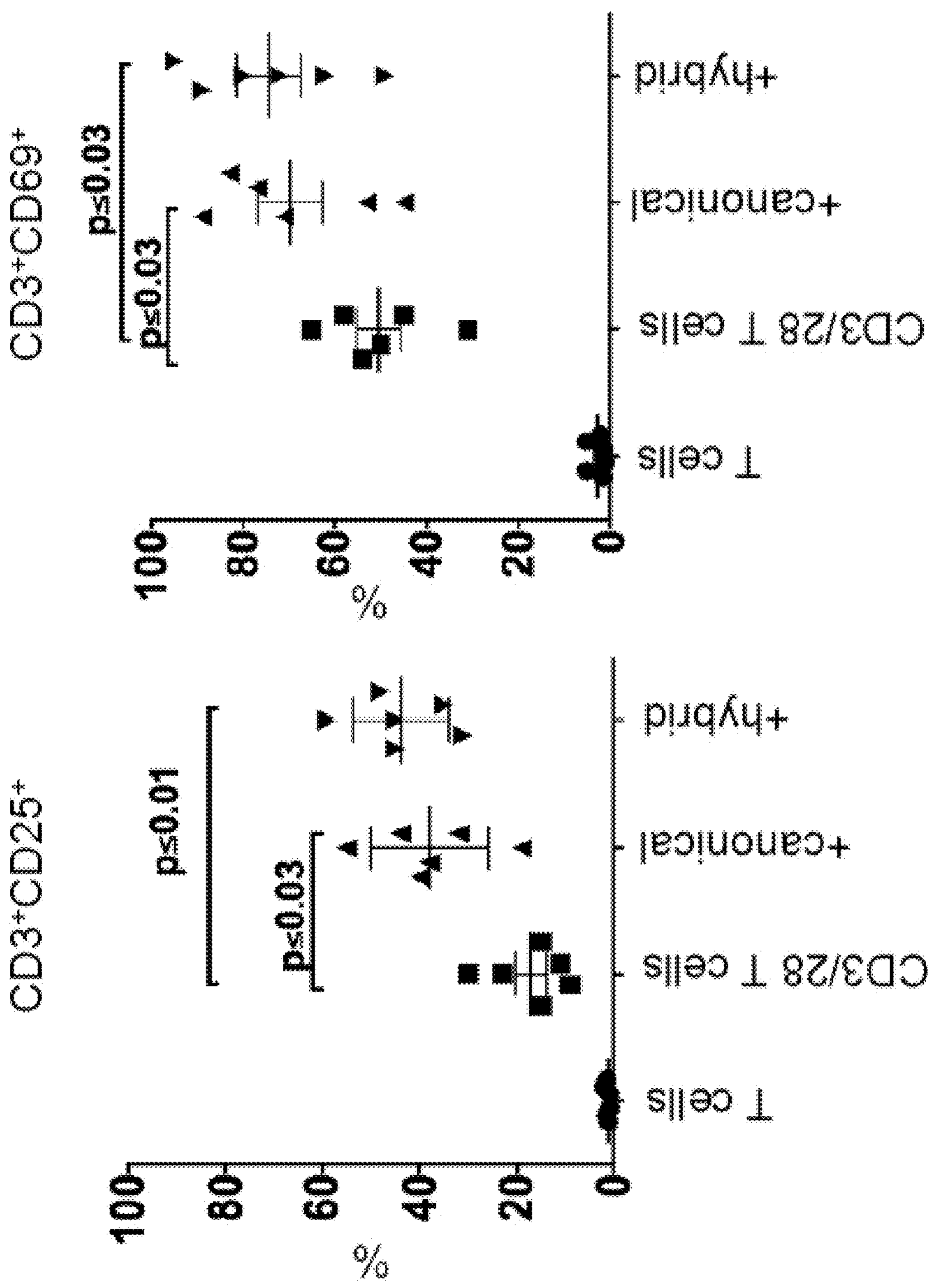
Figure 22A:
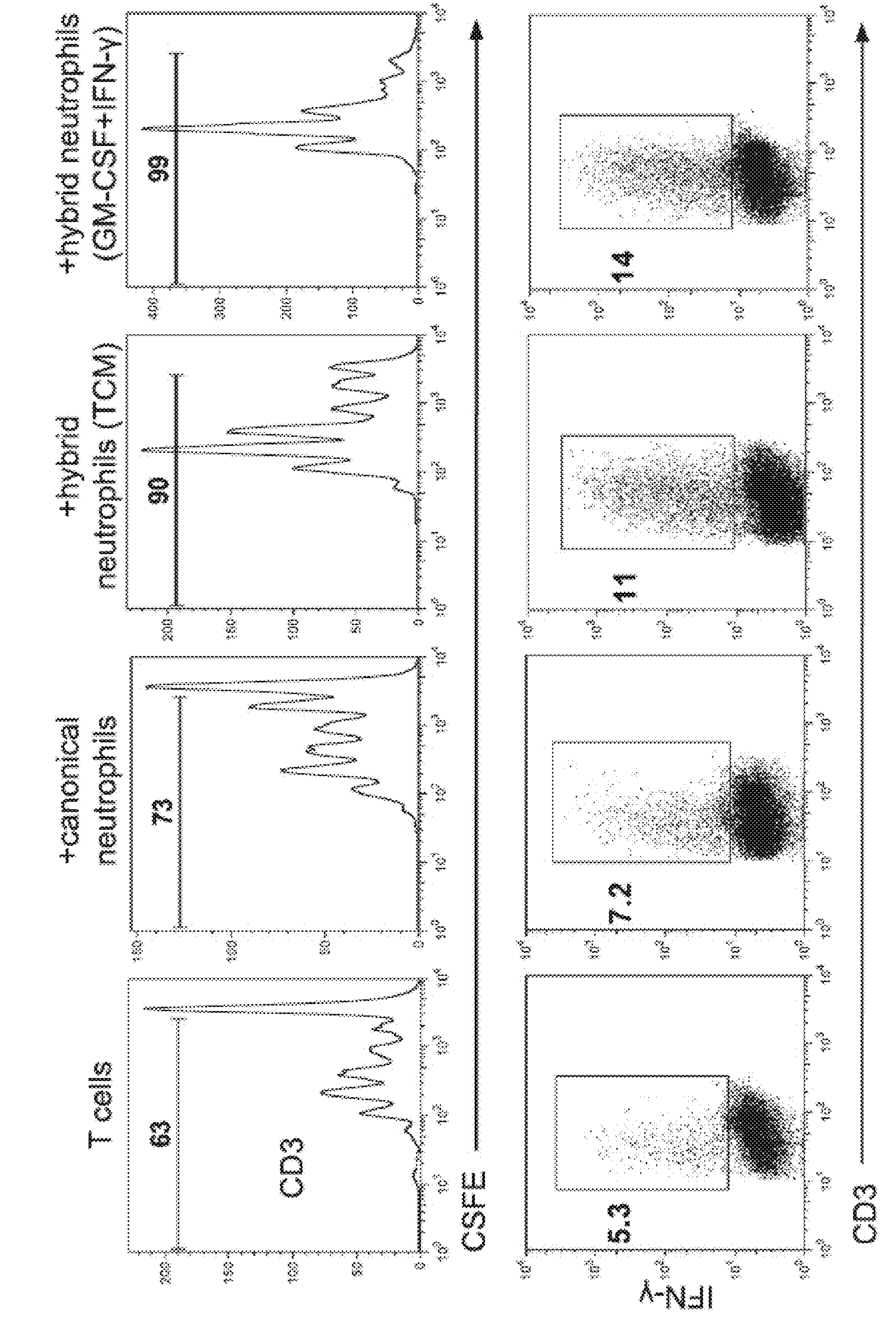
FIGS. 22A-22D are a series of graphs showing APC-like hybrid neutrophils stimulate antigen-nonspecific T cell responses.
Figure 22B:
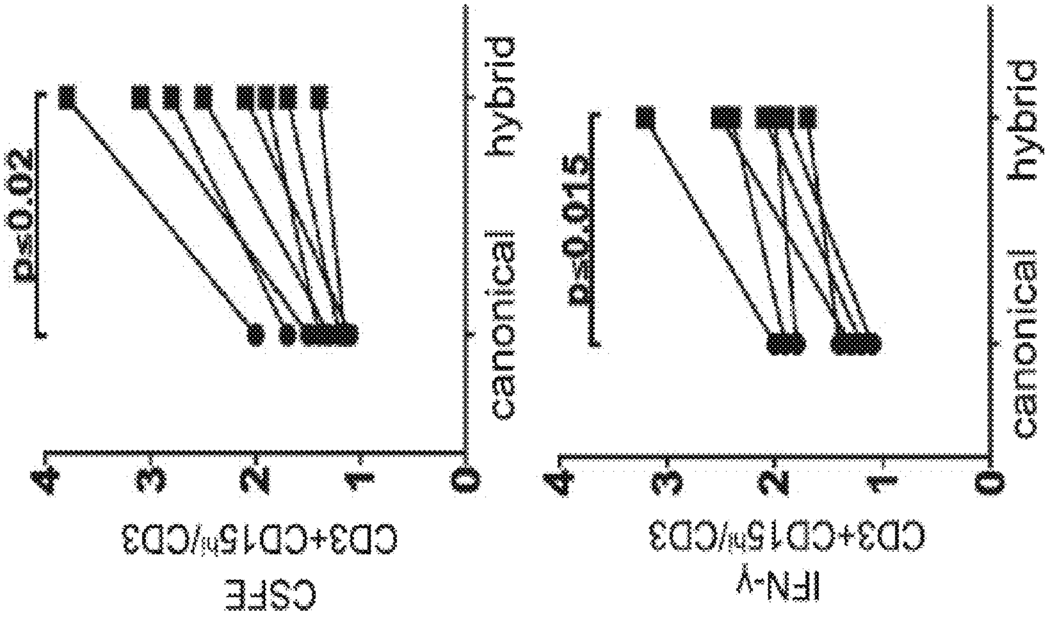
Figure 22C:
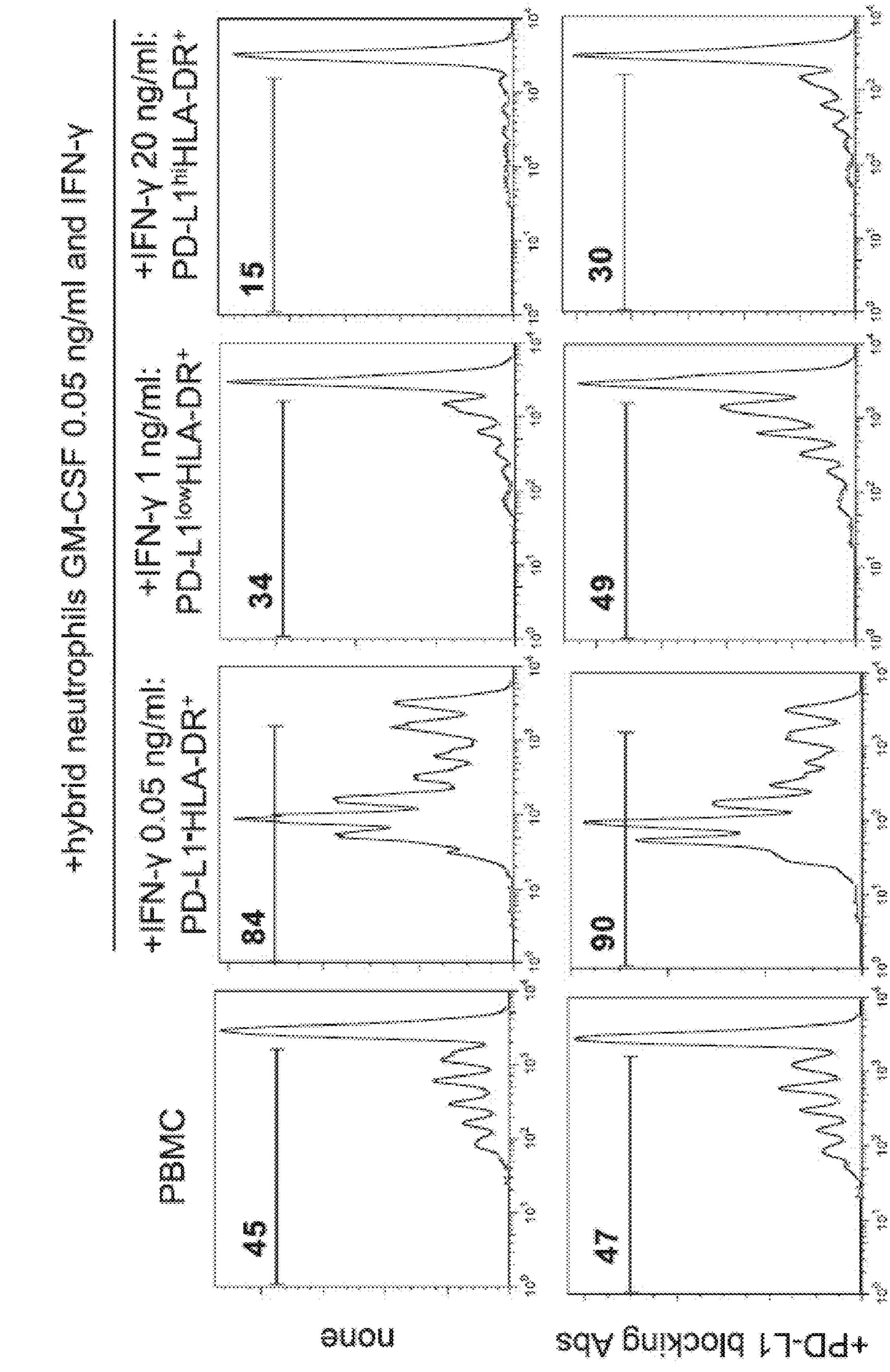
Figure 22D:
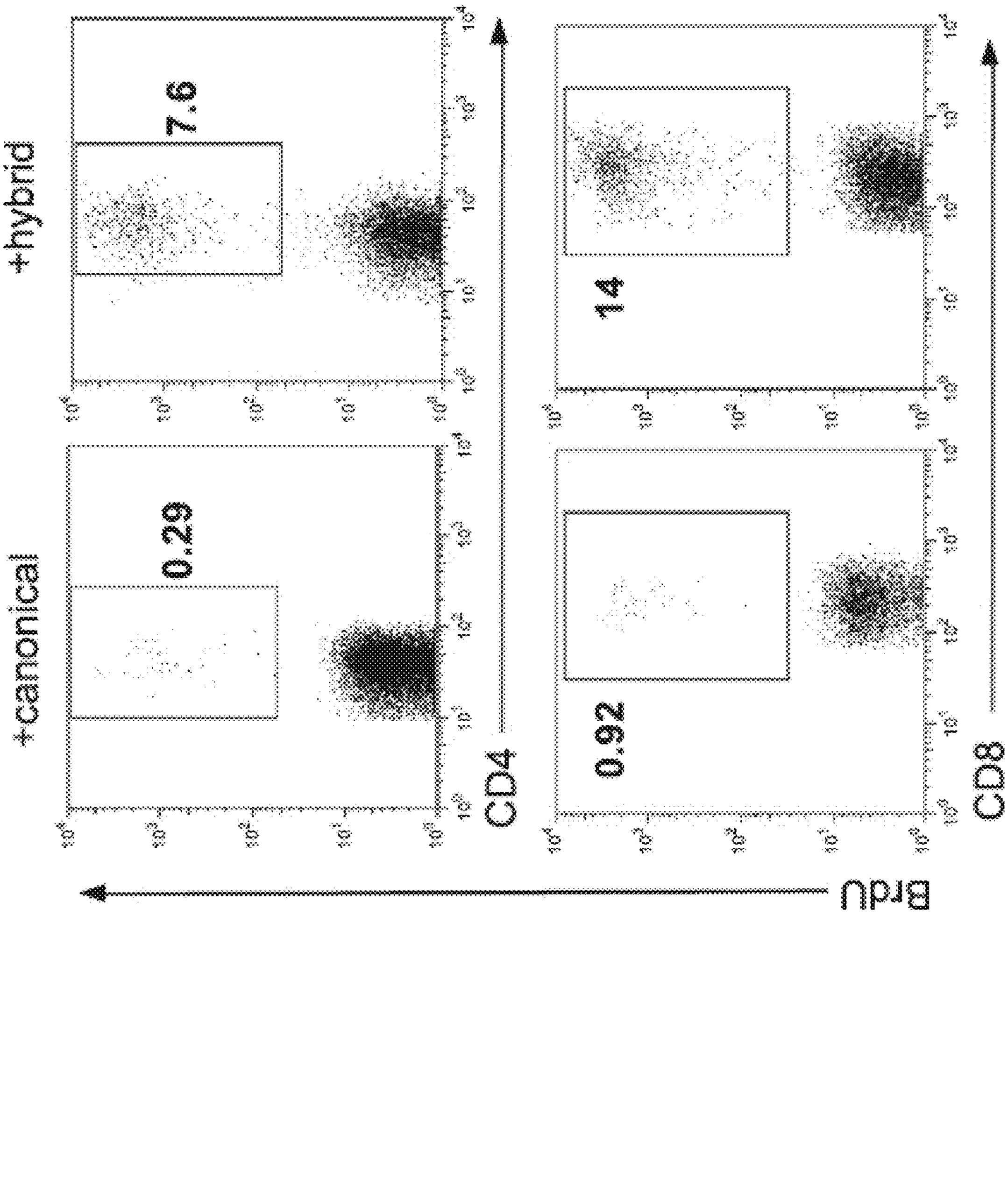

Example 13: BM-Derived Hybrid Neutrophils Recapitulate the Function of APC-Like Hybrid TANs It was investigated whether the BM-derived hybrid neutrophils also functionally resemble hybrid TANs in their ability to stimulate T cell responses. For this purpose, immature BMNs were differentiated into activated canonical and hybrid neutrophils (FIG. 21A) and co-cultured with autologous PBMCs stimulated with plate-bound anti-CD3 Abs. Both subsets of neutrophils augmented the expression of activation markers CD25 and CD69 on stimulated T cells to the same degree (FIG. 21B). However, HLA-$DR^+$ hybrid neutrophils exerted a significantly stronger stimulatory effect on T cell proliferation and IFN-γ production than the canonical neutrophils (FIGS. 22A-22B). The BM-derived hybrid neutrophils differentiated with low doses of IFN-γ and GM-CSF also recapitulated the T cell stimulatory activity of hybrid TANs (FIG. 22A). However, as described herein, the treatment of BMNs with a low dose of GM-CSF and IFN-γ at concentrations more than 1 ng/ml gradually induced the expression of PD-L1 on the HLA-$DR^+$ BMNs (FIG. 22D, lower panel). When PD-$L1^+$HLA-$DR^+$ BMNs were co-cultured with autologous PBMCs stimulated with anti-CD3 Abs, T cell proliferation was markedly suppressed (FIG. 22C, upper panel), which was substantially inhibited by PD-L1 blocking Abs (FIG. 22C, lower panel). Thus, high doses of IFN-γ can convert the T cell stimulatory HLA-$DR^+$ BMNs into a suppressive population via upregulation of PD-L1. These results demonstrate some functional plasticity in the APC-like neutrophils.

To determine whether the hybrid neutrophils are able to induce the proliferation of allogeneic T cells in a mixed-lymphocyte reaction, BM-derived hybrid and canonical neutrophils were co-cultured with allogeneic T cells purified from the peripheral blood of healthy donors. BrdU incorporation assays revealed that hybrid neutrophils, but not canonical neutrophils, were able to initiate the allogeneic proliferation of both CD4 and CD8 cells (FIG. 22D). In addition, similar to hybrid TANs, BM-derived hybrid neutrophils pulsed with a peptide pool of viral antigens were able to initiate the autologous memory CD8 and CD4 cell response more efficiently than canonical neutrophils (FIG. 22C). These data demonstrate the functional resemblance between BM-derived and tumor-derived hybrid neutrophils, and justify the use of this model to investigate additional functions of this rare subset of TANs.

Figure 23A:
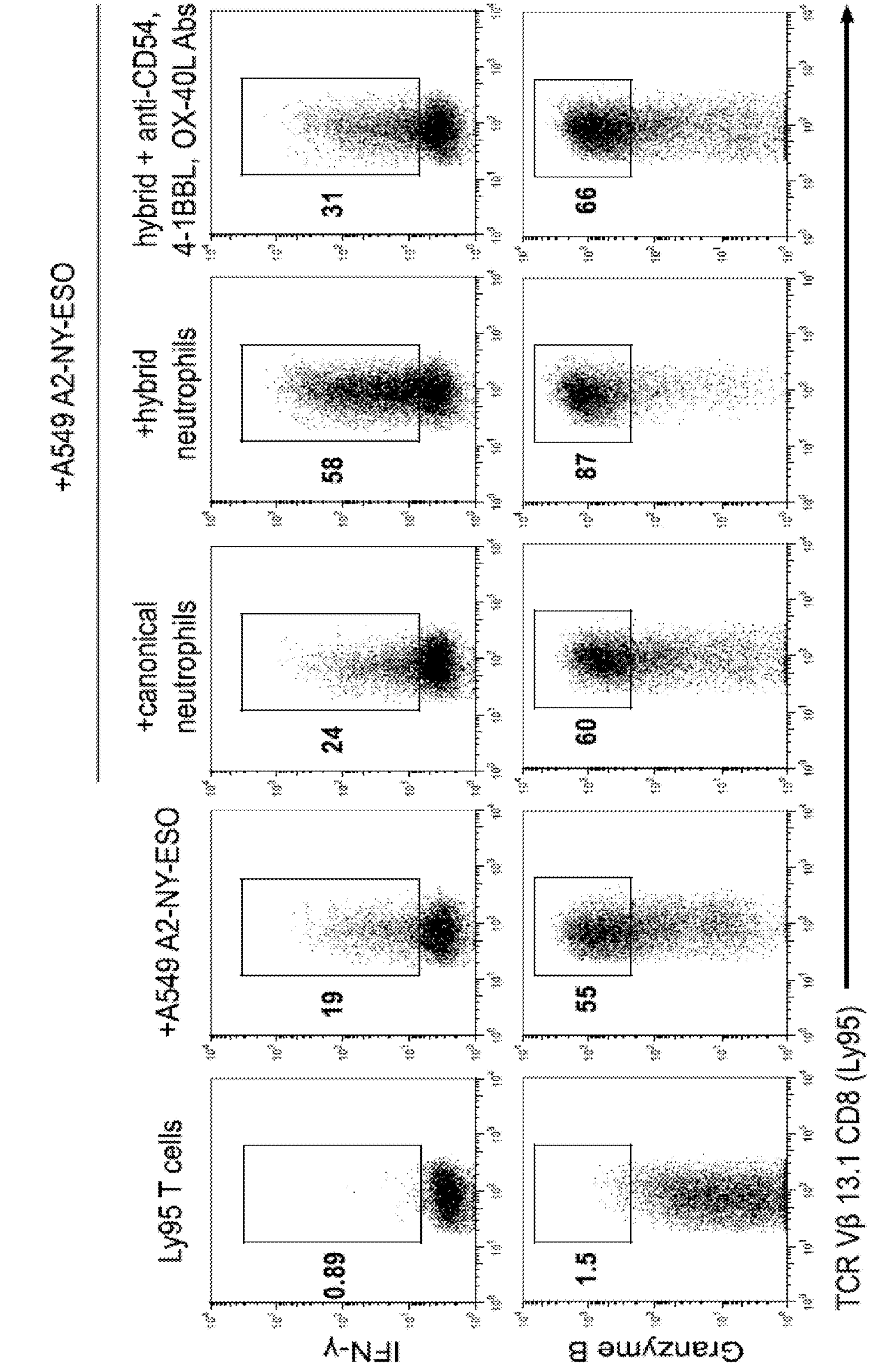
FIGS. 23A-23E are a series of graphs and images showing APC-like hybrid neutrophils are able to trigger and stimulate NY-ESO-specific effector T cell responses.

Example 14: APC-Like Hybrid Neutrophils Stimulate and Augment Anti-Tumor Effector T Cell Responses The effect of canonical and hybrid neutrophils on anti-tumor effector T cells was evaluated using a newly developed in vitro model. Human T cells were transduced with a high-affinity transgenic T cell receptor (TCR) called Ly95 that recognizes an HLA-A*0201-restricted peptide sequence in the human cancer testis antigen, NY-ESO-1 (Moon et al., 2016. *Clin. Cancer Res.* 22, 436-447). As target cells, a genetically modified A549 human lung adenocarcinoma cell line expressing the NY-ESO-1 protein in the context of HLA-A*0201 (A549 A2-NY-ESO-1 cells) (Moon et al., 2016. *Clin. Cancer Res.* 22, 436-447) was used. Co-culturing of Ly95 T cells with A549 A2-NY-ESO-1 tumor cells resulted in robust production of IFN-γ and Granzyme B in Ly95 T cells (FIG. 23A). When BM-derived hybrid neutrophils were added into this system, the production of IFN-γ and Granzyme B in Ly95 T cells was markedly elevated (FIGS. 23A-22B) and increased compared with canonical neutrophils. Of note, the addition of the hybrid neutrophils into Ly95 T cells co-cultured with control A549 cells did not induce the production of these factors, indicating that hybrid neutrophil-mediated stimulation of Ly95 cells was NY-ESO-1 specific and not the result of allostimulation.

Figures 21C, 21D:
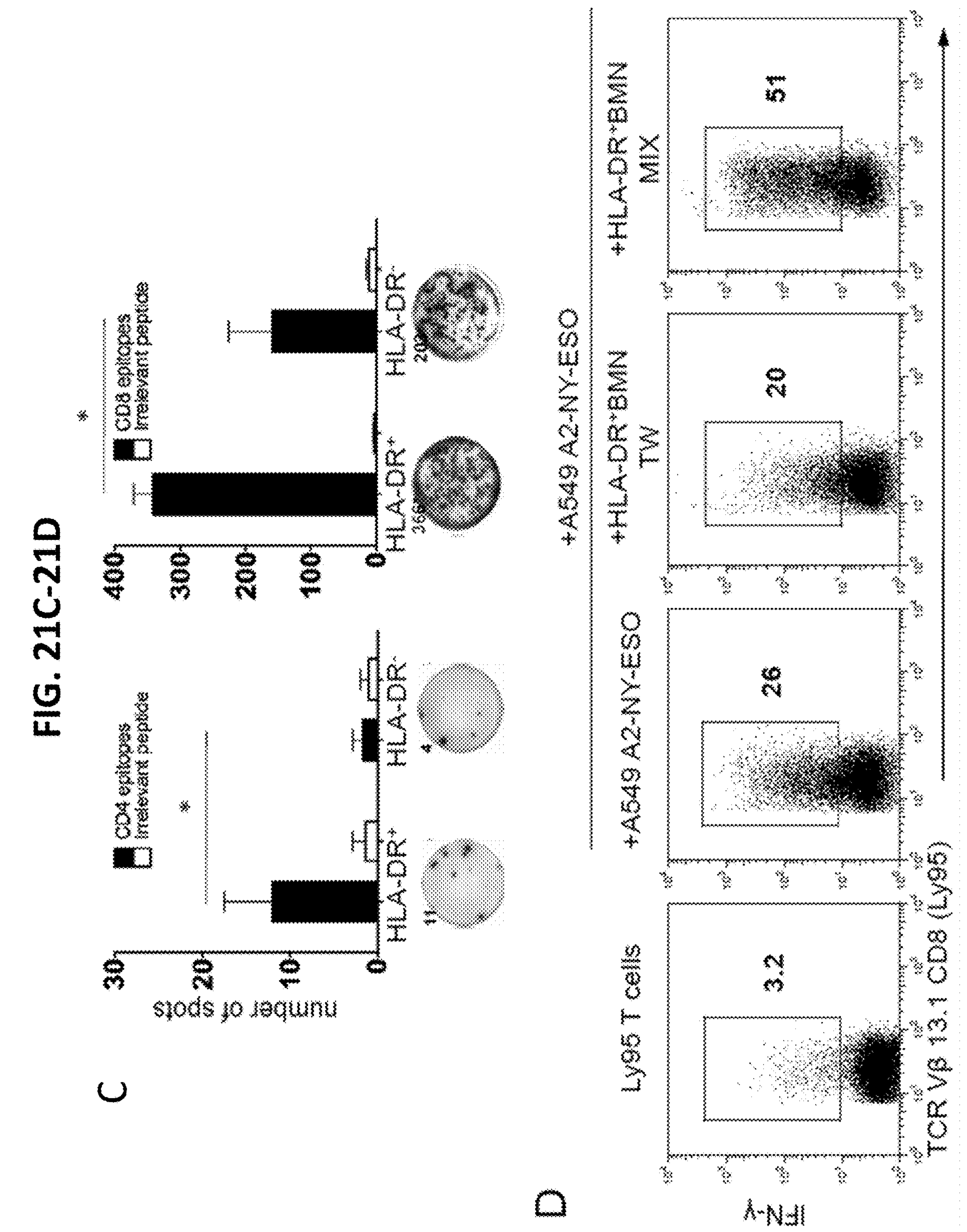
Figures 23B, 23C:
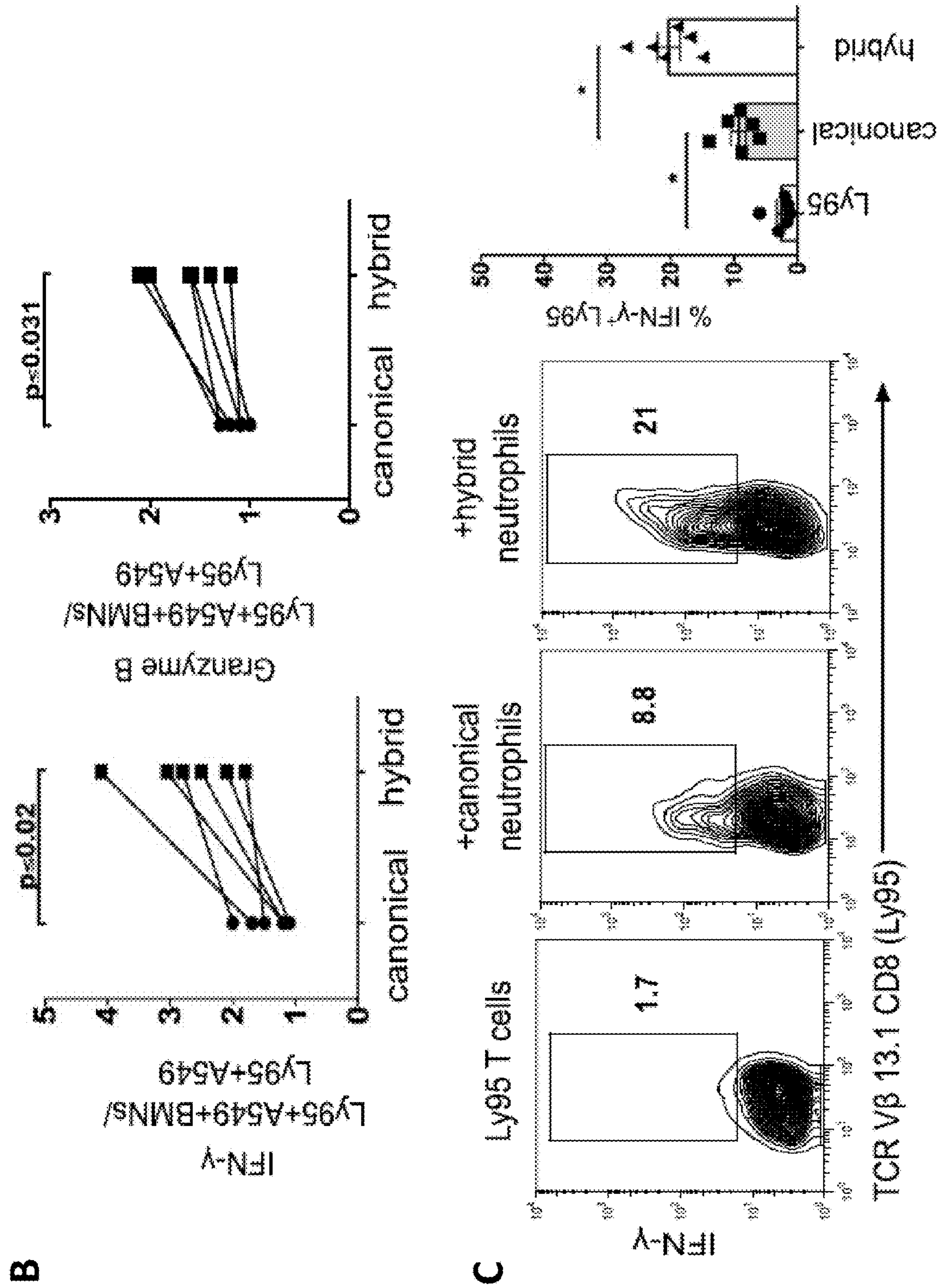

HLA-$DR^+$ hybrid BMNs induced the stimulation of IFN-γ production by Ly95 T cells only when the cells were in direct contact (FIG. 21D). Since hybrid BMNs are characterized by increased expression of co-stimulatory molecules OX40L, 4-1BBL CD86, and CD54 (FIGS. 14D-14E, and 15D), Ly95 T cells were co-cultured with A549 A2-NY-ESO-1 tumor cells and with hybrid BMNs in the presence of blocking Abs to these upregulated co-stimulatory molecules. FIG. 23A shows a representative experiment in which the stimulatory effect of hybrid neutrophils was partially abrogated in the presence of anti-CD54, 4-1BBL, OX-40L, and CD86 blocking Abs (FIG. 23A). Next it was determined whether APC-like hybrid neutrophils could directly trigger NY-ESO-1 specific response of Ly95 cells. Given that Ly95 cells specifically recognize the HLA-A*02-restricted peptide of NY-ESO-1, HLA-A*$02^+$ BM-derived canonical and hybrid neutrophils were pulsed with the NY-ESO-1 (157-165) peptide and then co-cultured with Ly95 T cells for 24 hr. Hybrid HLA-A* $02^+$-HLA-$DR^+$ hybrid neutrophils preloaded with the peptide triggered IFN-γ production in Ly95 T cells more effectively than peptide-loaded canonical neutrophils (FIG. 23C). These data demonstrate that hybrid neutrophils can trigger and significantly augment the activation of antigen-specific effector T cells.

Figures 23D, 23E:
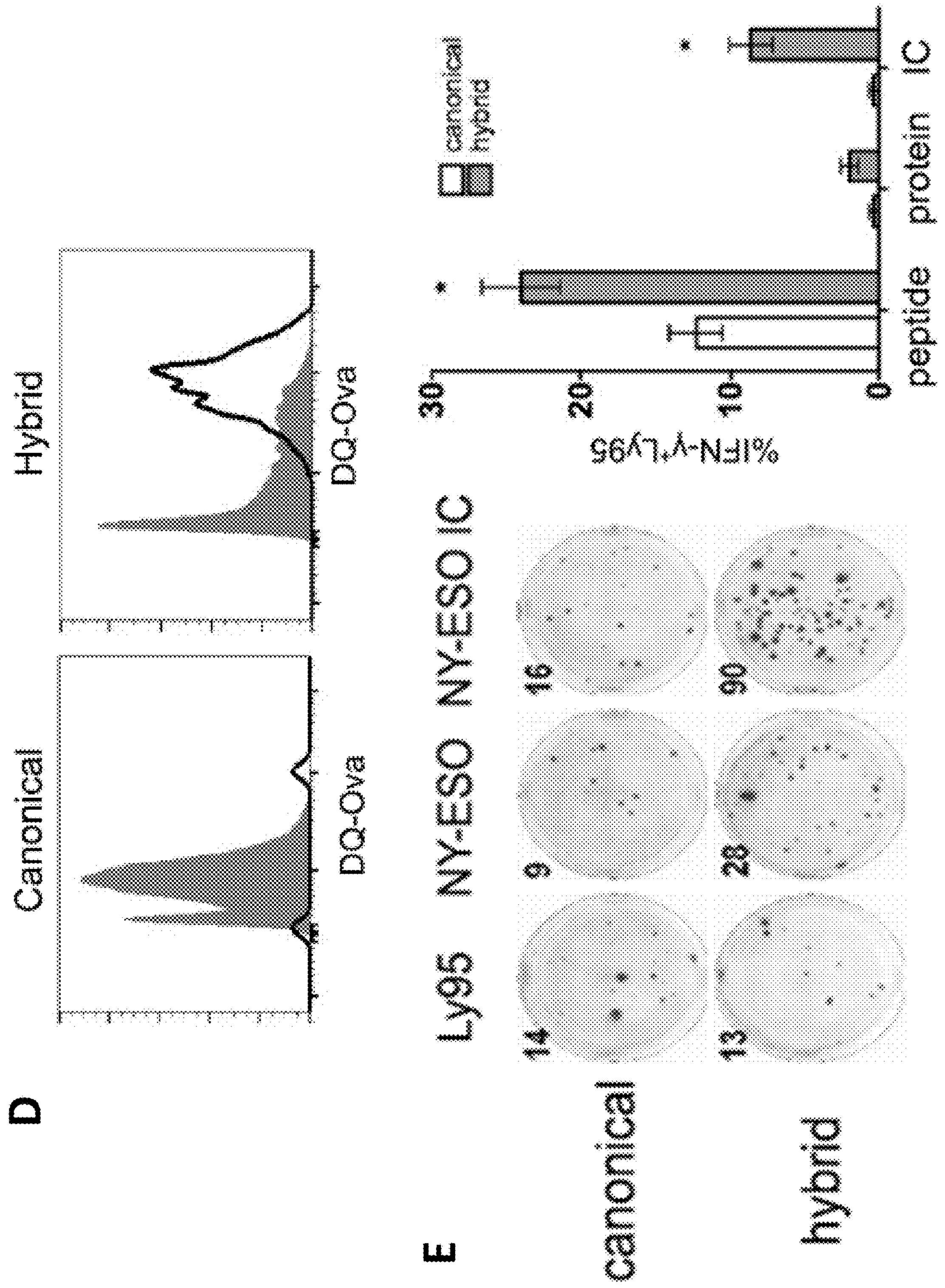

Example 15: APC-Like Hybrid Neutrophils are Able to Cross-Present Tumor Antigens Hybrid neutrophils were able to take up and process ovalbumin (DQ-OVA) to a higher degree than canonical neutrophils (FIG. 23D). To evaluate whether hybrid neutrophils are able to present extracellular protein to effector CD8 cells (cross-presentation), HLA-A*02-positive BM-derived hybrid and canonical neutrophils were preloaded with full-length NY-ESO-1 protein and mixed with Ly95 cells for 24 hr (FIG. 23E). These canonical and hybrid neutrophils were not sufficient to trigger Ly95 T cell response. Ly95 T cells mixed with control, unloaded neutrophils generated a low background of IFN-γ-positive spots due to endogenous activity of Ly95 cells from the prior CD3 stimulation required for expansion of these cells after TCR transduction (FIG. 23E). Next, the Fc receptors (FcgR) that are highly expressed on hybrid neutrophils (FIG. 2D) were employed and the NY-ESO-1 protein delivered as an immunoglobulin G (IgG)-immune complex to trigger the more efficient FcgR-mediated antigen uptake and presentation. For this purpose, the neutrophil subsets were pre-exposed to NY-ESO-1 immune complexes formed by incubating the NY-ESO-1 protein with anti-NY-ESO-1 monoclonal Abs and mixed them with Ly95 cells for 24 hr. Under these conditions, hybrid neutrophils, but not canonical neutrophils, were able to cross-present NY-ESO epitopes and induce low-level, but NY-ESO-specific, production of IFN-γ by Ly95 T cells (FIG. 7E). These data demonstrate that hybrid neutrophils have the ability to take up and cross-present exogenous tumor antigens.

Figure 9:
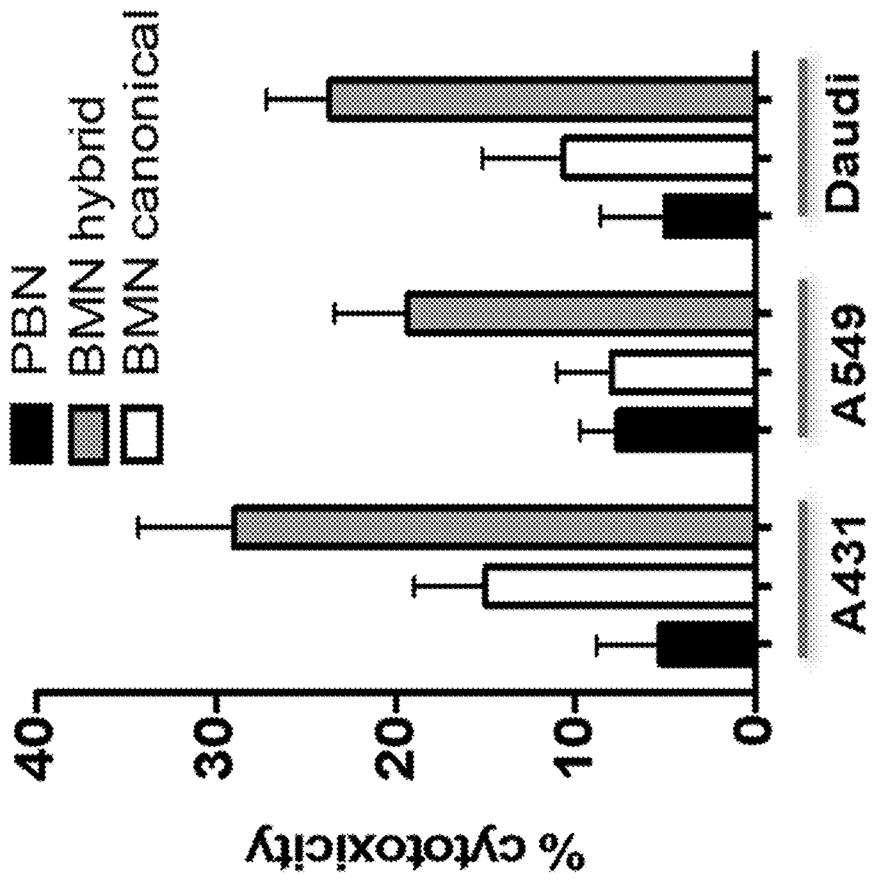
FIG. 9 is a graph showing the cytotoxic activity of neutrophils. A431, A549 and Daudi tumor cell lines were labeled with cell dye PKH67 and opsonized with cetuximab and rituximab at a concentration of 1 ug/ml. PBN, hybrid and canonical BMNs were incubated with cetuximab-opsonized A431 cell line, cetuximab-opsonized A549 cell line and rituximab-opsonized Daudi cell line at a ratio of 10:1. Sixteen hours later, floating and adherent cells were collected using trypsin and stained with a viability dye FVD eFluor® 660. Tumor cell cytotoxicity was calculated as a percent of $PKH^+FVD660^+$ cells.

Example 16: Hybrid $CD14^+HLA-DR^+$ $CD32^{hi}CD64^{hi}$ Neutrophils Efficiently Phagocytose Bacteria and Mediate a High Level of Antibody Dependent Cell Cytotoxicity $CD64^{hi}CD32^{hi}$ hybrid neutrophils (which could be generated in large numbers from immature bone marrow or peripheral blood) are powerful effector cells that trigger sufficient removal of tumor cells or infectious pathogens through ADP or ADCC. Support for this claim comes from comparative analysis described herein of canonical and hybrid neutrophils that revealed that hybrid neutrophils are characterized by: 1) augmented ability to phagocytose bacteria (FIG. 5A), 2) expression of very high levels of FcRI (CD64) and FcRII (CD32) (FIG. 5D). Of note, the high affinity FcγRI/CD64 represents the most potent neutrophil FcγR for induction of ADCC, 3) increased ability to mediate the high level of antibody-dependent phagocytosis/trogocytosis (FIG. 5B), 4) ability to mediate the ADCC towards different types of cancer: (1) human epidermoid carcinoma (A431 cell line), (2) adenocarcinomic human alveolar basal epithelial cells (A549 cell line), and (3) B lymphoblasts (Daudi cell line) (FIG. 9), and 5.) ability to inhibit A549 tumor growth in NOD scid gamma (NSG) mice (FIG. 10).

The disclosures of each and every patent, patent application, and publication cited herein are hereby incorporated herein by reference in their entirety. While the present invention has been disclosed with reference to specific embodiments, it is apparent that other embodiments and variations of the present invention may be devised by others skilled in the art without departing from the true spirit and scope of the invention. The appended claims are intended to be construed to include all such embodiments and equivalent variations.

What is claimed:

1. A method of inhibiting tumor growth in a human subject, the method comprising:

(a) administering to the subject an effective amount of an anti-tumor antibody or an antigen-binding fragment thereof; and (b) administering to the subject an effective amount of a human hybrid neutrophil, wherein the hybrid neutrophil co-expresses the canonical neutrophil associated molecules arginase-1(Arg1), myeloperoxidase (MPO), CD66b, and CD15, and the antigen presenting cell (APC) associated molecules CD14, HLA-DR, CD32, CD64, and CD89, thereby inhibiting tumor growth in the subject.

2. The method of claim 1, wherein the human hybrid neutrophil further expresses at least one molecule selected from the group consisting of: MHC class I, MHC class II, OX40L, 4-1BBL, CD86, CD40, and CCR7.

3. The method of claim 1, wherein the expression of any one of the molecules is increased relative to expression of the molecule on a canonical neutrophil.

4. The method of claim 1, wherein the human hybrid neutrophil co-expresses Arg1, MPO, CD66b, CD15, CD14, HLA-DR, MHC class I, OX40L, 4-1BBL, CD86, CD40, CCR7, CD32, CD64, and CD89.

5. The method of claim 1, wherein the expression of Arg1, MPO, CD66b, CD15, CD14, HLA-DR, CD32, CD64 and/or CD89 is increased relative to expression of the molecule on a canonical neutrophil.

6. The method of claim 1, wherein the anti-tumor antibody is selected from the group consisting of: anti-Her2/neu antibody, rituximab, necitumumab, panitumumab, and cetuximab.

7. The method of claim 1, wherein the step of administering to the subject an effective amount of a human hybrid neutrophil increases antibody-dependent cellular cytotoxicity (ADCC), antibody-dependent phagocytosis (ADP), antibody-dependent trogocytosis or effector T cell response in the subject.

8. The method of claim 1, wherein the human hybrid neutrophil is generated ex vivo in a biological sample obtained from the subject.

9. The method of claim 8, wherein the biological sample is blood or bone marrow.

10. The method of claim 9, wherein the hybrid neutrophil is generated by a method comprising contacting a composition comprising a bone marrow (BM) immature CD15-positive (CD15+) cell with an amount of tumor conditioned medium.

11. The method of claim 1, wherein the human hybrid neutrophil is generated in situ in the subject.

12. The method of claim 11, wherein the human hybrid neutrophil is generated in situ by administering to the subject an amount of granulocyte macrophage colony stimulating factor (GM-CSF) and at least one agent selected from the group consisting of: IFN-γ and lenalidomide.

13. The method of claim 1, wherein the step of administering to the subject an effective amount of a human hybrid neutrophil is followed by the step of administering to the subject an effective amount of an anti-tumor antibody or an antigen-binding fragment thereof.

14. The method of claim 1, wherein the step of administering to the subject an effective amount of a human hybrid neutrophil is concurrent with the step of administering to the subject an effective amount of an anti-tumor antibody or an antigen-binding fragment thereof.

15. The method of claim 1, wherein the tumor comprises non-small cell lung cancer (NSCLC).

16. A method of treating a tumor in a human subject, the method comprising:

(a) administering to the subject an effective amount of an anti-tumor antibody or an antigen-binding fragment thereof, and (b) administering to the subject an effective amount of a human hybrid neutrophil, wherein the hybrid neutrophil co-expresses the canonical neutrophil associated molecules arginase-1(Arg1), myeloperoxidase (MPO), CD66b, and CD15, and the antigen presenting cell (APC) associated molecules CD14, HLA-DR, CD32, CD64, and CD89, thereby treating the tumor in the subject.

* * * * *